(12) United States Patent
Hubschwerlen et al.

(10) Patent No.: US 7,999,115 B2
(45) Date of Patent: Aug. 16, 2011

(54) SPIRO ANTIBIOTIC DERIVATIVES

(75) Inventors: Christian Hubschwerlen, Durmenach (FR); Jean-Philippe Surivet, Kembs (FR); Cornelia Zumbrunn-Acklin, Basel (CH)

(73) Assignee: Actelion Pharmaceutical Ltd., Allschwil (SE)

( * ) Notice: Subject to any disclaimer, the term of this patent is extended or adjusted under 35 U.S.C. 154(b) by 92 days.

(21) Appl. No.: 12/439,571

(22) PCT Filed: Aug. 29, 2007

(86) PCT No.: PCT/IB2007/053472
§ 371 (c)(1),
(2), (4) Date: Mar. 2, 2009

(87) PCT Pub. No.: WO2008/026172
PCT Pub. Date: Mar. 6, 2008

(65) Prior Publication Data
US 2009/0270375 A1    Oct. 29, 2009

(30) Foreign Application Priority Data

Aug. 30, 2006 (WO) .................. PCT/IB2006/053012
Nov. 1, 2006 (WO) .................. PCT/IB2006/054045

(51) Int. Cl.
*C07D 263/52* (2006.01)
*C07D 263/58* (2006.01)
(52) U.S. Cl. ...................................... 548/216; 548/221
(58) Field of Classification Search .................. 548/216, 548/221
See application file for complete search history.

(56) References Cited

U.S. PATENT DOCUMENTS

| 4,244,961 A | 1/1981 | Kluge et al. |
| 4,353,901 A | 10/1982 | Clark |

FOREIGN PATENT DOCUMENTS

| EP | 438233 | 7/1991 |
| WO | WO 96/33195 | 10/1996 |
| WO | WO 00/40554 | 7/2000 |
| WO | WO 00/78748 | 12/2000 |
| WO | WO 02/08224 | 1/2002 |
| WO | WO 03/087098 | 10/2003 |
| WO | WO 03/095438 | 11/2003 |
| WO | WO 2004/002490 | 1/2004 |
| WO | WO 2004/014361 | 2/2004 |
| WO | WO 2004/022558 A | 3/2004 |
| WO | WO 2004/035569 | 4/2004 |
| WO | WO 2004/089947 | 10/2004 |
| WO | WO 2006/021448 | 3/2006 |
| WO | WO 2006/032466 | 3/2006 |
| WO | WO 2006/046552 | 4/2006 |
| WO | WO 2006/038172 A | 4/2008 |

OTHER PUBLICATIONS

Henry Chambers, Antimicrobial Agents; General Considerations, in Goodman & Gilman's the Pharmacological Basis of Therapeutics 1143 (10th ed. 2001).*
Alfred Burger, Isosterism and Bioisosterism in Drug Design, in Progress in Drug Research 287-328 (Ernst Jucker, ed., Birkhauser Verlag, 1991).*
George Patani & Edmond LaVoie, Bioisosterism: A Rational Approach in Drug Design, 96 Chem. Rev. 3147 (1996).*
Gould, et al. "Salt selection for basic drugs," International Journal of Pharmaceutics, vol. 33, pp. 201-217, (1986).
Mitsunobu, Oyo, "The Use of Diethyl Azodicarboxylate and Triphenylphosphine in Synthesis and Transformation of Natural Products," Department of Chemistry, College of Science and Engineering, Aoyama Gakuin University, Tokyo, Japan, Synthesis, pp. 1-28, 1981.
Benz, Günter, "2.3: Synthesis of Amides and Related Compounds," Comprehensive Organic Synthesis, B.M. Trost and I. Fleming, Eds; Pergamon Press: New York, vol. 6, pp. 381-417, 1991.
Palucki, M. et al., "Synthesis of Oxygen Heterocycles via a Palladium-Catalyzed C-O Bond-Forming Reaction," Journal of the American Chemical Society, vol. 118, pp. 10333-10334, 1996.
Klapars, A. et al., "A General and Efficient Copper Catalyst for the Amidation of Aryl Halides," Journal of the American Chemical Society, vol. 124, pp. 7421-7428, 2002.

(Continued)

*Primary Examiner* — Karlheinz R Skowronek
*Assistant Examiner* — Sean Basquill
(74) *Attorney, Agent, or Firm* — Hunton & Williams LLP

(57) ABSTRACT

The invention relates to compounds of formula (I) wherein $R^1$ represents H, alkyl, alkoxy, cyano or halogen; one of U and X represents CH or N and the other represents CH, or, in the case of U, may also represent $CR^a$ and, in the case of X, may also represent $CR^b$; $R^a$ represents halogen; $R^b$ represents halogen or alkoxy; B represents N, D represents $CH_2$ and A represents $CH(OH)CH_2$ or $CH_2CH_2$, or B represents CH, D represents $CH_2$ or O and A represents $OCH_2$, $CH_2CH(OH)$, $CH(OH)CH_2$, $CH(OH)CH(OH)$, $CH=CH$, $CH_2CH_2$ or NHCO, or also B represents C(OH), D represents $CH_2$ and A represents $OCH_2$, $CH_2CH(OH)$, $CH(OH)CH_2$, $CH(OH)CH(OH)$, $CH=CH$, $CH_2CH_2$ Or NHCO; $R^2$ represents H, alkyl, alkenyl, hydroxyalkyl or alkoxycarbonylalkyl; and E represents naphthyl or a binuclear heterocyclic group; and to salts of such compounds. These compounds are useful as antimicrobial agents.

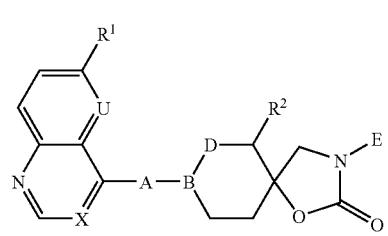

(I)

12 Claims, No Drawings

OTHER PUBLICATIONS

Kolb, H. et al., "Catalytic Asymmetric Dihydroxylation," Chemical Review for the American Chemical Society, vol. 94, pp. 2483-2547, 1994.

Blakemore, Paul, "The modified Julia olefination: alkene synthesis via the condensation of metallated heteroarylalkylsulfones with carbonyl compounds," Journal of the Royal Society of Chemistry, Perkin Trans. 1, pp. 2563-2585, 2002.

Echavarren, A. et al., "Palladium-catalyzed coupling of aryl triflates with organostannanes," Journal of the American Chemical Society, vol. 109, pp. 5478-5486, 1987.

Kocienski, P.J., "Protecting Groups," Thieme-Foundations of Organic Chemistry Series, pp. 1-2, 1994.

Corey, E.J. et al., "Dimethyloxosulfonium Methylide ((CH)SOCH) and Dimethylsulfonium Methylide ((CH)SCH). Formation and Application to Organic Synthesis," Journal of the American Chemical Society, vol. 87, pp. 1353-1364, 1965.

Borredon, E. et al., "Epoxydation en milieu heterogene solide-liquide: Effet des interactions a l'interface sur la stabilite de l'ylure de dimethylsulfonium—Consequences sur la stereochimie de la reaction d'epoxydation," Tetrahedron Letters, vol. 28, No. 17, pp. 1877-1880, 1987.

Mancuso, A. et al., "Oxidation of long-chain and related alcohols to carbonyls by dimethyl sulfoxide 'activated' by oxalyl chloride," Journal of Organic Chemistry, vol. 43, pp. 2480-2482, 1978.

Dess, D.B. et al., "Readily accessible 12-1-5 oxidant for the conversion of primary and secondary alcohols to aldehydes and ketones," Journal of Organic Chemistry, vol. 48, pp. 4155-4156, 1983.

Furstoss, R. et al., "Synthesis of bridged azabicyclic ketones. Solvolysis of enol ehter and ethylene ketal N-chloramines in acidic medium," Canadian Journal of Chemistry, vol. 54, pp. 3569-3579, 1976.

Singh, C. et al., "Protection of the Carbonyl Group as 1,2,4-Trioxane and Its Regeneration under Basic Conditions," Organic Letters by the American Chemical Society, vol. 7, pp. 5673-5676, 2005.

Wipf, P. et al., "Total Synthesis of a Stereoisomer of Bistramide C and Assignment of Configuration of the Natural Product," Chemistry—A European Journal, vol. 8, No. 7, pp. 1670-1681, 2002.

Suggs, J.W. et al., "Facile Synthesis of 8-substituted quinolines," Journal of Organic Chemistry, vol. 45, pp. 1514-1515, 1980.

Miyaura, N. et al., "The Palladium-Catalyzed Cross-Coupling Reaction of Phenylboronic Acid with Haloarenes in the Presence of Bases," Synthetic Communications, vol. 11, pp. 513-519, 1981.

Cha, J.K. et al., "Acyclic Stereocontrol Induced by Allylic Alkoxy Groups. Synthetic Applications of Stereoselective Dihydoxylation in Natural Product Synthesis," Chemical Review for the American Chemical Society, vol. 95, pp. 1761-1795, 1995.

Zhang, H.X. et al., "Palladium- and molybdenum-catalyzed hydrostannation of alkynes. A novel access to regio- and stereodefined vinylstannanes," Journal of Organic Chemistry, vol. 55, pp. 1857-1867, 1990.

Corey, E.J. et al., "A Synthetic method for Formyl→Ethynyl Conversion (RCHO→RC≡CH or RC≡CR)," Tetrahedron Letters, vol. 36, pp. 3769-3772, 1972.

Ohira, Susumu, "Methanolysis of Dimethyl (1-Diazo-2-oxopropyl) Phosphonate: Generation of Dimethyl (Diazomethyl) Phosphonate and Reaction with Carbonyl Compounds," Synthetic Communications, vol. 19, pp. 561-564, 1989.

Hodgson, D. et al., "Extended Scope of Dirhodium (II)-Catalysed Enantioselective Intramolecular 1,3-Dipolar Cycloadditions of Carbonyl Ylides with Alkene and Alkyne Dipolarophiles," Synlett, Georg Thieme Verlag Stuttgard, NY, No. 1, pp. 59-62, 2003.

Müller, S. et al., "An Improved One-Pot Procedure for the Synthesis of Alkynes from Aldehydes," Synlett, George Thieme Verlag Stuttgard, NY, Letter received Mar. 1, 1996, pp. 521-522, 1996.

Magnus, P. et al., "A model for the proposed mechanism of action of the potent antitumor antibiotic esperamicin A1," Journal of the American Chemical Society, vol. 110, pp. 1626-1628, 1988.

Trost, B. et al., "Chemoselective Oxidation of Sulfides to Sulfones with Potassium Hydrogen Persulfate," Tetrahedron Letters, vol. 22, No. 14, pp. 1287-1290, 1981.

Schultz, H. et al., "New Catalysts for the Oxidation of Sulfides to Sulfones with Hydrogen Peroxide," Journal of Organic Chemistry, vol. 28, pp. 1140-1142, 1963.

Adams, J. et al., "Synthesis of Antimalarials. VI. Synthesis of Certain 1,5-and 1,8-Naphthyridine Derivatives," Journal of the American Chemical Society, vol. 68, pp. 1317-1319, 1946.

Williamson, Thurmond A., "The Chemistry of Quinazoline," Heterocyclic Compounds, vol. 6, pp. 324-376, 1957.

Alonso, F. et al., "Synthesis of 3- and 4-Substituted Cyclic α=Amino Acids Structurally Related to ACPD," Tetrahedron Letters, vol. 51, No. 37, pp. 10259-10280, 1995.

Maguire, R. et al., "Stereoselective Synthesis of cis- and trans-2,6-disubstituted 5,6-dihydro-2H-pyrans based on 1,5-asymmetric induction in reactions between allylstannanes and aldehydes promoted by tin(IV) chloride," Journal of the Royal Society of Chemistry, Perkin Trans. 1, pp. 2487-2495, 1995.

Rosen, T. et al., "Synthetic and biological studies of compactin and related compounds. 2. Synthesis of the lactone moiety of compactin," Journal of Organic Chemistry, vol. 49, pp. 3994-4003, 1984.

Cervi, G. et al., "Bicyclic carbohydrate-derived scaffolds for combinatorial libraries," Bioorganic and Medicinal Chemistry, vol. 14, pp. 3349-3367, 2006.

Kimber, M. et al., "A Preparative and Preliminary Spectroscopic Study of Analogues of a Zinquin-Related Fluorophore," Australian Journal of Chemistry, vol. 56, pp. 39-44, 2003.

French, F. et al., "Carcinostatic activity of thiosemicarbazones of formyl heteroaromatic compounds. VI. 1-Formylisoquinoline derivatives bearing additional ring substituents, with notes on mechanism of action," Journal of Medicinal Chemistry, vol. 13, pp. 1117-1124, 1970.

Kriek, N. et al., "Synthesis of Novel Tetrahydropyran-Based Dipeptide Isosters by Overman Rearrangement of 2,3-Didehydroglycosides," European Journal of Organic Chemistry, pp. 2418-2427, 2003.

Wikler, et al. "Methods for Dilution Antimicrobial Susceptibility Tests for Bacteria That Grow Aerobically", Clinical and Laboratory Standards Institute, Approved Standard—Seventh Edition, vol. 26, No. 2, 2006.

International Search Report (Form PCT/ISA/210) in PCT/IB2007/053472.

Written Opinion of the International Searching Authority (Form PCT/ISA/237) in PCT/IB2007/053472.

\* cited by examiner

SPIRO ANTIBIOTIC DERIVATIVES

CROSS-REFERENCE TO RELATED APPLICATIONS

This application is a national stage of PCT/IB2007/053472, filed on Aug. 29, 2007, which in turn claims priority to PCT/IB2006/053012, filed on Aug. 30, 2006 and PCT/IB2006/054045, filed on Nov. 1, 2006, each of which applications are hereby incorporated by reference in their entirety.

The present invention concerns novel spiro antibiotic derivatives, a pharmaceutical antibacterial composition containing them, the use of these compounds in the manufacture of a medicament for the treatment of infections (e.g. bacterial infections), and methods of treating such infections. These compounds are useful antimicrobial agents effective against a variety of human and veterinary pathogens including among others Gram positive and Gram negative aerobic and anaerobic bacteria and mycobacteria.

BACKGROUND OF THE INVENTION

The intensive use of antibiotics has exerted a selective evolutionary pressure on micro-organisms to produce genetically based resistance mechanisms. Modern medicine and socio-economic behaviour exacerbates the problem of resistance development by creating slow growth situations for pathogenic microbes, e.g. in artificial joints, and by supporting long-term host reservoirs, e.g. in immuno-compromised patients.

In hospital settings, an increasing number of strains of *Staphylococcus aureus, Streptococcus pneumoniae, Enterococcus* spp., and *Pseudomonas aeruginosa*, major sources of infections, are becoming multi-drug resistant and therefore difficult if not impossible to treat:

*S. aureus* is resistant to β-lactams, quinolones and now even to vancomycin;

*S. pneumoniae* is becoming resistant to penicillin or quinolone antibiotics and even to new macrolides;

Enteroccocci are quinolone and vancomycin resistant and β-lactam antibiotics are inefficacious against these strains;

Enterobacteriacea are cephalosporin and quinolone resistant;

*P. aeruginosa* are β-lactam and quinolone resistant.

Further new emerging organisms like *Acinetobacter* spp. or *C. difficile*, which have been selected during therapy with the currently used antibiotics, are becoming a real problem in hospital settings.

In addition, microorganisms that are causing persistent infections are increasingly being recognized as causative agents or cofactors of severe chronic diseases like peptic ulcers or heart diseases.

BRIEF SUMMARY OF THE INVENTION

The invention relates to compounds of formula (I)

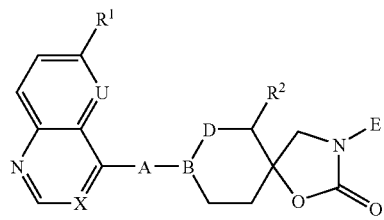

(I)

wherein
$R^1$ represents H, alkyl, alkoxy, cyano or halogen;
one of U and X represents CH or N and the other represents CH, or, in the case of U, may also represent $CR^a$ and, in the case of X, may also represent $CR^b$;
$R^a$ represents halogen;
$R^b$ represents halogen or alkoxy;
B represents N, D represents $CH_2$ and A represents $CH(OH)CH_2$ or $CH_2CH_2$, or
B represents CH, D represents $CH_2$ or O and A represents $OCH_2$, $CH_2CH(OH)$, $CH(OH)CH_2$, $CH(OH)CH(OH)$, $CH=CH$, $CH_2CH_2$ or NHCO, or also
B represents C(OH), D represents $CH_2$ and A represents $OCH_2$, $CH_2CH(OH)$, $CH(OH)CH_2$, $CH(OH)CH(OH)$, $CH=CH$, $CH_2CH_2$ or NHCO;
$R^2$ represents H, alkyl, alkenyl, hydroxyalkyl or alkoxycarbonylalkyl; and
E represents naphthyl or a binuclear heterocyclic group (and in particular a binuclear heterocyclic group);
and to salts of compounds of formula (I).

The following paragraphs provide definitions of the various chemical moieties for the compounds according to the invention and are intended to apply uniformly throughout the specification and claims, unless an otherwise expressly set out definition provides a broader or narrower definition:

The term "alkyl", used alone or in combination, refers to a saturated straight or branched chain alkyl group, containing from one to four carbon atoms. Representative examples of alkyl groups include methyl, ethyl, propyl, iso-propyl, n-butyl, iso-butyl, sec-butyl and tert-butyl. The term "$(C_1-C_x)$alkyl" (x being an integer) refers to a straight or branched chain alkyl group containing 1 to x carbon atoms.

The term "alkoxy", used alone or in combination, refers to a saturated straight or branched chain alkoxy group, containing from one to four carbon atoms. Representative examples of alkoxy groups include methoxy, ethoxy, propoxy, iso-propoxy, n-butoxy, iso-butoxy, sec-butoxy and tert-butoxy. The term "$(C_1-C_x)$alkoxy" refers to a straight or branched chain alkoxy group containing 1 to x carbon atoms.

The term "halogen" refers to fluorine, chlorine, bromine or iodine, preferably to fluorine or chlorine.

The term "alkenyl" refers to a straight or branched hydrocarbon chain containing 2 to 4 carbon atoms with at least one carbon-carbon double bond. Representative examples of alkenyl include, but are not limited to, ethenyl and 2-propenyl (and notably 2-propenyl).

The term "hydroxyalkyl" refers to a saturated straight or branched chain alkyl group substituted once by hydroxy and containing from one to four carbon atoms. Representative examples of hydroxyalkyl include, but are not limited to, hydroxymethyl and 2-hydroxyethyl.

The term "alkoxycarbonylalkyl" refers to a saturated straight or branched chain alkyl group containing from one to four carbon atoms, which alkyl group is substituted once by an alkoxycarbonyl group wherein the alkoxy group is a saturated straight or branched chain alkoxy group containing from one to four carbon atoms. Representative examples of alkoxycarbonylalkyl include, but are not limited to, methoxycarbonylmethyl.

The term "binuclear heterocyclic group" refers to a benzene or pyridine ring fused with a 1,4-dioxane unit, a 1,3-dioxolane unit, a morpholine-3-one unit or a thiomorpholine-3-one unit. A "binuclear heterocyclic group" containing a benzene ring may be substituted on said benzene ring by a halogen atom (said halogen atom being preferably a fluorine atom). Thus, representative examples of binuclear heterocyclic groups include, but are not limited to, 2,3-dihydro-benzo[1,4]dioxin-6-yl, benzo[1,3]dioxol-5-yl, 3-oxo-3,4-dihydro-2H-benzo[1,4]oxazine-6-yl, 3-oxo-3,4-dihydro-2H-benzo[1,4]thiazine-6-yl, 7-fluoro-3-oxo-3,4-dihydro-2H-benzo[1,4]thiazine-6-yl, 2,3-dihydro-[1,4]dioxino[2,3-c]pyridine-7-yl and 3-oxo-3,4-dihydro-2H-pyrido[3,2-b][1,4]thiazine-6-yl.

When in the formula

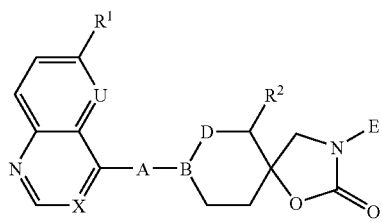

A represents the radical $OCH_2$, this means specifically that the oxygen atom of the $OCH_2$ radical is attached to the bicyclic ring system bearing the $R^1$ group and that the $CH_2$ group of the $OCH_2$ radical is attached to the B group. This is applicable mutatis mutandis to all radicals that make the A radical. In other words, the left part of a radical is always attached to the right part of the radical that is next to the left.

Moreover, the sign "*" placed near an atom will be used to designate the point of attachment of a radical to the rest of a molecule. For example:

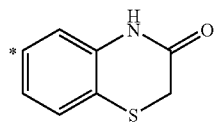

designates the 3-oxo-3,4-dihydro-2H-benzo[1,4]thiazine-6-yl radical.

In particular, the invention relates to compounds of formula (I) that are also compounds of formula ($I_{CE}$)

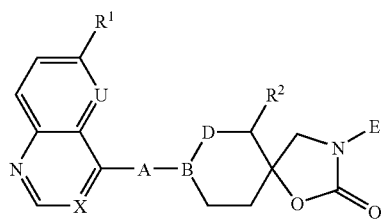

(I_{CE})

wherein
$R^1$ represents alkoxy (in particular methoxy);
U represents N and X represents CH, or each of U and X represents CH, or also each of U represents CH and X represents N;
B represents N, D represents $CH_2$ and A represents $CH(OH)CH_2$, or
B represents CH, D represents $CH_2$ and A represents $OCH_2$, $CH(OH)CH(OH)$, $CH=CH$ or NHCO, or B represents CH, D represents O and A represents $CH(OH)CH_2$, or also
B represents C(OH), D represents $CH_2$ and A represents $CH_2CH_2$;
$R^2$ represents H, alkenyl, hydroxyalkyl or alkoxycarbonylalkyl; and
E represents a binuclear heterocyclic group;
and to salts of compounds of formula ($I_{CE}$).

Preferably, the compounds of formula ($I_{CE}$) will have at least one of the following characteristics:
$R^1$ represents ($C_1$-$C_3$)alkoxy (in particular methoxy);
$R^2$ represents H or alkenyl (notably H or allyl and in particular H);
E represents a binuclear heterocyclic group of the formula

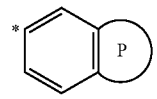

wherein the ring P is selected from the following

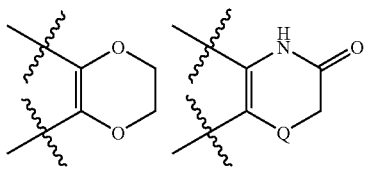

in which Q is O or S.

Preferred compounds of formula (I) are those wherein at least one of the following characteristics is present:
$R^1$ represents ($C_1$-$C_3$)alkyl, ($C_1$-$C_3$)alkoxy or cyano;
$R^2$ represents H, alkyl, alkenyl or hydroxyalkyl;
U represents N and X represents CH, or each of U and X represents CH, or also U represents CH and X represents N;
B represents N, D represents $CH_2$ and A represents $CH(OH)CH_2$, or
B represents CH, D represents $CH_2$ and A represents $OCH_2$, $CH_2CH_2$, $CH=CH$ or NHCO, or
B represents CH, D represents O and A represents $CH(OH)CH_2$, or also
B represents C(OH), D represents $CH_2$ and A represents $CH_2CH_2$;
E represents a binuclear heterocyclic group of the formula

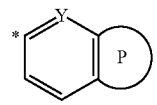

wherein

Y is CH or N, and the ring P is selected from the following

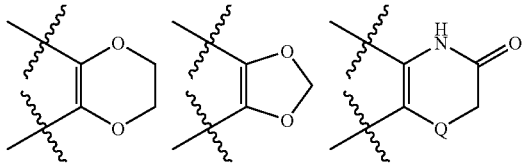

in which Q is O or S.

More preferred compounds of formula (I) are those wherein at least one of the following characteristics is present:

$R^1$ represents $(C_1-C_3)$alkoxy;

$R^2$ represents H or alkenyl;

B represents N, D represents $CH_2$ and A represents $CH(OH)CH_2$, or

B represents CH, D represents $CH_2$ and A represents $OCH_2$, $CH_2CH_2$, $CH=CH$ or NHCO, or B represents C(OH), D represents $CH_2$ and A represents $CH_2CH_2$;

E represents a binuclear heterocyclic group of the formula

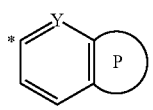

wherein

Y is CH or N, and the ring P is selected from the following

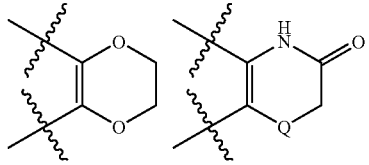

in which Q is O or S.

Particularly preferred compounds of formula (I) are those wherein at least one of the following characteristics is present:

$R^1$ represents methoxy or ethoxy (and in particular methoxy);

$R^2$ represents H;

E represents a binuclear heterocyclic group of the formula

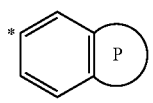

wherein the ring P is selected from the following

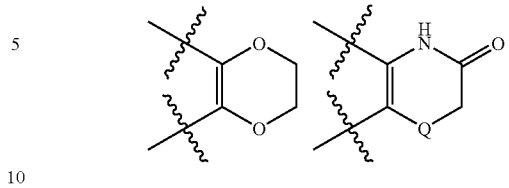

in which Q is O or S.

According to a first variant of this invention, the compounds of formula (I) will be such that both U and X represent CH.

According to a second variant of this invention, the compounds of formula (I) will be such that U represents N and X represents CH.

According to a third variant of this invention, the compounds of formula (I) will be such that U represents CH and X represents N.

In a general manner, the compounds of formula (I) wherein both U and X represent CH or U represents N and X represents CH will be preferred.

Moreover, compounds of general formula (I) or $(I_{CE})$ wherein E represents 2,3-dihydro-benzo[1,4]dioxin-6-yl, 3-oxo-3,4-dihydro-2H-benzo[1,4]oxazine-6-yl or 3-oxo-3,4-dihydro-2H-benzo[1,4]thiazine-6-yl will be particularly preferred.

The following main embodiments of compounds of formula (I) (or of salts thereof, in particular of pharmaceutically acceptable salts thereof) will be equally preferred.

According to a first main embodiment of this invention, the compounds of formula I will be such that B represents N; such compounds will be collectively designated by "compounds of formula $(I_N)$" throughout the specification and claims.

According to a second main embodiment of this invention, the compounds of formula I will be such that B represents CH; such compounds will be collectively designated by "compounds of formula $(I_{CH})$" throughout the specification and claims.

Compounds of formula $(I_{CH})$ will preferably be such that they correspond to the following configuration:

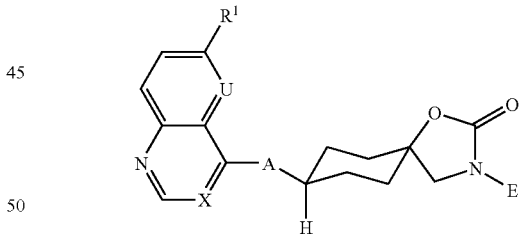

According to a third main embodiment of this invention, the compounds of formula I will be such that B represents C(OH); such compounds will be collectively designated by "compounds of formula $(I_{COH})$" throughout the specification and claims.

Especially preferred are the following compounds of formula (I):

(5R,6R,8S)-3-(2,3-dihydro-benzo[1,4]dioxin-6-yl)-8-[(2R)-2-hydroxy-2-(6-methoxy-[1,5]naphthyridin-4-yl)-ethyl]-6-hydroxymethyl-1,7-dioxa-3-aza-spiro[4.5]decan-2-one;

(5R,6R,8S)-3-(2,3-dihydro-benzo[1,4]dioxin-6-yl)-8-[(2S)-2-hydroxy-2-(6-methoxy-[1,5]naphthyridin-4-yl)-ethyl]-6-hydroxymethyl-1,7-dioxa-3-aza-spiro[4.5]decan-2-one;

cis-3-(2,3-dihydro-benzo[1,4]dioxin-6-yl)-8-(6-methoxy-quinolin-4-yloxymethyl)-1-oxa-3-aza-spiro[4.5]decan-2-one;

cis-3-(2,3-dihydro-benzo[1,4]dioxin-6-yl)-8-(6-methoxy-[1,5]naphthyridin-4-yloxymethyl)-1-oxa-3-aza-spiro[4.5]decan-2-one;

3-(2,3-dihydro-benzo[1,4]dioxin-6-yl)-8-[(2R)-2-hydroxy-2-(6-methoxy-quinolin-4-yl)-ethyl]-1-oxa-3,8-diaza-spiro[4.5]decan-2-one;

3-(2,3-dihydro-benzo[1,4]dioxin-6-yl)-8-[(2S)-2-hydroxy-2-(6-methoxy-quinolin-4-yl)-ethyl]-1-oxa-3,8-diaza-spiro[4.5]decan-2-one;

6-{8-[(2R)-2-hydroxy-2-(6-methoxy-quinolin-4-yl)-ethyl]-2-oxo-1-oxa-3,8-diaza-spiro[4.5]dec-3-yl}-4H-benzo[1,4]thiazin-3-one;

6-{8-[(2S)-2-hydroxy-2-(6-methoxy-quinolin-4-yl)-ethyl]-2-oxo-1-oxa-3,8-diaza-spiro[4.5]dec-3-yl}-4H-benzo[1,4]thiazin-3-one;

(5R,6R)-6-allyl-3-(2,3-dihydro-benzo[1,4]dioxin-6-yl)-8-[(2R)-2-hydroxy-2-(6-methoxy-quinolin-4-yl)-ethyl]-1-oxa-3,8-diaza-spiro[4.5]decan-2-one;

(5R,6R)-6-allyl-3-(2,3-dihydro-benzo[1,4]dioxin-6-yl)-8-[(2S)-2-hydroxy-2-(6-methoxy-quinolin-4-yl)-ethyl]-1-oxa-3,8-diaza-spiro[4.5]decan-2-one;

(5R,6S)-6-allyl-3-(2,3-dihydro-benzo[1,4]dioxin-6-yl)-8-[(2R)-2-hydroxy-2-(6-methoxy-quinolin-4-yl)-ethyl]-1-oxa-3,8-diaza-spiro[4.5]decan-2-one;

(5R,6S)-6-allyl-3-(2,3-dihydro-benzo[1,4]dioxin-6-yl)-8-[(2S)-2-hydroxy-2-(6-methoxy-quinolin-4-yl)-ethyl]-1-oxa-3,8-diaza-spiro[4.5]decan-2-one;

(5S,6R)-6-allyl-3-(2,3-dihydro-benzo[1,4]dioxin-6-yl)-8-[(2R)-2-hydroxy-2-(6-methoxy-quinolin-4-yl)-ethyl]-1-oxa-3,8-diaza-spiro[4.5]decan-2-one;

(5S,6R)-6-allyl-3-(2,3-dihydro-benzo[1,4]dioxin-6-yl)-8-[(2S)-2-hydroxy-2-(6-methoxy-quinolin-4-yl)-ethyl]-1-oxa-3,8-diaza-spiro[4.5]decan-2-one;

(5S,6S)-6-allyl-3-(2,3-dihydro-benzo[1,4]dioxin-6-yl)-8-[(2R)-2-hydroxy-2-(6-methoxy-quinolin-4-yl)-ethyl]-1-oxa-3,8-diaza-spiro[4.5]decan-2-one;

(5S,6S)-6-allyl-3-(2,3-dihydro-benzo[1,4]dioxin-6-yl)-8-[(2S)-2-hydroxy-2-(6-methoxy-quinolin-4-yl)-ethyl]-1-oxa-3,8-diaza-spiro[4.5]decan-2-one;

(5R,6R)-{3-(2,3-dihydro-benzo[1,4]dioxin-6-yl)-8-[(2R)-2-hydroxy-2-(6-methoxy-quinolin-4-yl)-ethyl]-2-oxo-1-oxa-3,8-diaza-spiro[4.5]dec-6-yl}-acetic acid methyl ester;

(5R,6R)-{3-(2,3-dihydro-benzo[1,4]dioxin-6-yl)-8-[(2S)-2-hydroxy-2-(6-methoxy-quinolin-4-yl)-ethyl]-2-oxo-1-oxa-3,8-diaza-spiro[4.5]dec-6-yl}-acetic acid methyl ester;

(5R,6S)-{3-(2,3-dihydro-benzo[1,4]dioxin-6-yl)-8-[(2R)-2-hydroxy-2-(6-methoxy-quinolin-4-yl)-ethyl]-2-oxo-1-oxa-3,8-diaza-spiro[4.5]dec-6-yl}-acetic acid methyl ester;

(5R,6S)-{3-(2,3-dihydro-benzo[1,4]dioxin-6-yl)-8-[(2S)-2-hydroxy-2-(6-methoxy-quinolin-4-yl)-ethyl]-2-oxo-1-oxa-3,8-diaza-spiro[4.5]dec-6-yl}-acetic acid methyl ester;

(5S,6R)-{3-(2,3-dihydro-benzo[1,4]dioxin-6-yl)-8-[(2R)-2-hydroxy-2-(6-methoxy-quinolin-4-yl)-ethyl]-2-oxo-1-oxa-3,8-diaza-spiro[4.5]dec-6-yl}-acetic acid methyl ester;

(5S,6R)-{3-(2,3-dihydro-benzo[1,4]dioxin-6-yl)-8-[(2S)-2-hydroxy-2-(6-methoxy-quinolin-4-yl)-ethyl]-2-oxo-1-oxa-3,8-diaza-spiro[4.5]dec-6-yl}-acetic acid methyl ester;

(5S,6S)-{3-(2,3-dihydro-benzo[1,4]dioxin-6-yl)-8-[(2R)-2-hydroxy-2-(6-methoxy-quinolin-4-yl)-ethyl]-2-oxo-1-oxa-3,8-diaza-spiro[4.5]dec-6-yl}-acetic acid methyl ester;

(5S,6S)-{3-(2,3-dihydro-benzo[1,4]dioxin-6-yl)-8-[(2S)-2-hydroxy-2-(6-methoxy-quinolin-4-yl)-ethyl]-2-oxo-1-oxa-3,8-diaza-spiro[4.5]dec-6-yl}-acetic acid methyl ester;

(5R,6R)-3-(2,3-dihydro-benzo[1,4]dioxin-6-yl)-6-(2-hydroxyethyl)-8-[(2R)-2-hydroxy-2-(6-methoxy-quinolin-4-yl)-ethyl]-1-oxa-3,8-diaza-spiro[4.5]decan-2-one;

(5R,6R)-3-(2,3-dihydro-benzo[1,4]dioxin-6-yl)-6-(2-hydroxy-ethyl)-8-[(2S)-2-hydroxy-2-(6-methoxy-quinolin-4-yl)-ethyl]-1-oxa-3,8-diaza-spiro[4.5]decan-2-one;

(5R,6S)-3-(2,3-dihydro-benzo[1,4]dioxin-6-yl)-6-(2-hydroxy-ethyl)-8-[(2R)-2-hydroxy-2-(6-methoxy-quinolin-4-yl)-ethyl]-1-oxa-3,8-diaza-spiro[4.5]decan-2-one;

(5R,6S)-3-(2,3-dihydro-benzo[1,4]dioxin-6-yl)-6-(2-hydroxy-ethyl)-8-[(2S)-2-hydroxy-2-(6-methoxy-quinolin-4-yl)-ethyl]-1-oxa-3,8-diaza-spiro[4.5]decan-2-one;

(5S,6R)-3-(2,3-dihydro-benzo[1,4]dioxin-6-yl)-6-(2-hydroxy-ethyl)-8-[(2R)-2-hydroxy-2-(6-methoxy-quinolin-4-yl)-ethyl]-1-oxa-3,8-diaza-spiro[4.5]decan-2-one;

(5S,6R)-3-(2,3-dihydro-benzo[1,4]dioxin-6-yl)-6-(2-hydroxy-ethyl)-8-[(2S)-2-hydroxy-2-(6-methoxy-quinolin-4-yl)-ethyl]-1-oxa-3,8-diaza-spiro[4.5]decan-2-one;

(5S,6S)-3-(2,3-dihydro-benzo[1,4]dioxin-6-yl)-6-(2-hydroxy-ethyl)-8-[(2R)-2-hydroxy-2-(6-methoxy-quinolin-4-yl)-ethyl]-1-oxa-3,8-diaza-spiro[4.5]decan-2-one;

(5S,6S)-3-(2,3-dihydro-benzo[1,4]dioxin-6-yl)-6-(2-hydroxy-ethyl)-8-[(2S)-2-hydroxy-2-(6-methoxy-quinolin-4-yl)-ethyl]-1-oxa-3,8-diaza-spiro[4.5]decan-2-one;

cis-3-(2,3-dihydro-benzo[1,4]dioxin-6-yl)-2-oxo-1-oxa-3-aza-spiro[4.5]decane-8-carboxylic acid (6-methoxy-[1,5]naphthyridin-4-yl)-amide;

trans-3-(2,3-dihydro-benzo[1,4]dioxin-6-yl)-2-oxo-1-oxa-3-aza-spiro[4.5]decane-8-carboxylic acid (6-methoxy-[1,5]naphthyridin-4-yl)-amide;

cis-3-(2,3-dihydro-benzo[1,4]dioxin-6-yl)-8-hydroxy-8-[2-(6-methoxy-[1,5]naphthyridin-4-yl)-ethyl]-1-oxa-3-aza-spiro[4.5]decan-2-one;

trans-3-(2,3-dihydro-benzo[1,4]dioxin-6-yl)-8-hydroxy-8-[2-(6-methoxy-[1,5]naphthyridin-4-yl)-ethyl]-1-oxa-3-aza-spiro[4.5]decan-2-one;

cis-6-{8-hydroxy-8-[2-(6-methoxy-[1,5]naphthyridin-4-yl)-ethyl]-2-oxo-1-oxa-3-aza-spiro[4.5]dec-3-yl}-4H-benzo[1,4]thiazin-3-one;

trans-6-{8-hydroxy-8-[2-(6-methoxy-[1,5]naphthyridin-4-yl)-ethyl]-2-oxo-1-oxa-3-aza-spiro[4.5]dec-3-yl}-4H-benzo[1,4]thiazin-3-one;

cis-6-{8-hydroxy-8-[2-(6-methoxy-[1,5]naphthyridin-4-yl)-ethyl]-2-oxo-1-oxa-3-aza-spiro[4.5]dec-3-yl}-4H-benzo[1,4]oxazin-3-one;

trans-6-{8-hydroxy-8-[2-(6-methoxy-[1,5]naphthyridin-4-yl)-ethyl]-2-oxo-1-oxa-3-aza-spiro[4.5]dec-3-yl}-4H-benzo[1,4]oxazin-3-one;

cis-6-{8-[2-(6-methoxy-[1,5]naphthyridin-4-yl)-ethyl]-2-oxo-1-oxa-3-aza-spiro[4.5]dec-3-yl}-4H-benzo[1,4]oxazin-3-one;

trans-6-{8-[2-(6-methoxy-[1,5]naphthyridin-4-yl)-ethyl]-2-oxo-1-oxa-3-aza-spiro[4.5]dec-3-yl}-4H-benzo[1,4]oxazin-3-one;

cis-3-(2,3-dihydro-benzo[1,4]dioxin-6-yl)-8-[(E)-2-(6-methoxy-quinolin-4-yl)-vinyl]-1-oxa-3-aza-spiro[4.5]decan-2-one;

trans-3-(2,3-dihydro-benzo[1,4]dioxin-6-yl)-8-[(E)-2-(6-methoxy-quinolin-4-yl)-vinyl]-1-oxa-3-aza-spiro[4.5]decan-2-one;

cis-6-{8-[(E)-2-(6-methoxy-quinolin-4-yl)-vinyl]-2-oxo-1-oxa-3-aza-spiro[4.5]dec-3-yl}-4H-benzo[1,4]thiazin-3-one;

trans-6-{8-[(E)-2-(6-methoxy-quinolin-4-yl)-vinyl]-2-oxo-1-oxa-3-aza-spiro[4.5]dec-3-yl}-4H-benzo[1,4]thiazin-3-one;

cis-3-(2,3-dihydro-benzo[1,4]dioxin-6-yl)-8-(6-methoxy-quinazolin-4-yloxymethyl)-1-oxa-3-aza-spiro[4.5]decan-2-one;

and salts (in particular pharmaceutically acceptable salts) thereof.

DETAILED DESCRIPTION OF THE INVENTION

Compounds of formula (I) are suitable for the use as chemotherapeutic active compounds in human and veterinary medicine and as substances for preserving inorganic and organic materials in particular all types of organic materials for example polymers, lubricants, paints, fibres, leather, paper and wood.

These compounds according to the invention are particularly active against bacteria and bacteria-like organisms. They are therefore particularly suitable in human and veterinary medicine for the prophylaxis and chemotherapy of local and systemic infections caused by these pathogens as well as disorders related to bacterial infections comprising pneumonia, otitis media, sinusitis, bronchitis, tonsillitis, and mastoiditis related to infection by *Streptococcus pneumoniae, Haemophilus influenzae, Moraxella catarrhalis, Staphylococcus aureus, Enterococcus faecalis, E. faecium, E. casseliflavus, S. epidermidis, S. haemolyticus*, or *Peptostreptococcus* spp.; pharyngitis, rheumatic fever, and glomerulonephritis related to infection by *Streptococcus pyogenes*, Groups C and G streptococci, *Corynebacterium diphtheriae*, or *Actinobacillus haemolyticum*; respiratory tract infections related to infection by *Mycoplasma pneumoniae, Legionella pneumophila, Streptococcus pneumoniae, Haemophilus influenzae*, or *Chlamydia pneumoniae*; blood and tissue infections, including endocarditis and osteomyelitis, caused by *S. aureus, S. haemolyticus, E. faecalis, E. faecium, E. durans*, including strains resistant to known antibacterials such as, but not limited to, beta-lactams, vancomycin, aminoglycosides, quinolones, chloramphenicol, tetracyclines and macrolides; uncomplicated skin and soft tissue infections and abscesses, and puerperal fever related to infection by *Staphylococcus aureus*, coagulase-negative staphylococci (i.e., *S. epidermidis, S. haemolyticus*, etc.), *Streptococcus pyogenes, Streptococcus agalactiae*, Streptococcal groups C-F (minute colony streptococci), viridans streptococci, *Corynebacterium minutissimum, Clostridium* spp., or *Bartonella henselae*; uncomplicated acute urinary tract infections related to infection by *Staphylococcus aureus*, coagulase-negative staphylococcal species, or *Enterococcus* spp.; urethritis and cervicitis; sexually transmitted diseases related to infection by *Chlamydia trachomatis, Haemophilus ducreyi, Treponema pallidum, Ureaplasma urealyticum*, or *Neiserria gonorrheae*; toxin diseases related to infection by *S. aureus* (food poisoning and toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae*, or *Listeria* spp.; disseminated *Mycobacterium avium* complex (MAC) disease related to infection by *Mycobacterium aviuma*, or *Mycobacterium intracellulare*; infections caused by *Mycobacterium tuberculosis, M. leprae, M. paratuberculosis, M. kansasii*, or *M. chelonei*; gastroenteritis related to infection by *Campylobacter jejuni*; intestinal protozoa related to infection by *Cryptosporidium* spp.; odontogenic infection related to infection by viridans streptococci; persistent cough related to infection by *Bordetella pertussis*; gas gangrene related to infection by *Clostridium perfringens* or *Bacteroides* spp.; and atherosclerosis or cardiovascular disease related to infection by *Helicobacter pylori* or *Chlamydia pneumoniae*.

Compounds of formula (I) according to the present invention are further useful for the preparation of a medicament for the treatment of infections that are mediated by bacteria such as *E. coli, Klebsiella pneumoniae* and other Enterobacteriaceae, *Acinetobacter* spp., *Stenothrophomonas maltophilia, Neisseria meningitidis, Bacillus cereus, Bacillus anthracis, Corynebacterium* spp., *Propionibacterium acnes* and *Bacteroide* spp.

Compounds of formula (I) according to the present invention are further useful to treat protozoal infections caused by *Plasmodium malaria, Plasmodium falciparum, Toxoplasma gondii, Pneumocystis carinii, Trypanosoma brucei* and *Leishmania* spp.

The present list of pathogens is to be interpreted merely as examples and in no way as limiting.

One aspect of this invention therefore relates to the use of a compound of formula (I) according to this invention, or of a pharmaceutically acceptable salt thereof, for the manufacture of a medicament for the prevention or treatment of a bacterial infection.

As well as in humans, bacterial infections can also be treated using compounds of formula (I) (or pharmaceutically acceptable salts thereof) in other species like pigs, ruminants, horses, dogs, cats and poultry.

The present invention also relates to pharmacologically acceptable salts and to compositions and formulations of compounds of formula (I).

Any reference to a compound of formula (I) is to be understood as referring also to the salts (and especially the pharmaceutically acceptable salts) of such compounds, as appropriate and expedient.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

A pharmaceutical composition according to the present invention contains at least one compound of formula (I) (or a pharmaceutically acceptable salt thereof) as the active agent and optionally carriers and/or diluents and/or adjuvants, and may also contain additional known antibiotics.

As mentioned above, therapeutically useful agents that contain compounds of formula (I), their salts and formulations thereof are also comprised in the scope of the present invention. In general, compounds of formula (I) will be administered by using the known and acceptable modes known in the art, either alone or in combination with any other therapeutic agent. Such therapeutically useful agents can be administered by one of the following routes: oral, e.g. as tablets, dragee, coated tablets, pills, semisolids, soft or hard capsules, for example soft and hard gelatine capsules, aqueous or oily solutions, emulsions, suspensions or syrups, parenteral including intravenous, intramuscular and subcutaneous injection, e.g. as an injectable solution or suspension, rectal as suppositories, by inhalation or insufflation, e.g. as a powder formulation, as microcrystal or as a spray (e.g. liquid aerosol), transdermal, for example via an transdermal delivery system (TDS) such as a plaster containing the active ingredient, topical or intranasal. The substance of the present invention can also be used to impregnate or coated devices that are foreseen for implantation like catheters or artificial joints. The pharmaceutically useful agents may also contain additives for conservation, stabilisation, e.g. UV stabilizers, emulsifiers, sweetener, aromatisers, salts to change the osmotic pressure, buffers, coating additives and antioxidants.

Another aspect of the invention concerns a method for the prevention or the treatment of a bacterial infection in a patient comprising the administration to said patient of a pharmaceutically active amount of a derivative according to formula (I) or a pharmaceutically acceptable salt thereof.

Besides, any preferences indicated for the compounds of formula (I) (whether for the compounds themselves, salts thereof, compositions containing the compounds or salts thereof, uses of the compounds or salts thereof, etc.) apply mutatis mutandis to compounds of formula ($I_{CE}$), compounds of formula ($I_N$), compounds of formula ($I_{CH}$) and compounds of formula ($I_{COH}$).

Moreover, the compounds of formula (I) may also be used for cleaning purposes, e.g. to remove pathogenic microbes and bacteria from surgical instruments or to make a room or an area aseptic. For such purposes, the compounds of formula (I) could be contained in a solution or in a spray formulation.

The compounds of formula (I) can be manufactured in accordance with the present invention using the procedures described hereafter.

Preparation of Compounds of Formula (I)
Abbreviations:
The following abbreviations are used throughout the specification and the examples:

| | |
|---|---|
| AcOH | acetic acid |
| AD-mix α | 1,4-bis(dihydroquinine)phthalazine, $K_3Fe(CN)_6$, $K_2CO_3$ and $K_2OsO_4 \cdot 2H_2O$ |
| AD-mix β | 1,4-bis(dihydroquinidine)phthalazine, $K_3Fe(CN)_6$, $K_2CO_3$ and $K_2OsO_4 \cdot 2H_2O$ |
| aq. | aqueous |
| Bn | benzyl |
| DCC | N,N'-dicyclohexylcarbodiimide |
| 1,2-DCE | 1,2-dichloroethane |
| DCM | dichloromethane |
| DEAD | diethyl azodicarboxylate |
| DIAD | diisopropyl azodicarboxylate |
| DIBAH | diisobutylaluminium hydride |
| DIPEA | N,N-diisopropylethylamine |
| DMAP | 4-dimethylaminopyridine |
| 1,2-DME | 1,2-dimethoxyethane |
| DMF | N,N-dimethylformamide |
| DMSO | dimethylsulfoxide |
| DMPU | 1,3-dimethyl-3,4,5,6-tetrahydro-2(1H)-pyrimidone |
| EA | ethyl acetate |
| EDC | 1-(3-dimethylaminopropyl)-3-ethylcarbodiimide hydrochloride |
| ESI | Electron Spray Ionisation |
| Ether | diethyl ether |
| EtOH | ethanol |
| h | hour |
| HATU | O-(7-azabenzotriazol-1-yl)-N,N,N',N'-tetramethyluronium hexafluorophosphate |
| Hex | hexane |
| HMPT | hexamethylphosphorous triamide |
| HOBT | 1-hydroxybenzotriazole hydrate |
| HV | high vacuum conditions |
| KHMDS | potassium hexamethyldisilazide |
| KOtBu | potassium tert-butoxide |
| LC | Liquid Chromatography |
| LDA | lithium diisopropylamide |
| LiHMDS | lithium hexamethyldisilazide |

-continued

| | |
|---|---|
| MCPBA | meta-chloroperbenzoic acid |
| MeCN | acetonitrile |
| MeOH | methanol |
| min | minutes |
| MS | Mass Spectroscopy |
| MsCl | methanesulfonyl chloride |
| org. | organic |
| Pd/C | palladium on carbon |
| PTSA | para-toluenesulfonic acid |
| sat. | saturated |
| TBDMS | tert-butyldimethylsilyl |
| TBDPS | tert-butyldiphenylsilyl |
| TEA | triethyl amine |
| Tf | triflyl (=trifluoromethanesulfonyl) |
| TFA | trifluoroacetic acid |
| THF | tetrahydrofuran |
| Ts | tosyl |
| p-TsCl | para-toluenesulfonyl chloride |
| rt | room temperature |

General Preparation Methods:

Sections a) to n) hereafter describe general methods for preparing compounds of formula (I).

a) The compounds of formula (I) can be manufactured in accordance with the present invention by reacting a compound of the formula (II)

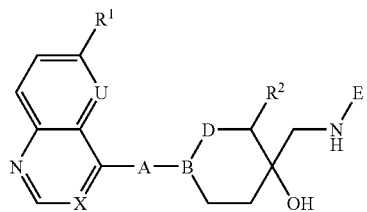

(II)

wherein $R^1$, $R^2$, U, X, A, B, D and E are as defined in formula (I), with a compound of formula (III)

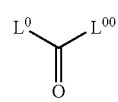

(III)

wherein $L^0$ and $L^{00}$ are both halogen, $OCCl_3$, imidazolyl or succinimidyloxy, or $L^0$ is halogen and $L^{00}$ is $OCCl_3$.

This reaction is preferably carried out in a dry aprotic solvent such as DCM or THF in presence of an organic base such as TEA or pyridine and at a temperature between −30° and +40° C.

b) Compounds of formula (I) wherein A is CH(OH)CH$_2$, B is N and D is CH$_2$ can be manufactured by reacting a compound of the formula (IV)

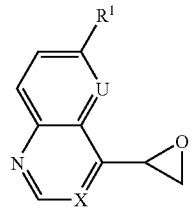
(IV)

wherein R$^1$, U, and X are as defined in formula (I), with a compound of formula (V)

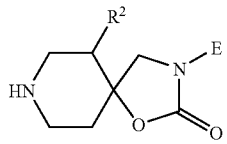
(V)

wherein E and R$^2$ are as defined in formula (I).

The reaction between the epoxide derivative of formula (IV) and the piperidine derivative of formula (V) is preferably carried out in a polar solvent such as DMF at a temperature between 40 and 100° C. and in presence of an alkali carbonate (such as potassium carbonate) and a lithium salt (such as lithium perchlorate).

c) Compounds of formula (I) wherein U and X are as defined in formula (I), A is OCH$_2$, D is O or CH$_2$ and B is CH can be manufactured by reacting a compound of the formula (VI)

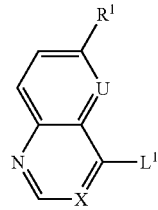
(VI)

wherein L$^1$ is OH and R$^1$, U and X are as defined in formula (I), with a compound of formula (VII)

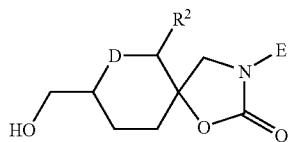
(VII)

wherein D, R$^2$ and E are as defined in formula (I).

This reaction is performed under Mitsunobu conditions (as reviewed in O. Mitsunobu, *Synthesis* (1981), 1), i.e. in the presence of DEAD or DIAD and PPh$_3$. The reaction may be performed in a wide range of solvents such as DMF, THF, or DCM and at a wide range of temperatures (between −78° C. and 50° C.).

An alternate route to compounds of formula (I) may require the activation of the alcohol of formula (VII) as for example a tosylate, a triflate or a mesylate by treatment with TsCl, trifluoromethanesulphonic anhydride or MsCl respectively in the presence of an organic base such as TEA between −40° C. and 60° C. in a dry aprotic solvent like DCM, MeCN or THF. Once activated, alcohol of formula (VII) reacts with the derivative of the compound of formula (VI) wherein L$^1$=O$^−$, generated with an inorganic base such as NaH or K$_2$CO$_3$ or with an organic base such as LiHMDS between −20° C. and 60° C.

Compounds of formula (I) wherein U and X are as defined in formula (I), A is OCH$_2$, D is or CH$_2$ and B is CH can also be manufactured by reacting a compound of the formula (VIa)

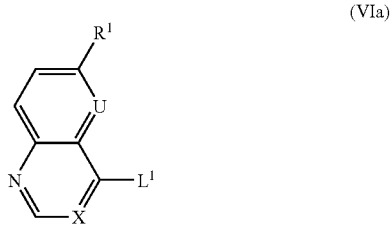
(VIa)

wherein L$^1$ is halogen and R$^1$, U and X are as defined in formula (I),
with a compound of formula (VII)

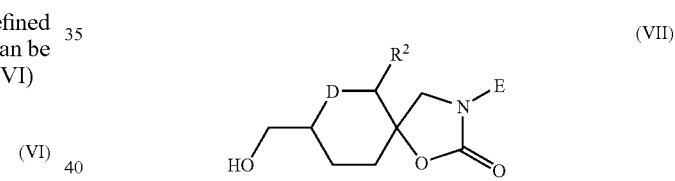
(VII)

wherein D, R$^2$ and E are as defined in formula (I).

This reaction is performed with the sodium or lithium salt of compound of formula (VII) generated in presence of metal hydride such NaH between −20° C. and 60° C. in a dry aprotic solvent like DMF, MeCN or THF and in presence of a copper (I) salt such as CuI if necessary.

d) Compounds of formula (I) wherein U and X are as defined in formula (I), except however the case wherein X is N and U is CH, and wherein further A is NHCO, D is CH$_2$ or O and B is CH can be manufactured by reacting a compound of the formula (VIII)

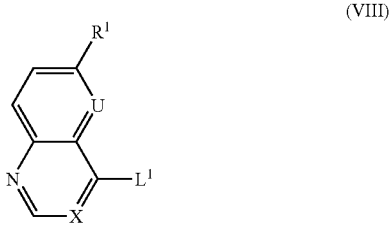
(VIII)

wherein L¹ is NH₂ and R¹, U and X are as defined in formula (I), except however the cases wherein X is N and U is CH, with a compound of formula (IX)

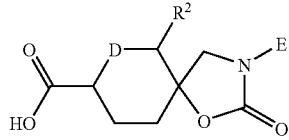
(IX)

wherein D, R² and E are as defined in formula (I).

The reaction between the aniline derivative of formula (VIII) and the cyclohexanecarboxylic acid derivative of formula (IX) is preferably carried out in presence of an activating agent such as DCC, EDC, HOBT, HATU or di-(N-succinimidyl)-carbonate, in a dry aprotic solvent such as DCM, MeCN or DMF between −20° C. and 60° C. (see G. Benz in *Comprehensive Organic Synthesis*, B. M. Trost, I. Fleming, Eds; Pergamon Press: New York (1991), vol. 6, p. 381). Alternatively, the carboxylic acid can be activated by conversion into its corresponding acid chloride by reaction with oxalyl chloride or thionyl chloride neat or in a solvent like DCM between −20° and 60° C.

e) Compounds of formula (I) wherein U and X are as defined in formula (I), A is NHCO, D is CH₂ or O and B is CH can be manufactured by reacting either a compound of formula (VIa) as defined previously or a compound of the formula (X)

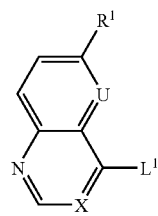
(X)

wherein L¹ is trifluoromethanesulfonyl and R¹, U and X are as defined in formula (I), with a compound of formula (XI)

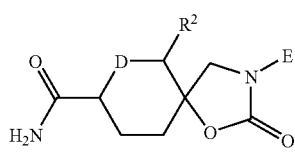
(XI)

wherein D, R² and E are as defined in formula (I).

This reaction is carried out under palladium-catalyzed Buchwald-Hartwig conditions (*J. Am. Chem. Soc.* (1996), 118, 10333) or copper-catalyzed conditions (*J. Am. Chem. Soc.* (2002), 124, 7421). Various palladium sources and ligands may be used, as well as a variety of solvents, including (for example) dioxane and toluene.

f) Compounds of formula (I) wherein A is CHOHCHOH, D is CH₂ or O and B is CH can be manufactured by cis-dihydroxylation a compound of the formula (XII)

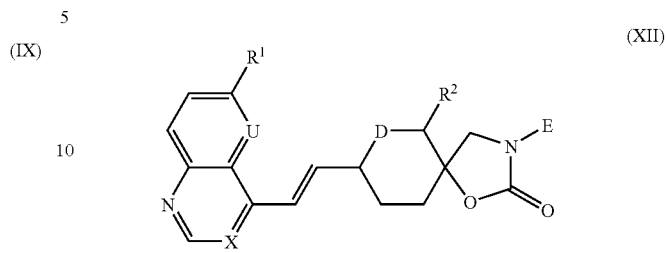
(XII)

wherein R¹, U, X, R² and E are as defined in formula (I) by treatment with AD-mix α or AD-mix β in presence of methanesulfonamide in a water/2-methyl-2-propanol mixture as described in *Chem. Rev.* (1994), 94, 2483. The sense of induction relies on the chiral ligand contained in the AD mixture, either a dihydroquinine-based ligand in AD-mix α or a dihydroquinidine-based ligand in AD-mix β.

g) Compounds of formula (I) wherein A is CHOHCH₂, and either D is O and B is CH or D is CH₂ and B is CH or C(OH) can be manufactured by reacting a compound of the formula (XIII)

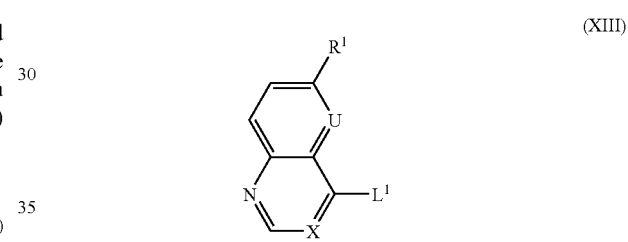
(XIII)

wherein L¹ is L¹ and R¹, U and X are as defined in formula (I), with a compound of formula (XIV)

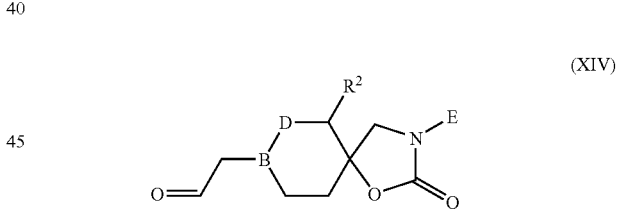
(XIV)

wherein B is CH or C(OH), D, R² and E are as defined in formula (I) in a dry solvent such as THF or ether and at a temperature between −78° C. and 20° C.

h) Compounds of formula (I) wherein U and X are as defined in formula (I), A is CH=CH, D is CH₂ or O and B is CH can be manufactured by reacting a compound of the formula (XV)

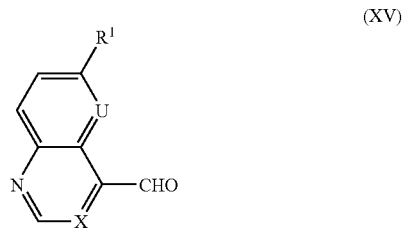
(XV)

wherein R¹, U and X are as defined in formula (I),
with a compound of formula (XVI)

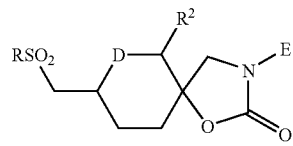

wherein R is 1-phenyl-1H-tetrazol-5-yl or benzothiazol-2-yl and D, R² and E are as defined in formula (I), in the presence of KHMDS or LiHMDS in a solvent such as 1,2-DME, DMF or toluene at a temperature between −78° C. and 0° C. (as reviewed by P. R. Blakemore in *J. Chem. Soc.*, Perkin Trans. 1 (2002), 2563-2585).

i) Compounds of formula (I) wherein A is CH=CH, D is CH₂ or O and B is CH can also be manufactured by reacting a compound of the formula (VI) wherein L¹ is halogen such as bromine with a compound of formula (XVII)

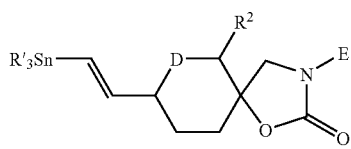

wherein R' is alkyl such as n-butyl and D, R² and E are as defined in formula (I), under Stille coupling conditions in the presence of palladium salts (as reviewed in *J. Am. Chem. Soc.* (1987), 109(18), 5478-86).

j) Compounds of formula (I) wherein A is CH₂CH₂, B is CH and D is CH₂ or O, or B is COH and D is CH₂ can be manufactured by catalytic hydrogenation of a compound of formula (Ia)

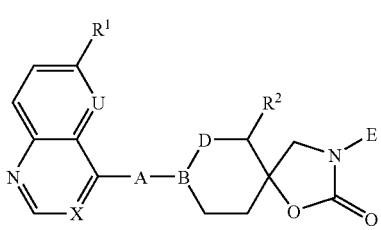

wherein A is CH=CH or C≡C and R¹, U, X, B, D, R² and E have the same meaning as in formula (I), over a noble catalyst such as palladium or platinum in a solvent such as THF, ethyl acetate, MeOH between 0° C. and 40° C. under a pressure between 1 and 10 bars.

k) Compounds of formula (I) wherein R² is hydroxyalkyl can be manufactured by deprotection of the corresponding derivative of formula (XVIII)

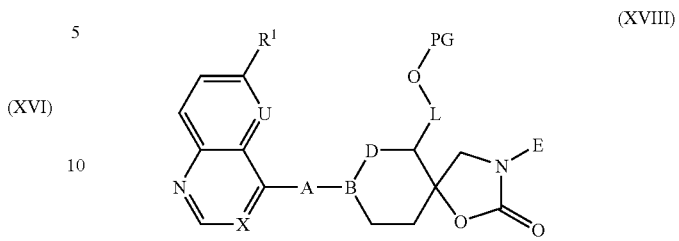

wherein R¹, U, X, A, B, D and E have the same meaning as in formula (I), L represents a straight or branched alkanediyl radical of 1 to 4 carbon atoms and PG is a protecting group for an alcohol function (e.g benzyl, acetyl, TBDMS or TBDPS). A variety of protecting groups for alcohol functions and the strategy to unprotect them has been described in reference books such as P. J. Kocienski, 'Protecting Groups', Thieme (1994). For example, a tert-butyl dimethylsilyl or tert-butyl-diphenylsilyl protecting group can be removed in presence of fluorine anions (provided by e.g. HF or tetrabutyl ammonium fluoride) or in presence of an acid such as TFA in a solvent such as THF or DCM in presence of water. The reaction is carried out between 0° C. and 50° C.

l) Compounds of formula (I) wherein R² is $(CH_2)_kOH$ wherein k is an integer from 2 to 4 can be manufactured by reduction of the corresponding derivative wherein R² is $(CH_2)_{k-1}COOR'$ wherein R' is alkyl or arylalkyl with a boron or aluminium hydride reducing agent such as LiBH₄ or LiAlH₄ in a solvent such as THF between −20° C. and 40° C. Alternatively, the ester function is hydrolyzed into its corresponding acid using a alkali hydroxide such as NaOH, KOH or LiOH in water or in a mixture of water with polar protic or aprotic organic solvent such as THF or MeOH between −10° C. and 50° C. The resulting carboxylic acid is further reduced into the corresponding alcohol using a borane derivative such as a BH₃.THF complex in a solvent such as THF between −10° C. and 40° C.

m) Compounds of formula (I) wherein A is CH₂CH₂, D is CH₂ and B is N can be manufactured by reacting a compound of the formula (XIX)

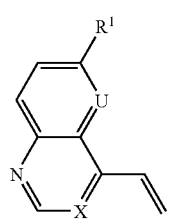

wherein R¹, U and X are as defined in formula (I),
with a compound of formula (V) as defined previously.

The reaction is performed between 40° C. and 140° C. in an organic solvent such as dioxane if necessary in presence of an organic solvent such as acetic acid.

n) Compounds of formula (I) wherein A is CH₂CH(OH), B is CH and D is CH₂ or O, or B is COH and D is CH₂ can be manufactured by transforming a compound of the formula (I) wherein A is CH(OH)CH(OH) into its corresponding cyclic carbonate followed by hydrogenolysis over a noble catalyst. The first step of the transformation is carried out by treatment with either phosgene, diphosgene or triphosgene in presence of an organic base such as TEA or pyridine or carbonyldimidazole in an inert solvent such as DCM or THF at a temperature ranging between −78° C. and 50° C., and preferably at a temperature ranging between 0° C. and 20° C. The intermediate cyclic carbonate is subsequently transformed into the homobenzylic alcohol by hydrogenolysis using a catalytic system such as Pd/C in presence of hydrogen in a solvent such as EA.

The compounds of formula (I) obtained according to the abovementioned general preparation methods may then, if desired, be converted into their salts, and notably into their pharmaceutically acceptable salts.

Besides, whenever the compounds of formula (I) are obtained in the form of mixtures of enantiomers, the enantiomers can be separated using methods known to one skilled in the art (e.g. by formation and separation of diatereomeric salts or by chromatography over a chiral stationary phase). Whenever the compounds of formula (I) are obtained in the form of mixtures of diasteromers they may be separated by an appropriate combination of silica gel chromatography, HPLC and crystallization techniques.

Preparation of the Intermediates:

The intermediates of formula (II) can be obtained using the synthetic route shown in Scheme 1 hereafter.

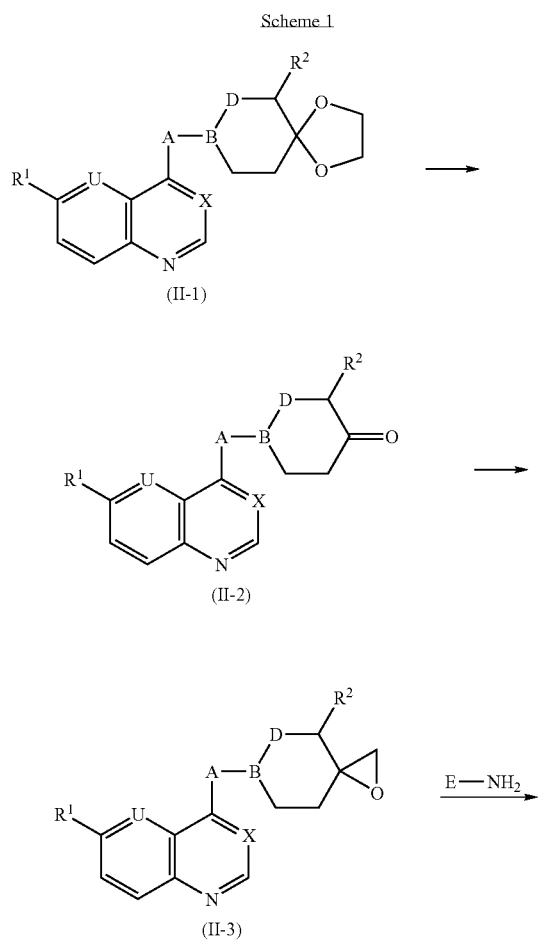

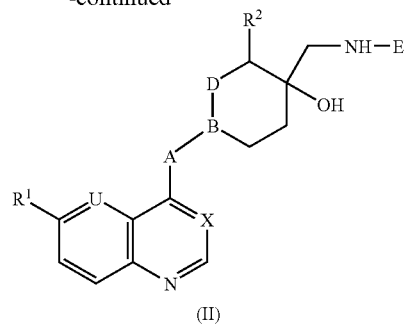

In Scheme 1, U, X, A, B, D, E, $R^1$ and $R^2$ have the same meaning as in formula (I).

The ketal function of the compounds of formula (II-1) can be removed under acidic conditions such as diluted HCl in MeOH or by using an acidic resin such as Amberlite IR120H or DOWEX 50W8 in a water-solvent mixture such as MeOH/water or THF/water. The intermediates of formula (II-2) can be transformed into the corresponding epoxide derivatives of formula (II-3) by reaction with trimethylsulfoxonium iodide or trimethylsulfonium iodide in presence of an alkali hydroxide such as KOH in a polar solvent such as MeCN between 20 and 100° C. (as described in *J. Am. Chem. Soc.* (1965), 87, 1353-1364 and *Tetrahedron Lett.* (1987), 28, 1877-1878). The epoxide derivatives of formula (II-3) can be treated with the aniline derivative E-NH$_2$ in a protic solvent such as EtOH between 50 and 90° C. to afford the intermediate of formula (II).

The piperidine derivatives of formula (V) can be obtained using the synthetic route shown in Scheme 2 hereafter.

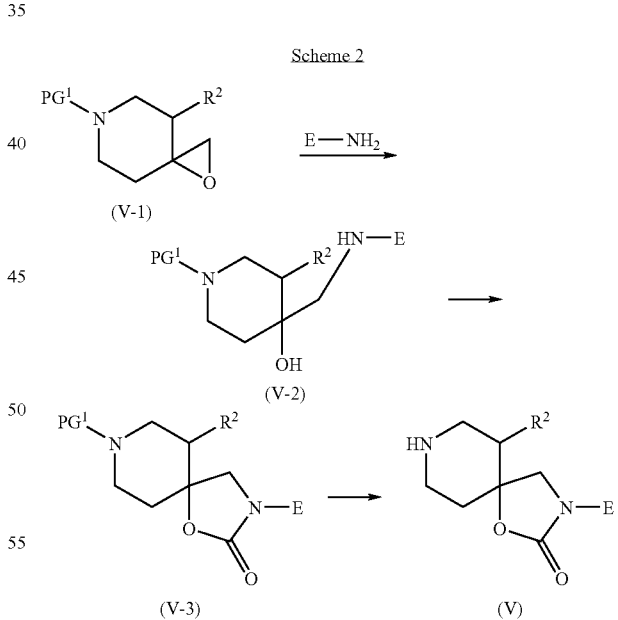

In Scheme 2, $PG^1$ is a protecting group such as benzyloxycarbonyl, tert-butoxycarbonyl or allyloxycarbonyl and E and $R^2$ have the same meaning as in formula (I).

The epoxides of formula (V-1) can be reacted with an aniline derivative of formula E-NH$_2$ in a protic solvent such as EtOH between 50 and 90° C. The resulting aminoalcohol derivatives of formula (V-2) can be reacted with an activated carbonic acid derivative such as phosgene, triphosgene, carbonyldiimidazole or disuccinidylcarbonate, in an aprotic solvent such as DCM or THF between −10° and +40° C. The resulting oxazolidinone of formula (V-3) can be deprotected using standard methods listed in reference book such as P. J. Kocienski, "Protecting groups", Thieme (1994). For example, when $PG^1$ is a benzyloxycarbonyl group, it can be removed by hydrogenation over a noble metal such as palladium.

The alcohol derivatives of formula (VII), the carboxylic acid derivatives of formula (IX), the amide derivatives of formula (XI) and the aldehyde derivatives of formula (XX)

wherein L represents a straight or branched alkanediyl radical of 1 to 4 carbon atoms can be obtained as summarized in Schemes 3 to 5 hereafter.

For the alcohol derivatives of formula (VIa), the carboxylic acid derivatives of formula (IXa), the amide derivatives of formula (XIa) and the aldehyde derivatives of formula (XXa) wherein B is CH, D is $CH_2$ and $R^2$ and E are as defined in the corresponding derivatives of formulae (VII), (IX), (XI) and (XX), the synthetic route shown in Scheme 3 is used.

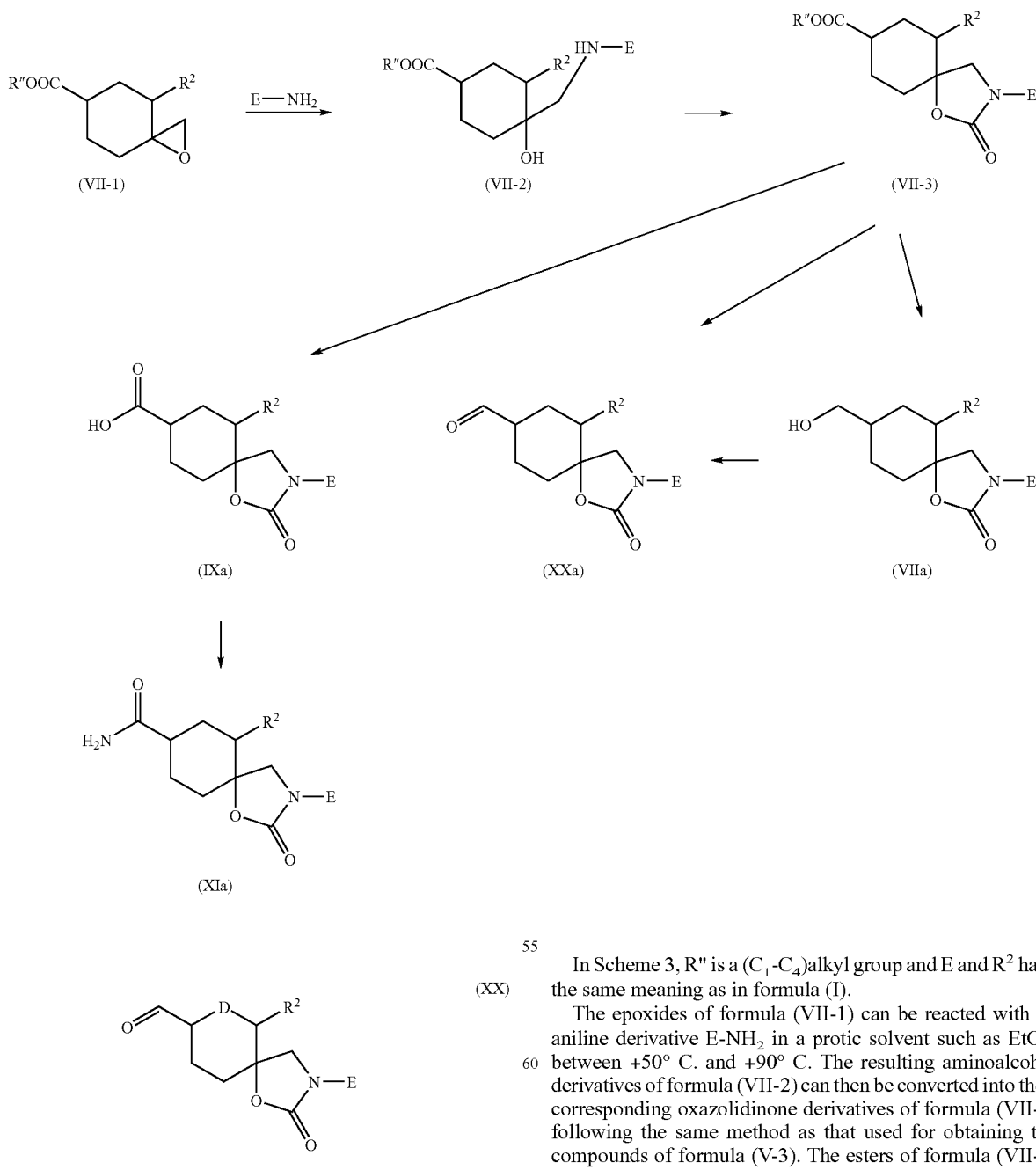

wherein D and E are as defined in formula (I) and $R^2$ is either H, alkyl, alkenyl, alkoxycarbonylalkyl or a group -L-OBn In Scheme 3, R" is a $(C_1-C_4)$alkyl group and E and $R^2$ have the same meaning as in formula (I).

The epoxides of formula (VII-1) can be reacted with an aniline derivative $E-NH_2$ in a protic solvent such as EtOH between +50° C. and +90° C. The resulting aminoalcohol derivatives of formula (VII-2) can then be converted into their corresponding oxazolidinone derivatives of formula (VII-3) following the same method as that used for obtaining the compounds of formula (V-3). The esters of formula (VII-3) can be transformed into the corresponding alcohol of formula (VIIa) by reduction with a borohydride reducing agent such as $NaBH_4$ or $LiBH_4$ in a solvent such as THF or MeOH between −10° and 50° C. The esters of formula (VII-3) can also be treated with an alkali hydroxide such as LiOH in a water-dioxane mixture between 0° and 50° C. to yield the cyclohexanecarboxylic acid derivatives of formula (IXa), which can be converted into the amide of formula (XIa) by standard methods (e.g. by transformation of the acid into its corresponding acid chloride and subsequent reaction with ammonia). Both the esters of formula (VII-3) and the alcohols of formula (VIa) can be transformed into their corresponding aldehydes (XXa) by either controlled reduction with a bulky hydride reagent such as DIBAH or oxidation under Swern (see D. Swern et al., *J. Org. Chem.* (1978), 43, 2480-2482) or Dess Martin (see D. B. Dess and J. C. Martin, *J. Org. Chem.* (1983), 48, 4155) conditions, respectively.

For the alcohol derivatives of formula (VIIb), the carboxylic acid derivatives of formula (IXb), the amide derivatives of formula (XIb) and the aldehyde derivatives of formula (XXb) wherein B is CH, D is O and E is as defined in the corresponding derivatives of formulae (VII), (IX), (XI) and (XX), the synthetic route shown in Scheme 4 is used.

In Scheme 4, E has the same meaning as in formula (I) and L represents a straight or branched alkanediyl radical of 1 to 4 carbon atoms.

The alcohol function of the compound of formula (VII-4) can be oxidized into the corresponding ketone of formula (VII-5) using standard protocols such as Swern or Dess Martin conditions. Said ketone can be further transformed into the corresponding epoxide derivative of formula (VII-6) by reaction with trimethylsulfonium iodide or trimethyl sulfoxonium iodide between 20° C. and 80° C. in a solvent such as MeCN. Alternatively, the epoxide derivative of formula (VII-6) can be obtained by transforming the ketone into an alkene using a Wittig olefination reaction followed by an epoxidation with a peracid such as MCPBA. The epoxide can be transformed into the corresponding spiro derivative of formula (VII-7) using the same procedures as described for the synthesis of compounds of formula (V-3). The silyl protecting group of the derivatives of formula (VII-7) can be removed as described in section k) above. The primary alcohol can be transformed by standard methods into the corresponding car-

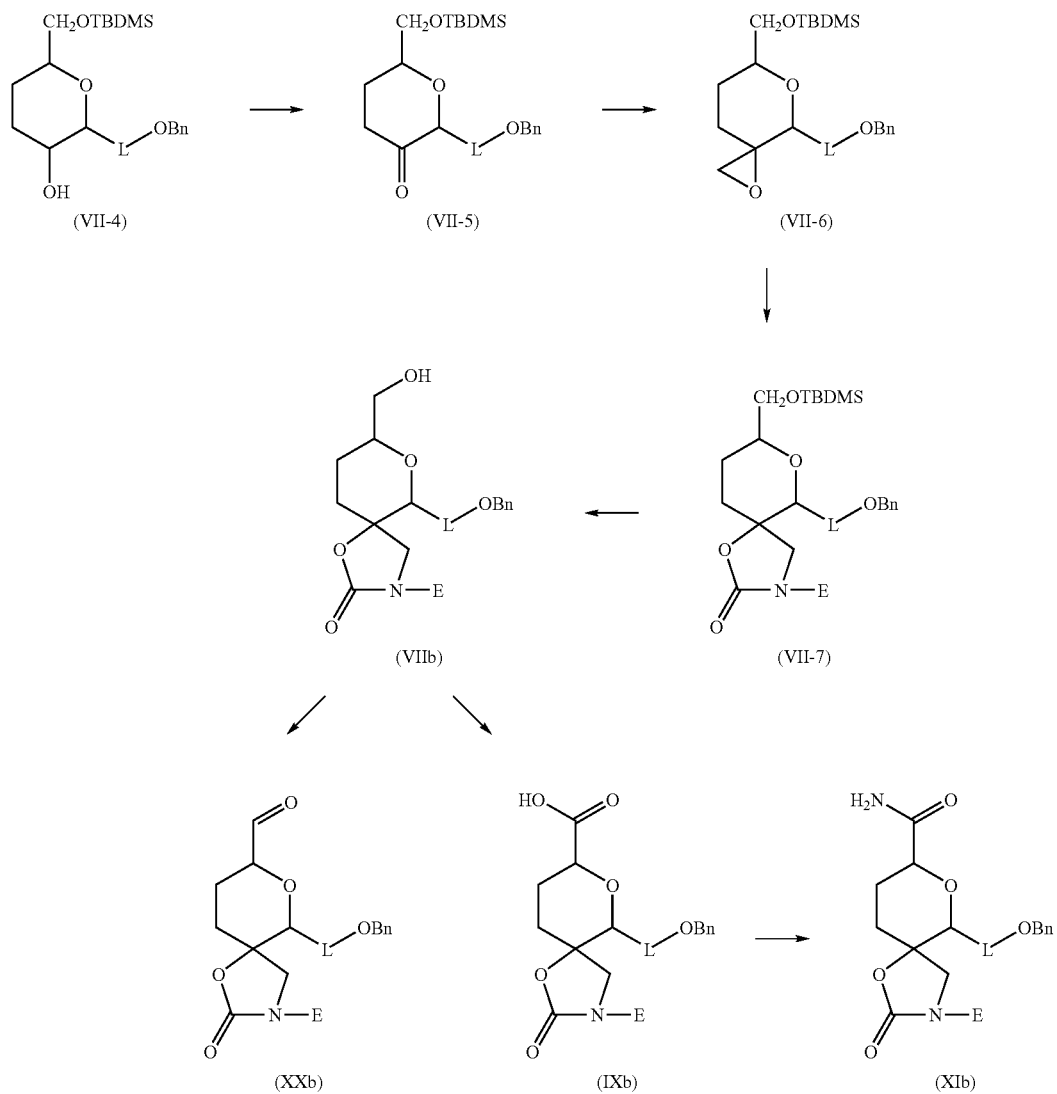

boxylic acids and amides of formulae (IXb) and (XIb), it being understood that an additional deprotection step is necessary in the particular cases wherein $R^{2a}$ is -L-OBn. Alternatively, the compounds of formula (VIIb) can be transformed into the corresponding aldehydes of formula (XXb) using Swern or Dess Martin protocols. The benzyl ether of the compound of formula (VII-4) can be further transformed into the free alcohol and further elaborated to access compounds of formula (I) wherein $R^2$ is alkyl, alkenyl or alkyloxycarbonyl.

For the alcohol derivatives of formula (VIIc), the carboxylic acid derivatives of formula (IXc), the amide derivatives of formula (XIc) and the aldehyde derivatives of formula (XXc) wherein B is C(OH), D is $CH_2$, $R^2$ is H, alkyl, alkenyl or alkoxycarbonylalkyl, and E is as defined in the corresponding derivatives of formula (VII), (IX), (XI) and (XX), the synthetic route shown in Scheme 5 is used.

formed into its corresponding alcohol of formula (VIIc) by reduction with an aluminium or boron reducing agent such as $NaBH_4$ or $LiAlH_4$. The ethyl ester derivative of formula (VII-10) can also be transformed into the aldehyde of formula (XXc) by reduction with an aluminium reducing agent such as DIBAH. The ester can also be hydrolyzed into the acid of formula (IXc) and further transformed into the corresponding primary amide of formula (XIc). These four building blocks can be further transformed using the same methodologies as for the examples wherein B is CH and D is $CH_2$.

Intermediates of formula (XIVa) wherein B is CH or C(OH), D is $CH_2$, $R^2$ is H, alkyl, alkenyl or alkoxycarbonylalkyl, and E is as defined in the corresponding derivatives of formula (XIV) are obtained as described in Scheme 6.

Scheme 5

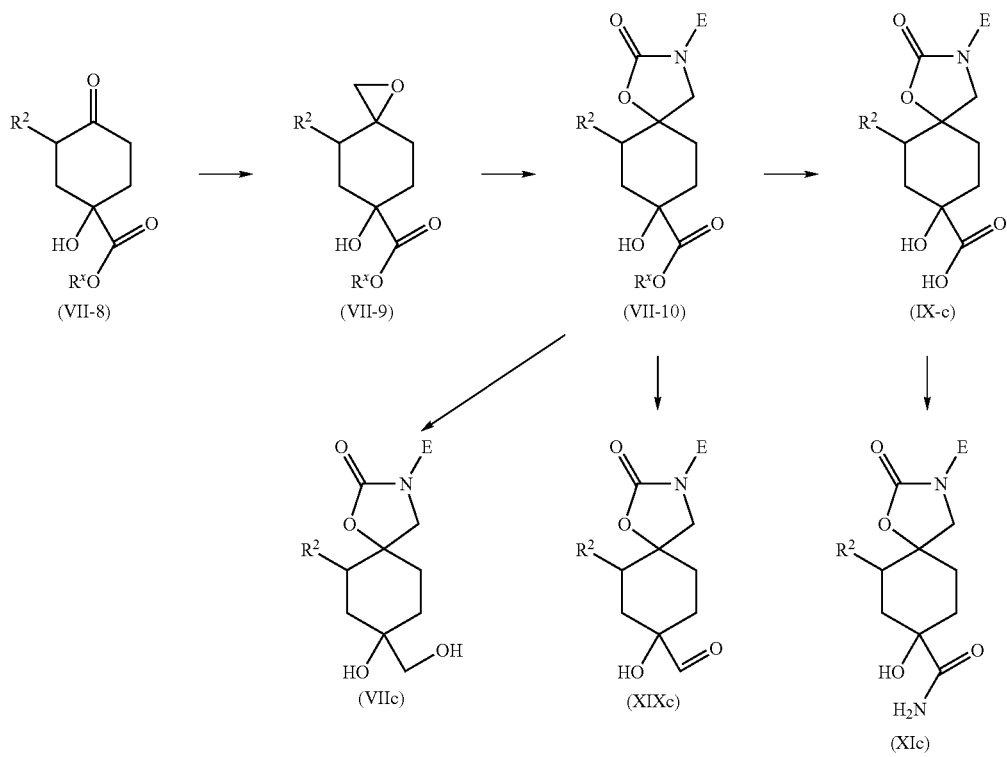

In Scheme 5, E is as defined in formula (I), $R^2$ is H, alkyl, alkenyl or alkoxycarbonylalkyl, and $R^x$ represents alkyl (e.g. ethyl), it being understood that when $R^2$ is alkoxycarbonylalkyl then the alkyl radical $R^x$ is such that it allows differentiation of both ester functions of the compounds of formula (VII-10), i.e. that the ester function —$COOR^x$ can be selectively removed (to allow further elaboration).

1-hydroxy-4-oxo-cyclohexanecarboxylic acid ethyl ester (prepared according to DE 19742492) or its derivative of formula (VII-8) can be transformed into its corresponding epoxide of formula (VII-9) and oxazolidinone of formula (VII-10) following methodologies described previously. The ethyl ester derivative of formula (VII-10) can then be trans- Scheme 6

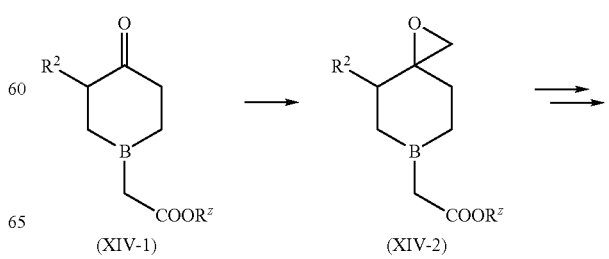

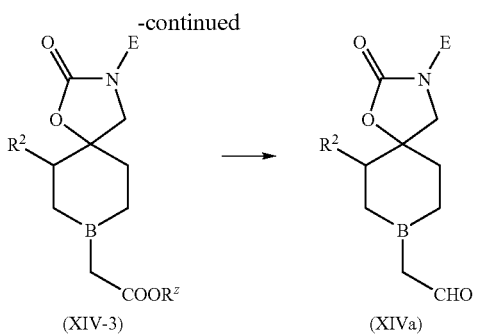

In Scheme 6, E has the same meaning as in formula (I), $R^2$ is H, alkyl, alkenyl or alkoxycarbonylalkyl, B represents CH or C(OH), and $R^z$ represents alkyl (e.g. ethyl), it being understood however that when $R^2$ is alkoxycarbonylalkyl then the alkyl radical $R^z$ is such that it allows differentiation of both ester functions of the compounds of formula (XIV-3), i.e. that the ester function —$COOR^z$ can be selectively removed.

The ketone derivatives of formula (XIV-1) (which, when $R^2$ is H and $R^z$ is ethyl, can be obtained according to *Can. J. Chem.* (1976), 54, 3569-79 (B=CH) or to *Organic Letters* (2005), 7, 5673-5676 (R=C(OH)) can be transformed into their corresponding epoxides of formula (XIV-2) using the same methodology as described for the preparation of compounds of formula (VII-6) or via transformation of the ketone derivatives into their methylidene analogues using a Wittig reaction with methylidene triphenylphosphorane and subsequent epoxidation with a peracid such as MCPBA. The epoxides can be further transformed into the corresponding oxazolidinones of formula (XIV-3) following methodologies used for the formation of compounds of formulae (I) and (II). Finally, the ester function of the compound of formula (XIV-3) can be reduced using DIBAH to yield the aldehyde of formula (XIVa).

The compounds of formula (XIVb) wherein B is CH, D is O, $R^2$ is H, alkyl, hydroxyalkyl, alkenyl or alkoxycarbonylalkyl, and E is as defined in the corresponding derivatives of formula (XIV) can be prepared by the synthetic route shown in Scheme 7 hereafter.

Scheme 7

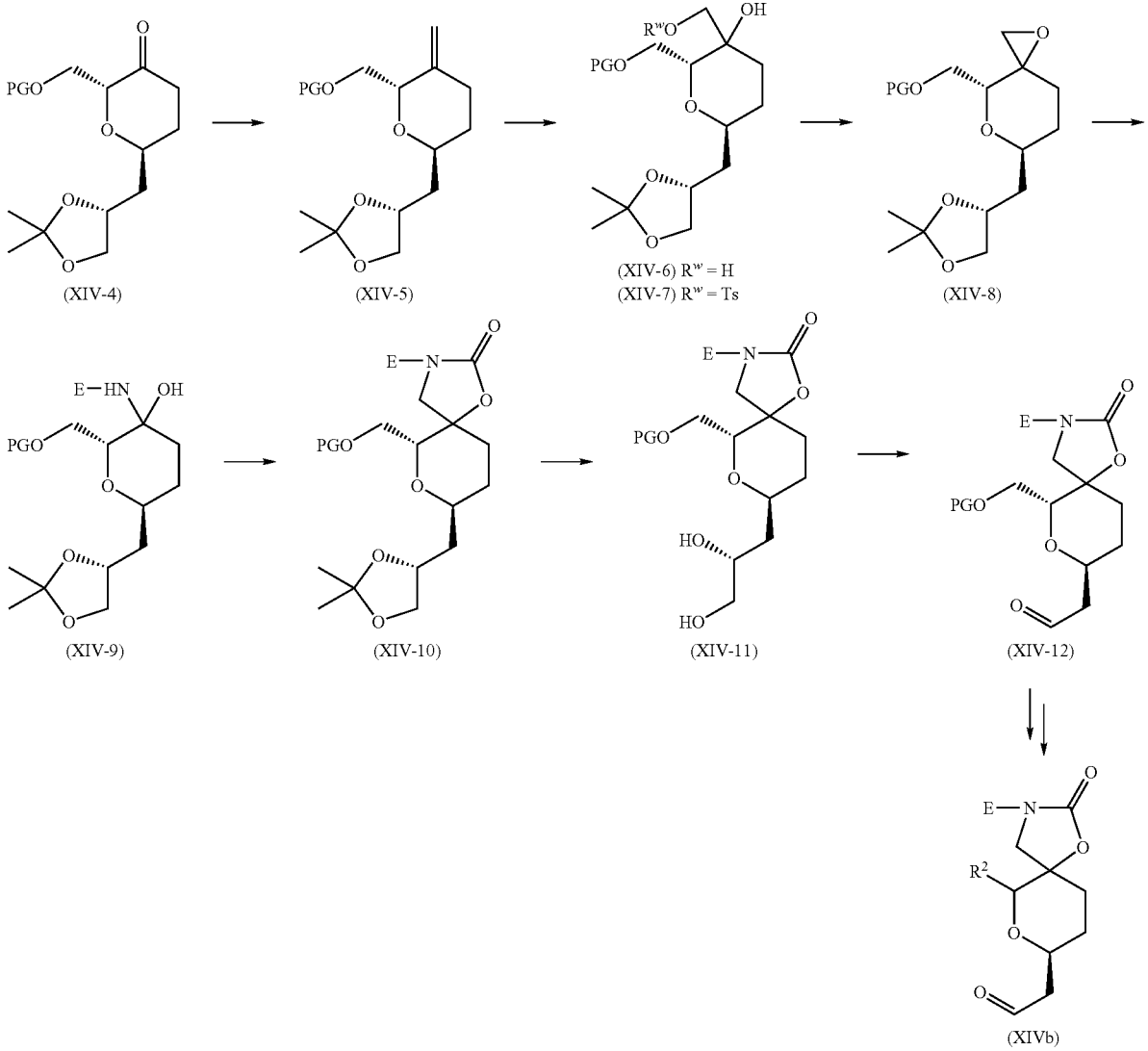

In Scheme 7, PG is a protecting group such as TBDMS or TBDPS and E and $R^2$ have the same meaning as in formula (I).

The compound of formula (XIV-4), obtained in analogy to the corresponding tert-butyl-dimethylsilyl ether (*Chemistry—A European Journal* (2002), 8(7), 1670-81), can be subjected to Wittig reaction with methylidenetriphenylphosphorane in presence of n-BuLi in THF between −70° C. and 0° C. The resulting methylidene derivative of formula (XIV-5) can be subjected to an asymmetric cis-dihydroxylation by treatment with AD mixtures (AD-mix α or AD-mix β) in presence of methanesulfonamide in a water/2-methyl-2-propanol mixture as described in *Chem. Rev.* (1994), 94, 2483. The sense of induction relies on the chiral ligand contained in the mixture, either a dihydroquinine-based ligand in AD-mix α or a dihydroquinidine-based ligand in AD-mix β. The resulting diol of formula (XIV-6) can be selectively reacted with p-TsCl in presence of TEA in a solvent such as DCM between 0° C. and rt. The corresponding tosylate of formula (XIV-7) can be transformed into the epoxide of formula (XIV-8) in presence of NaH between −20° C. and rt. The epoxide can then be reacted with the aniline E-$NH_2$ as described previously. The aminoalcohol derivative of formula (XIV-9) can be transformed into the corresponding oxazolidinone of formula (XIV-10) as described previously. This intermediate can then be treated under acidic conditions (e.g. AcOH) to give the corresponding diol of formula (XIV-11) which can be transformed into the compound of formula (XIV-12) after periodate cleavage. The compound of formula (XIV-12) can then be converted in one or more steps using standard methods into the desired compound of formula (XIVb).

The aldehydes of formula (XV) are prepared following literature procedures or from the corresponding derivatives of formula (X) ($L^1$=Br) by treatment with an alkyl lithium such as n-BuLi at a temperature ranging between −80° C. and −30° C. and subsequent quenching of the lithio species with DMF as described in *J. Org. Chem.* (1980), 45, 1514. An alternate route to generate the aldehydes of formula (XV) consists in reacting derivatives of formula (X) (wherein $L^1$=OTf, Br or Cl) with trans-phenylvinyl boronic acid under typical Miyaura-Suzuki coupling conditions (see *Synth. Commun.* (1981), 11, 513) or with vinyl tributylstannane under typical Stille coupling conditions, employing a palladium salt, an inorganic base such as $K_2CO_3$ or $Na_2CO_3$, in an aq. solvent such as a dioxane-water mixture at a temperature ranging between 20° and 100° C. The corresponding alkene may be directly transformed into the aldehyde of formula (XV) by ozonolysis ($O_3$ stream then quenching with either dimethylsulfide or $PPh_3$) or via a periodate cleavage of the intermediate diol using $NaIO_4$ in aq. acetone. The diol is obtained using a catalytic amount of osmium tetroxide in the presence a co-oxidant such as NMO in aq. solvent such as an acetone-water or DCM-water mixture (see Cha, J. K. *Chem. Rev.* (1995), 95, 1761-1795).

The intermediates of formula (XVII) wherein D is O or $CH_2$ are obtained by hydrostannation reaction of the alkyne derivatives of formula (XVII-1)

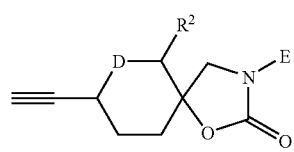

(XVII-1)

wherein D, $R^2$ and E are as defined in formula (I), using tributyl tin hydride and a catalytic amount of either a palladium salt or a molybdenum complex generating an E:Z mixture of the vinylstannane intermediate as described in *J. Org. Chem.* (1990), 55, 1857. The required alkynes can be obtained from the corresponding aldehydes of formula (XX) using either the Corey-Fuchs protocol (formation of the gem-dibromide then treatment with n-BuLi) as described in *Tetrahedron Lett.* (1972), 3769 or using the dimethyl-2-oxopropylphosphonate diazo derivative (so called Ohira's reagent, *Synth. Com.* (1989), 19, 561) or dimethyldiazomethylphosphonate as described in *Synlett* (2003), 59 and *Synlett* (1996), 521. The alkyne wherein B is C(OH) and D is $CH_2$ can be obtained according to WO 2004/035569.

The intermediates of formula (XVIIIa) which are compounds of formula (XVIII) wherein A is $CHOHCH_2$, B is CH, D is O and $R^1$ is $CH_2OH$ can be obtained using the synthetic route shown in Scheme 8 hereafter.

Scheme 8

In Scheme 8, U, X, E and $R^1$ have the same meaning as in formula (I) and PG represents a protecting group such as TBDMS or TBDPS.

The bromo derivatives of formula (XVIII-1), converted into their lithio species generated in situ by reaction with n-BuLi between −80° and −30° C. in a solvent such as THF or ether, can be reacted with the aldehydes of formula (XIV-12) to afford the compounds of formula (XVIIIa).

The intermediates of formula (XIX) are obtained by Stille coupling between tributyl vinyl stannane and the intermediates of formula (VIa) or the intermediates of formula (X) in presence of a palladium catalyst such as $PdCl_2(PPh_3)_2$ as described in WO 2006/021448.

Starting Materials:

The starting ketals of formula (II-1) wherein A is $CH_2CH_2$, B is C(OH) and D is $CH_2$ can be obtained by hydrogenation of the corresponding acetylenic ketal (obtained according to, e.g., *J. Am. Chem. Soc.* (1988), 110, 1626-28 ($R^2$=H)) or the corresponding vinylic ketal of formula (II-1a) over a noble metal such as palladium in a solvent such as EA or MeOH.

The starting vinylic ketals of formula (II-1a), which are compounds of formula (II-1) wherein A is CH=CH, B is CH and D is O or $CH_2$, can be obtained using the synthetic route shown in Scheme 9 hereafter.

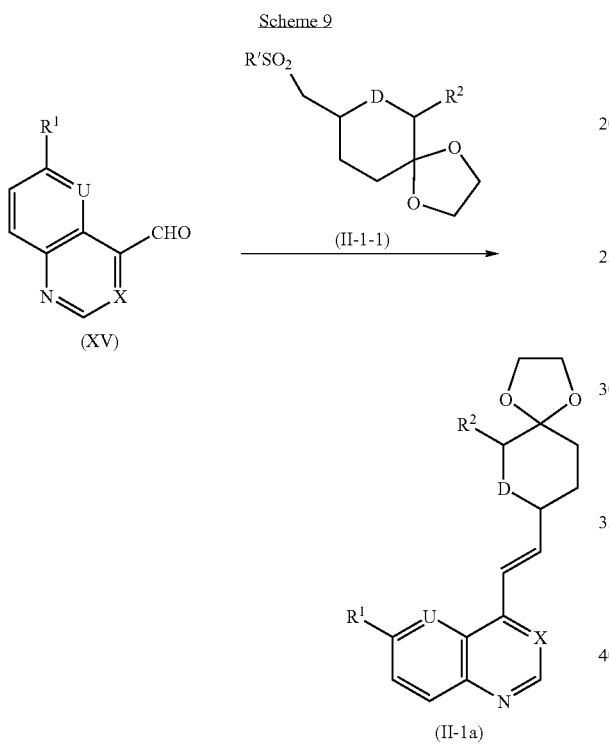

In Scheme 9, U, X and $R^1$ have the same meaning as in formula (XV), D and $R^2$ have the same meaning as in formula (I) and R' represents 1-phenyl-1H-tetrazol-5-yl.

The aldehyde derivatives of formula (XV) as defined previously can be reacted with the sulfone derivatives of formula (II-1-1) in presence of a base such as LiHMDS or KHMDS in a solvent such as 1,2-DME, DMF or toluene between −80° C. and −30° C., as reviewed by Blakemore, P. R in *J. Chem. Soc., Perkin Trans.* 1 (2002), 2563-2585.

The sulfone derivatives of formula (II-1-1) are generated from the corresponding alcohols (which alcohols are obtained either from deprotection of the compounds of formula (II-1-9) or by reduction of the compounds of formula (II-1-5) with $NaBH_4$ or $LiBH_4$, the preparation of the compounds of formula (II-1-9) or (II-1-5) being described later in this application) using a Mitsunobu coupling (as reviewed in O. Mitsunobu *Synthesis* (1981), 1) with 1-phenyl-1H-tetrazole-5-thiol in the presence of DEAD or DIAD and $PPh_3$. The reaction may be performed in a wide range of solvents such as DMF, THF or DCM and within a wide range of temperatures (between −78° C. and 50° C.). An alternate route to form the intermediate sulphide requires the activation of the alcohol as for example a tosylate, a triflate or a mesylate by treatment with p-TsCl, trifluoromethanesulphonic anhydride or MsCl respectively in the presence of an organic base such as TEA between −40° C. and 60° C. in a dry aprotic solvent like DCM, MeCN or THF. Once activated, the reaction with NaI or KI in acetone at a temperature ranging between 0° C. and 65° C., forms the corresponding iodide. The latter serves as an alkylating agent of the 1-phenyl-1H-tetrazole-5-thiol. The alkylation reaction is performed in presence of an inorganic base such as KOH or NaOH in a solvent such as EtOH at a temperature ranging between −20° C. and 70° C. The sulphide is transformed into the corresponding sulfone via an oxidation reaction. A wide range of oxidizing agent may be used, such as MCPBA in a solvent such as DCM or oxone in a solvent such as aq. MeOH (see *Tetrahedron Letters* (1981), 22, 1287), or aq. hydrogen peroxide in presence of ammonium heptamolybdate tetrahydrate in EtOH (see *J. Org. Chem.* (1963), 28, 1140).

The ketals of formula (II-1) wherein A is NHCO, can be prepared starting from the carboxylic acids of formula (II-1-2)

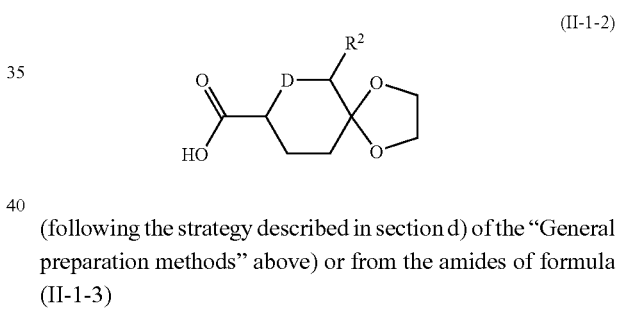

(following the strategy described in section d) of the "General preparation methods" above) or from the amides of formula (II-1-3)

(II-1-3)

(following the strategy described in section e) of the "General preparation methods" above). In the formulae (II-1-2) and (II-1-3), D and $R^2$ have the same meaning as in formula (I).

The carboxylic acids of formula (II-1-2) and the amides of formula (II-1-3) and wherein D is $CH_2$ (hereafter respectively the carboxylic acids of formula (II-1-2a) and amides of formula (II-1-3a)) can be prepared (for example) using the synthetic route shown in Scheme 10 hereafter (wherein protection/deprotection steps on the side chain $R^2$, required when $R^2$ is hydroxyalkyl, have been omitted).

Scheme 10

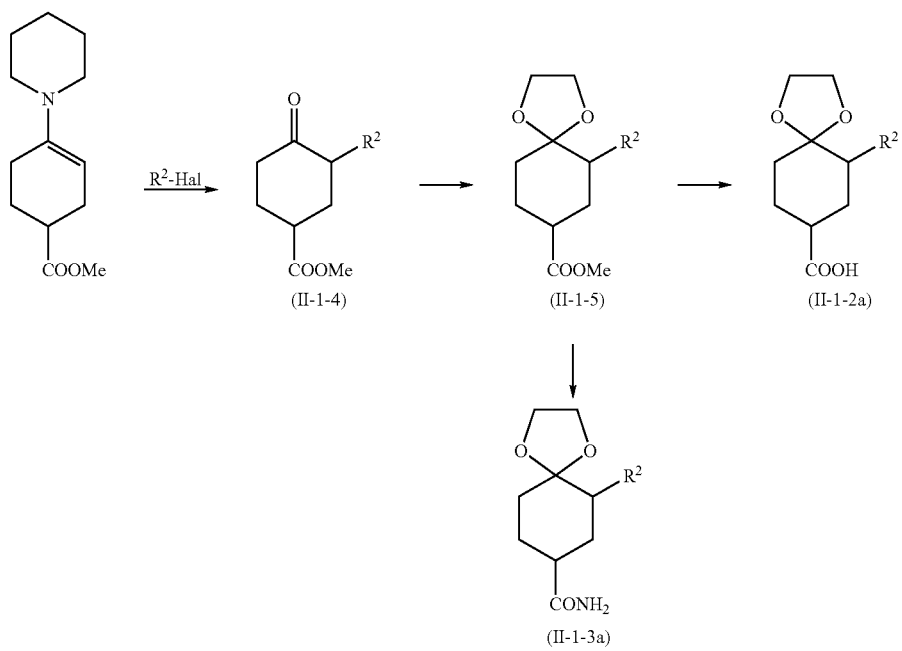

In Scheme 10, R² has the same meaning as in formula (I).

The starting compound, 4-piperidin-1-yl-cyclohex-3-en-ecarboxylic acid methyl ester (prepared as described in U.S. Pat. No. 4,221,800), can be reacted (Scheme 10) with a halide of formula R²—Hal (Hal being a halogen atom). After hydrolysis, the ketone of formula (II-1-4) can be converted into the corresponding ketal derivative of formula (II-1-5) and then into the carboxylic acid of formula (II-1-2a) or the amide of formula (II-1-3a), using methods already described previously or well known to one skilled in the art.

The carboxylic acids of formula (II-1-2) and amides of formula (II-1-3) wherein D is O (hereafter respectively the carboxylic acids of formula (II-1-2b) and amides of formula (II-1-3b)) can be prepared (for example) using the synthetic route shown in Scheme 11 hereafter (wherein protection/deprotection steps on the side chain R², required when R² is hydroxyalkyl, have been omitted).

Scheme 11

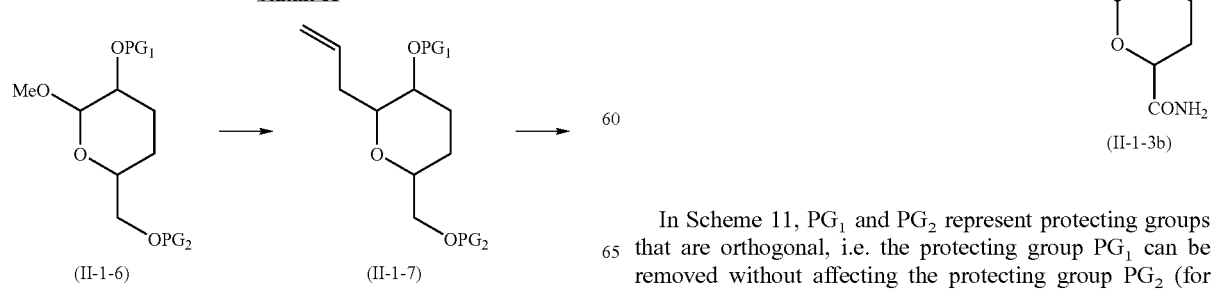

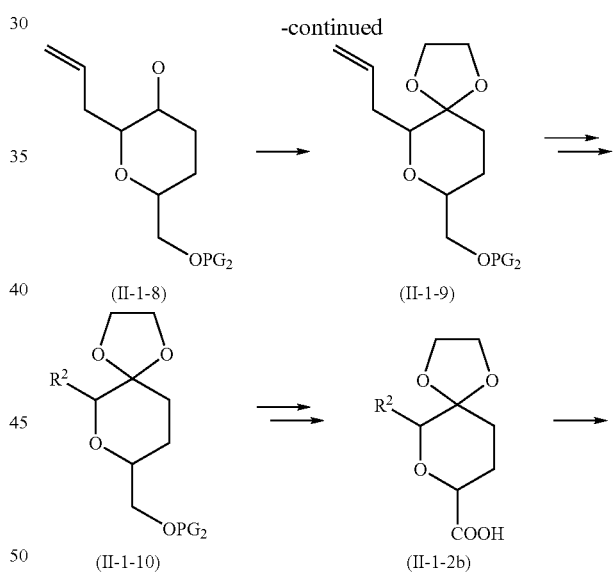

In Scheme 11, PG₁ and PG₂ represent protecting groups that are orthogonal, i.e. the protecting group PG₁ can be removed without affecting the protecting group PG₂ (for example PG₁ is benzyl and PG₂ represents a silyl protecting group such as tert-butyl dimethylsilyl or tert-butyldiphenyl-silyl, or vice versa) and $R^2$ represents alkyl, alkenyl, hydroxyalkyl or alkoxycarbonylalkyl.

The compound of formula (II-1-6) can be reacted (Scheme 11) either with allyl-trimethyl-silane or with allyl chloride and 1,1,1,2,2,2-hexamethyl-disilane. The protecting group $PG_1$ of the resulting compound of formula (II-1-7) can then be removed to yield intermediately the free alcohol which can be oxidized into the ketone derivative of formula (II-1-8). Protection of the ketone yields the ketal derivative of formula (II-1-9) which can then be transformed into the corresponding ketal (II-1-10) using methods known from the skilled in the art and further converted to the carboxylic acid of formula (II-1-2b) and to the amide of formula (II-1-3b), using methods already described previously or well known to one skilled in the art.

The ketals of formula (II-1b), which are compounds of formula (II-1) wherein A is $OCH_2$, can be prepared following the same strategy as described in section c) of the "General preparation methods" above, starting from the compounds of formula (VIa) wherein $L^1$ is Br and the required ketal alcohols of formula (II-1-12) or (II-1-14) (the structure of which is shown in Scheme 12 hereafter), which are either commercially available or derived from intermediates previously described.

12) or (II-1-14), obtained by treatment with a metal hydride such as NaH, can then be reacted with a compound of formula (VIa).

Alternatively, the ethers of formula (II-1b) can also be obtained by reaction of the alcohol of formula (II-1-11) or (II-1-13) with a compound of formula (VI) using the Mitsunobu coupling protocols described above.

The epoxides of formula (IV) can be prepared as described in WO 00/78748, WO 2004/02490, WO 02/008224 or WO 2006/032466.

The epoxides of formula (V-1), wherein $PG^1$ is a protecting group such as benzyloxycarbonyl, tert-butoxycarbonyl or allyloxycarbonyl, can be prepared according to U.S. Pat. No. 4,244,961 and/or standard methods well known to one skilled in the art.

The required quinoline, [1,5]-naphthyridine and quinazoline derivatives of formula (VI) are prepared following literature procedures. For example, the 4-hydroxy-[1,5]-naphthyridines ($L^1$=OH, U=N and X=CH) and 4-hydroxy-quinolines ($L^1$=OH and U=X=CH) can be prepared from the corresponding aminopyridine or aniline by reaction with diethyl ethoxymethylene malonate to produce the 4-hydroxy-carboxylic acid ester derivative with subsequent hydrolysis to the acid, followed by thermal decarboxylation in inert solvents (J. T. Adams, *J. Am. Chem. Soc.* (1946), 68, 1317). Others routes to such derivatives uses the condensation of substituted aminopyridines or anilines with 2,2-dimethyl-[1, Scheme 12

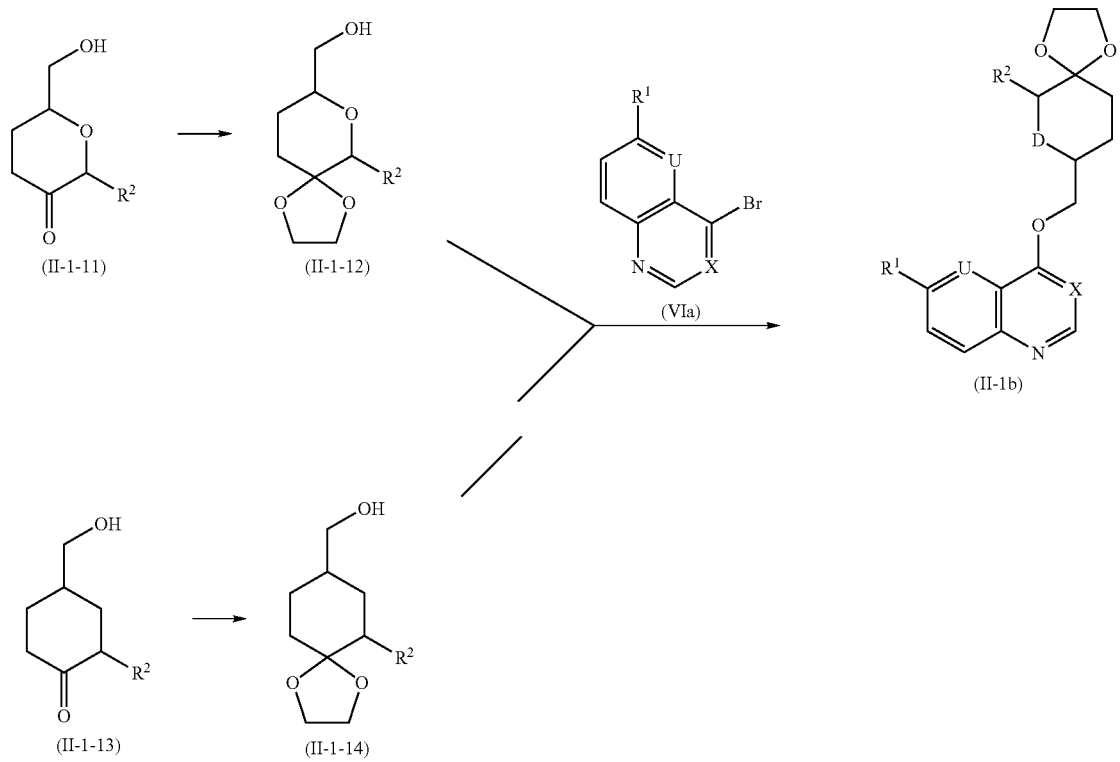

For example, as shown in Scheme 12 (wherein protection/deprotection steps on the side chain $R^2$, possibly required when $R^2$ is hydroxyalkyl, have been omitted), the compound of formula (II-1-11) or (II-1-13) can be ketalized with ethanediol in a dry solvent and in presence of an acid catalyst such as para-toluenesulfonic acid between 20° C. and 140° C. The alcoholate of the resulting intermediate of formula (II-1-

3]dioxane-dione and triethylorthoformate followed by heating of the resulting 2,2-dimethyl-5-[(arylamino)meth-ylidene]-1,3-dioxane-4,6-dione intermediate in refluxing diphenyl ether. The quinazolines ($L^1$=OH, $C_1$, $NH_2$, X=N and U=CH) may be prepared by standard routes as described by T. A. Williamson in *Heterocyclic Compounds* (1957), 6, 324.

The epoxides of formula (VII-1) can be prepared according to *Tetrahedron* (1995), 51, 10259-280, and/or standard methods well known to one skilled in the art.

The tetrahydropyran derivatives of formula (VII-4) wherein L is $CH_2$ can be prepared using *J. Chem. Soc. Perkin 1* (1995), 2487-95. In the other cases, the compounds of formula (VII-4) can be prepared using the synthetic route shown in Scheme 13 hereafter.

Scheme 13

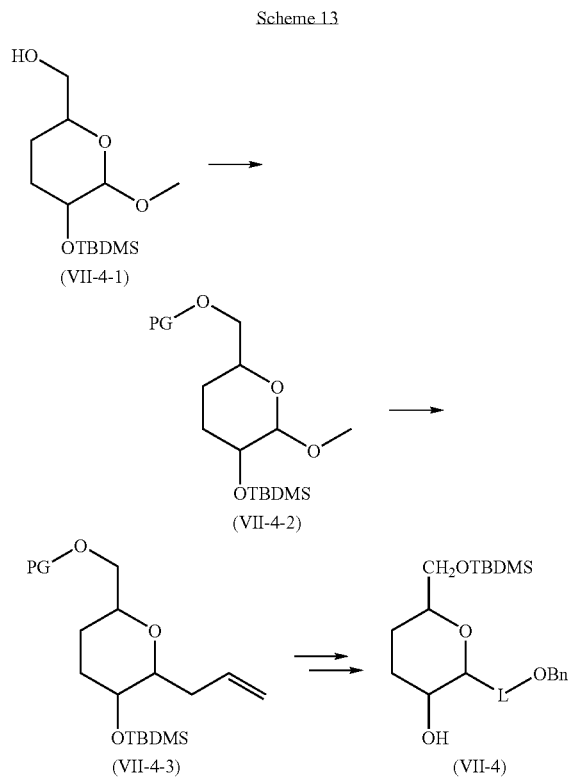

In Scheme 13, PG represents a protecting group for an alcohol function which is different from a silyl group (e.g. acetyl, para-methoxybenzyl or methoxyethoxymethyl) and L is an alkanediyl chain of 2 to 4 carbon atoms.

The alcohol function of the tetrahydropyrane derivative of formula (VII-4-1), which can be prepared for example according to *J. Org. Chem.* (1984), 49, 3994-4003, can be protected using conventional methods (see Scheme 13). The intermediate of formula (VII-4-2) thus obtained can then be converted into its allyl derivative of formula (VII-4-3) according to a protocol described in *Bioorg. Med. Chem.* (2006), 14, 3349-3367. The allyl derivative of formula (VII-4-3) may then be converted to the desired compound of formula (VII-4) using standard methods well known to one skilled in the art.

The required quinoline and [1,5]-naphthyridine derivatives of formula (VIII) are either commercially available or prepared as described in *Austr. J. Chem.* (2003), 56, 39, and WO 96/33195.

The required quinoline, [1,5]-naphthyridine and quinazoline derivatives of formula (X) are prepared from the corresponding derivatives of formula (VI) wherein $L^1$ is OH following procedures analogous to those described in WO 00/40554, WO 02/008224 and WO 2004/002490.

The required quinoline, [1,5]-naphthyridine and quinazoline derivatives of formula (VIa) are either commercially available or prepared following literature procedures. For example, compounds wherein $L^1$=Br and U=X=CH are prepared according to WO 2003/087098, compounds wherein $L^1$=Br, U=N and X=CH are prepared according to WO 2006/032466, and compounds wherein $L^1$=Cl and U=X=CH are prepared according to WO 2004/089947.

The lithio derivatives of formula (XIII) can be prepared from the corresponding phenols by reaction with $PBr_3$ in DMF at 40° C. followed by a reaction with n-BuLi between −80° and −30° C. in a solvent such as THF or ether.

The required quinoline and [1,5]-naphthyridine aldehyde derivatives of formula (XV) are either commercially available or prepared as described in *J. Med. Chem.* (1970), 13, 1117, WO 2006/046552, WO 2006/021448 or WO 2006/032466.

Particular embodiments of the invention are described in the following Examples, which serve to illustrate the invention in more detail without limiting its scope in any way.

EXAMPLES

Example 1

(5R,6R,8S)-3-(2,3-dihydro-benzo[1,4]dioxin-6-yl)-8-[(2R)-2-hydroxy-2-(6-methoxy-[1,5]naphthyridin-4-yl)-ethyl]-6-hydroxymethyl-1,7-dioxa-3-aza-spiro[4.5]decan-2-one and (5R,6R,8S)-3-(2,3-dihydro-benzo[1,4]dioxin-6-yl)-8-[(2S)-2-hydroxy-2-(6-methoxy-[1,5]naphthyridin-4-yl)-ethyl]-6-hydroxymethyl-1,7-dioxa-3-aza-spiro[4.5]decan-2-one 1.i. (2R,3S,6R)-6-allyl-2-(tert-butyl-diphenyl-silanyloxymethyl)-3,6-dihydro-2H-pyran-3-ol To an ice-chilled solution of (2R,3S,6R)-6-allyl-2-hydroxymethyl-3,6-dihydro-2H-pyran-3-ol (obtained as described in *Eur. J. Org. Chem.* (2003), 2418-2427; 31.55 g, 185.4 mmol) in DCM (650 ml) was added imidazole (24.96 g, 2 eq.). A solution of tert-butylchlorodiphenylsilane (50.45 g, 210.7 mmol) in DCM (130 ml) was added dropwise over 90 min. After 2 h, aq. sat. $NaHCO_3$ (250 ml) was added. The yield after chromatography (Hex/EA 5:1) was 51.52 g (68%; yellow oil).

$^1$H NMR ($CDCl_3$) δ: 7.74-7.68 (m, 4H); 7.47-7.38 (6H); 5.87-5.76 (m, 3H); 5.10-5.04 (m, 2H); 4.19-4.15 (m, 2H); 3.89 (dd, J=5.3, 10.0 Hz, 1H); 3.79 (dd, J=7.3, 10.0 Hz, 1H); 3.68 (m, 1H); 2.70 (br s, 1H); 2.38 (m, 1H); 2.28 (m, 1H); 1.09 (s, 9H).

1.ii. (2RS)-3-[(2R,5S,6R)-6-(tert-butyl-diphenyl-silanyloxymethyl)-5-hydroxy-5,6-dihydro-2H-pyran-2-yl]-propane-1,2-diol To a solution of intermediate 1.i (51.52 g, 126.1 mmol) in 2-methyl-2-propanol (560 ml), EA (15 ml) and water (560 ml), were added potassium ferricyanide (189.48 g, 3 eq.), $K_2CO_3$ (67.10 g, 3 eq.), $(DHQD)_2PHAL$ (1.5121 g, 0.015 eq.) and potassium osmate dihydrate (0.1907 g, 0.004 eq.). The reaction mixture was stirred for two days and sodium bisulfite (150.92 g) was added. The two layers were decanted and the aq. layer was extracted twice with EA (2×350 ml). The yield after work up and chromatography (Hex/EA 1:1, then EA) was 36.33 g (65%; yellow oil). The compound was obtained as a 2:1 mixture of epimers.

¹H NMR (d₆-DMSO) δ: 7.71-7.65 (m, 4H); 7.47-7.40 (m, 6H); 5.80-5.65 (m, 2H); 4.95 (m, 1H); 4.50-4.35 (m, 3H); 3.92-3.28 (m, 7H); 1.80-1.65 (m, 1.33H); 1.17 (m, 0.67H); 0.99 (s, 9H).

1.iii. (2R,3S,6R)-2-(tert-butyl-diphenyl-silanyloxymethyl)-6-((4RS)-2,2-dimethyl-[1,3]dioxolan-4-ylmethyl)-3,6-dihydro-2H-pyran-3-ol To a solution of intermediate 1.ii (34.83 g, 78.7 mmol) in DCM (575 ml) were added at rt PTSA (0.90 g, 4.7 mmol) and 2,2-dimethoxypropane (24 ml, 195.2 mmol). After 2 h., water (100 ml) and saturated NaHCO₃ (200 ml) were added and the two phases were separated. The aq. layer was extracted with DCM (260 ml). The yield after chromatography (Hex/EA 1:1) was 36.19 g (yellow oil). The compound was obtained as a 2:1 mixture of epimers.
¹H NMR (CDCl₃) δ: 7.72-7.67 (m, 4H); 7.50-7.39 (m, 6H); 5.85-5.77 (m, 2H); 4.23-3.41 (m, 8H); 2.80 (br s, 1H); 2.06 (m, 0.33H); 1.80-1.65 (1.67H); 1.40 (s, 3H); 1.33 (s, 3H); 1.09 (s, 9H).

1.iv. (2R,3S,6R)-2-(tert-butyl-diphenyl-silanyloxymethyl)-6-((4RS)-2,2-dimethyl-[1,3]dioxolan-4-ylmethyl)-tetrahydro-pyran-3-ol To a solution of intermediate 1.iii (36.16 g, 74.9 mmol) in EA (600 ml) was added platinum oxide hydrate (1.1 g, 4.8 mmol). The reaction mixture was stirred under hydrogen for 2 h. The catalyst was removed by filtration and the filtrate was concentrated to dryness to yield the title alcohol (36.18 g, 99% yield) as a thick oil. The compound was obtained as a 2:1 mixture of epimers.
MS (ESI, m/z): 485.2 [M+H⁺].

1.v. (2R,6S)-2-(tert-butyl-diphenyl-silanyloxymethyl)-6-((4RS)-2,2-dimethyl-[1,3]dioxolan-4-ylmethyl)-dihydro-pyran-3-one To a solution of intermediate 1.iv (12 g, 24.75 mmol) in DCM (100 ml) was added a solution of Dess-Martin periodinane (15 wt % in DCM, 50 ml). The mixture was stirred at rt for 4 h. The reaction mixture was diluted with DCM (30 ml) and washed with sat. NaHCO₃ (30 ml). The yield after work up and chromatography (Hex/EA 3:1) was 10.9 g (91%; colourless oil). The compound was obtained as a 2:1 mixture of epimers.
¹H NMR (CDCl₃) δ: 7.72-7.61 (m, 4H); 7.46-7.38 (m, 6H); 4.55 (m, 1H); 4.32 (m, 1H); 4.13-3.90 (m, 7H); 3.59 (m, 1H); 2.65-2.59 (m, 2H); 2.2-2.05 (m, 1.33H); 1.91-1.71 (m, 2.66H); 1.42 (s, 3H); 1.38 (s, 2H); 1.36 (s, 1H); 1.05 (s, 9H).

1.vi. tert-butyl-(2S,6S)-{6-[(4RS)-2,2-dim ethyl-[1,3]dioxolan-4-ylmethyl)-3-methylene-tetrahydro-pyran-2-ylmethoxy}-diphenyl-silane To a suspension of methyltriphenylphosphonium bromide (11.1 g, 31.0 mmol) in THF (75 ml), cooled to −78° C., was added n-BuLi (2.5N in Hex, 12.5 ml, 31.2 mmol). The mixture was stirred 15 min at this temperature and then 45 min at 0° C. After cooling to −78° C., a solution of intermediate 1.v (7.5 g, 15.5 mmol) in THF (25 ml) was added. The reaction was stirred for 1 h at the same temperature before gradual warming to rt. The reaction proceeded for 3 h. The reaction mixture was quenched by adding brine (100 ml). The two layers were separated and the aq. layer was extracted with EA (100 ml). The yield after chromatography (Hex/EA 5:1) was 7.3 g (99%; colourless oil). This compound was obtained as a 2:1 mixture of epimers.
¹H NMR (CDCl₃) δ: 7.72-7.67 (m, 4H); 7.46-7.38 (m, 6H); 4.85-4.79 (m, 2H); 4.26-4.22 (m, 2H); 4.12-3.71 (several m, 3H); 3.57 (t, J=7.8 Hz, 0.33H); 3.52 (t, J=8.0 Hz, 1H); 2.30 (m, 2H); 1.92 (m, 0.33H); 1.77-1.57 (m, 3.66H); 1.39 (s, 3H); 1.35 (s, 1H); 1.32 (s, 2H); 1.07 (s, 9H).

1.vii. (2R,3R,6S)-2-(tert-butyl-diphenyl-silanyloxymethyl)-6-((4RS)-2,2-dimethyl-[1,3]dioxolan-4-ylmethyl)-3-hydroxymethyl-tetrahydro-pyran-3-ol To a solution of intermediate 1.vi (7.4 g, 15.4 mmol) in 2-methyl-2-propanol (75 ml) and water (75 ml) were added AD mix β (22 g) and methanesulfonamide (1.9 g). The reaction mixture was stirred at rt for 20 h. Sodium bisulfite (25 g) was added. The two layers were decanted and the aq. layer was extracted with EA (200 ml). The yield after work up and chromatography (EA/Hept 3:2) was 6.0 g (75%; colourless oil). This compound was obtained as a 2:1 mixture of epimers.
¹H NMR (CDCl₃) δ: 7.71-7.66 (m, 4H); 7.50-7.40 (m, 6H); 4.17-3.41 (several m, 9H); 3.05 (br s, 1H); 2.75 (br s, 1H); 2.06 (m, 0.33H); 1.78-1.55 (m, 5.66H); 1.39 (s, 3H); 1.35 (s, 1H); 1.32 (s, 2H); 1.09 (s, 9H).

1.viii. Toluene-4-sulfonic acid (2R,3R,6S)-2-(tert-butyl-diphenyl-silanyloxymethyl)-6-(4RS)-2,2-dimethyl-[1,3]dioxolan-4-ylmethyl)-3-hydroxy-tetrahydro-pyran-3-ylmethyl ester To an ice-chilled solution of intermediate 1.vii (6 g, 11.65 mmol) in DCM (60 ml) were added 4-DMAP (2.15 g) and ρ-TsCl (2.7 g). The reaction was stirred at this temperature for 1 h. The reaction mixture was allowed to warm up to rt and the reaction proceeded for 2 h. At this point, DMAP (0.5 g) and ρ-TsCl (1 g) were added. After 2 h, the reaction mixture was concentrated to dryness and the residue was chromatographed (Hept/EA 2:1 then 1:2) to afford the title compound (4.8 g, 61% yield) as a colourless oil. This compound was obtained as a 2:1 mixture of epimers.
MS (ESI, m/z): 629.3 [M+H⁺].

1.ix. tert-butyl-(3R,4R,6S)[6-((4RS)-2,2-dim ethyl-[1,3]dioxolan-4-ylmethyl)-1,5-dioxa-spiro[2.5]oct-4-ylmethoxy]-diphenyl-silane:

To an ice-chilled solution of intermediate 1.viii (4.8 g, 7.17 mmol) in THF (70 ml) was added NaH (0.7 g). MeOH (4 ml) was added dropwise and the reaction proceeded for 2 h with warming to rt. The reaction mixture was quenched adding saturated NaHCO₃ (100 ml) and EA (200 ml). The two layers were decanted and the aq. layer was extracted once with EA (200 ml). The yield after chromatography (Hept/EA 2:1) was 3.77 g (colourless oil). This compound was obtained as a 2:1 mixture of epimers.
¹H NMR (CDCl₃) δ: 7.69-7.64 (m, 4H); 7.47-7.39 (m, 6H); 4.23-4.17 (m, 1H); 4.08-4.02 (m, 1H); 3.91-3.85 (m, t, J=7.8 Hz, 0.33H); 3.52 (t, J=7.9 Hz, 0.66H); 3.39 (m, 1H); 2.77 (d, J=4.3 Hz, 0.66H); 2.75 (d, J=4.3 Hz, 0.33H); 2.66 (d, J=4.3 Hz, 0.66H); 2.65 (d, J=4.3 Hz, 0.33H); 2.10 (m, 1H); 1.97 (m, 0.33H); 1.76-1.67 (m, 5.66H); 1.39 (s, 3H); 1.35 (s, 1H); 1.32 (s, 2H); 1.07 (s, 9H).
MS (ESI, m/z): 497.0 [M+H⁺].

1.x. (2R,3R,6S)-2-(tert-butyl-diphenyl-silanyloxymethyl)-3-[(2,3-dihydro-benzo[/, 4]dioxin-6-ylamino)-methyl]-6-((4RS)-2,2-dimethyl-[/, 3]dioxolan-4-ylmethyl)-tetrahydro-pyran-3-ol A solution of intermediate 1.ix (3.77 g, 7.6 mmol) and 2,3-dihydro-benzo[1,4]dioxin-6-ylamine (1.15 g, 1 eq.) in EtOH (27 ml) and water (3 ml) was heated at 90° C. for 40 h. After cooling, the solvent was removed in vacuo and the residue was chromatographed over $SiO_2$ (Hept/EA 2:1) to afford the title amino alcohol (3.2 g, 65% yield) contaminated with some of the unreacted aniline.
MS (ESI, m/z): 648.1 [M+H$^+$].

1.xi. (5R,6R,8S)-6-(tert-butyl-diphenyl-silanyloxymethyl)-3-(2,3-dihydro-benzo[/, 4]dioxin-6-yl)-8-((4RS)-2,2-dimethyl-[1,3]dioxolan-4-ylmethyl)-1,7-dioxa-3-aza-spiro[4.5]decan-2-one:

To an ice-chilled mixture of intermediate 1.x (3.2 g, 4.94 mmol) in DCM (25 ml) were added pyridine (1.2 ml) and trisphosgene (0.8 g). The reaction was stirred 1 h at 0° C. The reaction mixture was quenched by adding saturated NaHCO$_3$ (100 ml). The two layers were decanted and the org. layer was concentrated to dryness. The residue was taken up in EA (200 ml), washed with a sat. copper sulfate solution (100 ml), water (2×50 ml), and brine (100 ml), dried over Na$_2$SO$_4$, filtered and concentrated to dryness. The residue was chromatographed (Hept/EA 2:1) to afford the title oxazolidinone (2.3 g, 69% yield) as a colourless foam. This compound was obtained as a 2:1 mixture of epimers.
MS (ESI, m/z): 674.0 [M+H$^+$].

1.xii. 6-(tert-butyl-diphenyl-silanyloxymethyl)-3-(2,3-dihydro-benzo[1,4]dioxin-6-yl)-8-(2,3-dihydroxypropyl)-1,7-dioxa-3-aza-spiro[4.5]decan-2-one:

A solution of intermediate 1.xi (2.3 g, 3.41 mmol) in THF (5 ml), AcOH (15 ml) and water (5 ml) was heated at 60° C. for 4 h. After cooling, the reaction mixture was concentrated to dryness and the residue was partitioned between saturated NaHCO$_3$ and EA (200 ml). The aq. layer was further extracted with EA (200 ml). After work up 2.1 g of a brown foam were obtained. The material was carried on without further purification. This compound was obtained as a 2:1 mixture of epimers.
MS (ESI, m/z): 634.1 [M+H$^+$].

1.xiii. [(5R,6R,8S)-6-(tert-butyl-diphenyl-silanyloxymethyl)-3-(2,3-dihydro-benzo[/, 4]dioxin-6-yl)-2-oxo-1,7-dioxa-3-aza-spiro[4.5]dec-8-yl]-acetaldehyde:

To a solution of intermediate 1.xii (crude, 3.41 mmol) in acetone (30 ml) was added a solution of sodium periodate (1.82 g, 2.5 eq.) in water (10 ml). The reaction proceeded for 40 min. Water (100 ml) was added. The volatiles were removed in vacuo and the residue was extracted with EA (2×150 ml). The yield after chromatography (Hept-EA 1-1) was 2.0 g (97% yield; white solid).
$^1$H NMR (CDCl$_3$) δ: 9.77 (t, J=1.8 Hz, 1H); 7.69-7.64 (m, 4H); 7.50-7.39 (m, 6H); 7.00 (d, J=2.1 Hz, 1H); 6.88 (dd, J=2.1, 8.8 Hz, 1H); 6.81 (d, J=8.8 Hz, 1H); 4.34 (m, 1H); 4.29-4.24 (m, 4H); 4.00-3.92 (m, 4H); 3.42 (d, J=9.2 Hz, 1H); 2.76 (ddd, J=2.0, 7.6, 16.8 Hz, 1H); 2.51 (ddd, J=1.7, 5.2, 16.8 Hz, 1H); 2.11-1.72 (m, 4H); 1.07 (s, 9H).

1.xiv. (5R,6R,8S)-6-(tert-butyl-diphenyl-silanyloxymethyl)-3-(2,3-dihydro-benzo[/, 4]dioxin-6-yl)-8-((2R)-[2-hydroxy-2-(6-ethoxy-[1,5]naphthyridin-4-yl)-ethyl]-1,7-dioxa-3-aza-spiro[4.5]decan-2-one and (5R,6R,8S)-6-(tert-butyl-diphenyl-silanyloxymethyl)-3-(2,3-dihydro-benzo[1,4]dioxin-6-yl)-8-((2S)-[2-hydroxy-2-(6-methoxy-[1,5]naphthyridin-4-yl)-ethyl]-1,7-dioxa-3-aza-spiro[4.5]decan-2-one To a solution of 8-bromo-2-methoxy-[1,5]naphthyridine (1.2 g, 5 mmol; prepared according to WO 2006/032466) in THF (25 ml) was added at −78° C., n-BuLi (2.5N in Hex, 2 ml, 5 mmol). The mixture was stirred at the same temperature for 25 min and a solution of intermediate 1.xiii (2 g, 3.32 mmol) in THF (15 ml) was quickly added. The reaction proceeded 15 min and 10% NaHSO$_4$ (50 ml) was added. The reaction was then warmed to rt. The two layers were decanted and the aq. layer was extracted with EA (100 ml). The yield after work up and chromatography (Hept/EA 2:1) was 0.7 g (27%; yellowish foam) of a first isomer and 0.6 g of a second isomer (23%; yellowish foam) partially contaminated with its epimer.
First eluting isomer: MS (ESI, m/z): 762.0 [M+H$^+$].
Second eluting isomer: MS (ESI, m/z): 762.0 [M+H$^+$].

1.xv. (5R,6R,8S)-3-(2,3-dihydro-benzo[1,4]dioxin-6-yl)-8-[(2R)-2-hydroxy-2-(6-ethoxy-[1,5]naphthyridin-4-yl)-ethyl]-6-hydroxy ethyl-1,7-dioxa-3-aza-spiro[4.5]decan-2-one and (5R,6R,8S)-3-(2,3-dihydro-benzo[1,4]dioxin-6-yl)-8-[(2S)-2-hydroxy-2-(6-methoxy-[1,5]naphthyridin-4-yl)-ethyl]-6-hydroxymethyl-1,7-dioxa-3-aza-spiro[4.5]decan-2-one A solution of the first eluting isomer of intermediate 1.xiv (0.1 g, 0.13 mmol) in TFA-water (4-1, 2.5 ml) was stirred at rt overnight. After concentration to dryness, the residue was partitioned between saturated NaHCO$_3$ (10 ml) and EA (30 ml). Solid NaHCO$_3$ (0.2 g) was added. The two layers were decanted and the org. layer was dried over Na$_2$SO$_4$, filtered and concentrated to dryness. The residue was stirred for 20 min in MeOH and concentrated to dryness. The yield after chromatography (DCM/MeOH 19:1) was (0.045 g, 65% yield; white foam).
$^1$H NMR (d6-DMSO) δ: 8.79 (d, J=4.5 Hz, 1H); 8.27 (d, J=9.0 Hz, 1H); 7.78 (d, J=4.5 Hz, 1H); 7.27 (d, J=9.0 Hz, 1H); 7.10 (d, J=2.6 Hz, 1H); 6.97 (dd, J=2.6, 8.9 Hz, 1H); 6.84 (d, J=8.9 Hz, 1H); 5.62 (m, 1H); 5.44 (d, J=4.8 Hz, 1H); 4.75 (t, J=5.5 Hz, 1H); 4.23 (m, 4H); 4.12-4.06 (m, 2H); 4.03 (s, 3H); 3.71-3.65 (m, 2H); 3.60-3.51 (m, 2H); 2.16 (m, 1H); 2.05-1.77 (m, 5H).
MS (ESI, m/z): 523.8[M+H$^+$].

Starting from the second eluting isomer of intermediate 1.xiv (contaminated with its epimer, 0.1 g) and performing the same reaction sequence, the second epimer (0.048 g, 70% yield) was obtained as white foam. This compound was contaminated with traces of its epimer.
$^1$H NMR (d6-DMSO) δ: 8.78 (d, J=4.5 Hz, 1H); 8.26 (d, J=9.0 Hz, 1H); 7.78 (d, J=4.5 Hz, 1H); 7.26 (d, J=9.0 Hz, 1H); 7.11 (d, J=2.6 Hz, 1H); 6.98 (dd, J=2.6, 8.9 Hz, 1H); 6.85 (d, J=8.9 Hz, 1H); 5.76 (m, 1H); 5.42 (d, J=5.3 Hz, 1H); 4.78 (t, J=5.8 Hz, 1H); 4.23 (m, 4H); 4.12-4.06 (m, 2H); 4.05 (s, 3H); 3.91 (t, J=5.0 Hz, 1H); 3.71-3.62 (m, 3H); 2.40 (m, 1H); 2.00-1.96 (m, 2H); 1.75 (m, 1H); 1.63-1.49 (m, 2H).
MS (ESI, m/z): 523.8[M+H$^+$].

Example 2 cis-3-(2,3-dihydro-benzo[1,4]dioxin-6-yl)-8-(6-methoxy-quinolin-4-yloxymethyl)-1-oxa-3-aza-spiro[4.5]decan-2-one

2.i. cis/trans-4-[(2,3-dihydro-benzo[1,4]dioxin-6-ylamino)-methyl]-4-hydroxy cyclohexanecarboxylic acid ethyl ester A solution of 1-oxa-spiro[2.5]octane-6-carboxylic acid ethyl ester obtained according to *Tetrahedron*, 1995, 51, 10259-80, (4.5 g, 24.4 mmol) and 2,3-dihydro-benzo[1,4]dioxin-6-ylamine (3.7 g, 24.4 mmol) in EtOH/water (9:1, 100 ml) was heated at reflux overnight. The mixture was concentrated in vacuo and purified by chromatography (Hex:EA 2:1) to give the title amino alcohols (7.7 g, 94% yield) as an orange oil.

$^1$H NMR (DMSO d6) δ: 6.60-6.50 (m, 1H); 6.20-6.10 (m, 2H); 5.90-5.70 (m, 1H); 4.10-3.90 (m, 6H); 3.90-3.80 (m, 2H); 2.40-2.20 (m, 1H); 1.80-1.40 (m, 7H), 1.40-1.20 (m, 2H); 1.10-1.00 (m, 4H).

2.ii. cis and trans-3-(2,3-dihydro-benzo[1,4]dioxin-6-yl)-2-oxo-1-oxa-3-aza-spiro[4.5]decane-8-carboxylic acid ethyl ester Triphosgene (2.7 g, 9 mmol) was added portionwise to a solution of intermediate 2.i (7.7 g, 23 mmol) and TEA (9.6 ml, 69 mmol) in DCM (300 ml). The mixture was stirred at rt for 4 h, sat. NaHCO$_3$ was added and the mixture vigorously stirred for 15 min. The reaction mixture was diluted with DCM and worked up and chromatographed (Hex:EA 1:1) to give first trans compound (2 g) and then cis-derivative (4 g) as yellowish oils.

trans-isomer:
$^1$H NMR (DMSO d6) δ: 7.11 (d, J=2.5 Hz, 1H); 6.97 (dd, J=2.5, 8.8 Hz, 1H); 6.85 (d, J=8.8 Hz, 1H); 4.30-4.15 (m, 4H); 4.10-4.00 (m, 3H); 3.74 (s, 2H); 2.50-2.35 (m, 1H); 2.00-1.80 (m, 4H); 1.80-1.40 (m, 4H); 1.18 (t, J=7.1 Hz, 3H).

cis-isomer:
$^1$H NMR (DMSO d6) δ: 7.11 (d, J=2.5 Hz, 1H); 6.97 (dd, J=2.5, 8.8 Hz, 1H); 6.85 (d, J=8.8 Hz, 1H); 4.30-4.15 (m, 4H); 4.10-4.00 (m, 3H); 3.74 (s, 2H); 2.50-2.35 (m, 1H); 2.00-1.60 (m, 8H); 1.18 (t, J=7.1 Hz, 3H).

2.iii. cis-3-(2,3-dihydro-benzo[1,4]dioxin-6-yl)-2-oxo-1-oxa-3-aza-spiro[4.5]decane-8-carboxylic acid A mixture of intermediate 2.ii (cis isomer, 4 g, 11 mmol) and LiOH.H$_2$O (0.46 g, 11 mmol) in THF:MeOH:H$_2$O (2:2:1, 150 ml) was vigorously stirred at rt overnight. The mixture was acidified with 1M HCl and diluted with EA. The yield after work up was 3.24 g (88% yield; greyish solid).

$^1$H NMR (DMSO d6) δ: 7.11 (d, J=2.5 Hz, 1H); 6.97 (dd, J=2.5, 8.8 Hz, 1H); 6.85 (d, J=8.8 Hz, 1H); 4.30-4.15 (m, 4H); 4.10-4.00 (m, 1H); 3.74 (s, 2H); 2.20-2.05 (m, 1H); 2.00-1.60 (m, 8H).

2.iv. cis-3-(2,3-dihydro-benzo[/,4]dioxin-6-yl)-8-hydroxymethyl-1-oxa-3-aza-spiro[4.5]decan-2-one BH$_3$.THF complex (1M in THF, 6.7 ml) was added to a solution of intermediate 2.iii (1.5 g, 4.5 mmol) in THF. The mixture was stirred at rt for 3 h, carefully quenched with MeOH and concentrated in vacuo. The residue was several times dissolved in MeOH and re-concentrated. The product was finally crystallised from ether:EA to give the title alcohol (0.95 g, 66% yield) as a colourless solid.

$^1$H NMR (DMSO d6) δ: 7.14 (d, J=2.5 Hz, 1H); 7.02 (dd, J=2.5, 8.8 Hz, 1H); 6.85 (d, J=8.8 Hz, 1H); 4.49 (t, J=5.3 Hz, 1H); 4.30-4.15 (m, 4H); 3.79 (s, 2H); 3.30-3.15 (m, 2H); 2.00-1.50 (m, 6H); 1.50-1.35 (m, 1H); 1.20-1.00 (m, 2H).

2.v. cis-3-(2,3-dihydro-benzo[1,4]dioxin-6-yl)-8-(6-methoxy-quinolin-4-yloxymethyl)-1-oxa-3-aza-spiro[4.5]decan-2-one DIAD (0.22 ml, 1.1 mmol) was added dropwise to a solution of the alcohol 2.1 v (0.32 g, 1 mmol), 6-methoxy-quinolin-4-ol (0.265 g, 1 mmol) and triphenylphosphine (0.29 g, 1.1 mmol) in THF (15 ml). The mixture was stirred at rt overnight, concentrated in vacuo and purified by chromatography (EA:MeOH 9:1) and crystallised from ether/MeOH to give the title compound (0.14 g, 30% yield) as a beige solid.

$^1$H NMR (DMSO d6) δ: 8.57 (d, J=5.1 Hz, 1H); 7.87 (d, J=9.0 Hz, 1H); 7.45-7.35 (m, 2H); 7.11 (d, J=2.5 Hz, 1H); 7.05-6.90 (m, 2H); 6.85 (d, J=8.8 Hz, 1H); 4.30-4.15 (m, 4H); 4.15 (d, J=6.0 Hz, 2H); 3.90 (s, 3H); 3.76 (s, 2H); 2.10-1.95 (m, 3H); 1.95-1.80 (m, 2H); 1.80-1.65 (m, 2H); 1.65-1.50 (m, 2H).

MS (ESI, m/z): 476.7 [M+H$^+$].

Example 3 cis-3-(2,3-dihydro-benzo[1,4]dioxin-6-yl)-8-(6-methoxy-[1,5]naphthyridin-4-yloxymethyl)-1-oxa-3-aza-spiro[4.5]decan-2-one The title compound was prepared starting from intermediate 2.iv (1 mmol) and 6-methoxy-[1,5]naphthyridin-4-ol (1 mmol; prepared according to WO 2004/014361), using the procedure of Example 2, step 2.v. The title compound was isolated as a colourless solid (0.32 g, 68% yield).

$^1$H NMR (DMSO d6) δ: 8.60 (d, J=5.19 Hz, 1H); 8.20 (d, J=9.03 Hz, 1H); 7.25-7.18 (m, 2H); 7.11 (d, J=2.58 Hz, 1H); 6.97 (dd, J=2.64, 8.85 Hz, 1H); 6.85 (d, J=8.82 Hz, 1H); 4.30-4.15 (m, 4H); 4.14 (d, J=6.03 Hz, 2H); 4.02 (s, 3H); 3.76 (s, 2H); 2.10-1.95 (m, 3H); 1.95-1.80 (m, 2H); 1.80-1.50 (m, 4H).

MS (ESI, m/z): 477.7 [M+H$^+$].

Example 4

3-(2,3-dihydro-benzo[1,4]dioxin-6-yl)-8-[(2RS)-2-hydroxy-2-(6-methoxy-quinolin-4-yl)-ethyl]-1-oxa-3,8-diaza-spiro[4.5]decan-2-one

4.i. 4-[(2,3-dihydro-benzo[1,4]dioxin-6-ylamino)-methyl]-4-hydroxy-piperidine-1-carboxylic acid benzyl ester The title compound was obtained as an orange oil from a 1-oxa-6-aza-spiro[2.5]octane-6-carboxylic acid benzyl ester (prepared as in U.S. Pat. No. 4,353,901; 0.495 g; 2 mmol) and 2,3-dihydro-benzo[1,4]dioxin-6-ylamine (0.30 g, 2 mmol) following the procedure of Example 2, step 2.i. The yield after work up and chromatography (eluent: Hex/EA 2:1, 1:1) was 0.61 g (77%).

MS (ESI, m/z): 291.2 [M+H$^+$].

4.ii. 3-(2,3-dihydro-benzo[1,4]dioxin-6-yl)-2-oxo-1-oxa-3,8-diaza-spiro[4.5]decane-8-carboxylic acid benzyl ester The title compound (0.34 g, 100%) was prepared following the procedure of Example 2, step 2.ii, starting from the amino alcohol 4.i (0.30 g, 0.75 mmol) and triphosgene.
$^1$H NMR (CDCl$_3$) δ: 7.45-7.30 (m, 5H); 7.08 (d, J=2.6 Hz, 1H); 6.98 (dd, J=2.6, 8.8 Hz, 1H); 6.85 (d, J=8.8 Hz, 1H); 5.16 (s, 2H); 4.30-4.15 (m, 4H); 4.10-3.90 (br, 2H); 3.70 (s, 2H); 3.60-3.30 (m, 2H); 2.10-1.90 (m, 2H); 1.90-1.60 (m, 2H).

4.iii. 3-(2,3-dihydro-benzo[1,4]dioxin-6-yl)-1-oxa-3,8-diaza-spiro[4.5]decan-2-one A solution of intermediate 4.ii (0.34 g, 0.8 mmol) in EA (50 ml) was hydrogenated under H$_2$ normal atmosphere using 10% Pd/C (0.085 g, 0.1 eq) for 6 h. The catalyst was filtered off and the filtrate concentrated in vacuo. The title amine (0.12 g, 51% yield) was isolated as a brownish oil.
MS (ESI, m/z): 291.2 [M+H$^+$].

4.iv. 3-(2,3-dihydro-benzo[1,4]dioxin-6-yl)-8-[(2RS)-2-hydroxy-2-(6-methoxy-quinolin-4-yl)-ethyl]-1-oxa-3,8-diaza-spiro[4.5]decan-2-one A mixture of intermediate 4.iii (0.12 g, 0.4 mmol), 6-methoxy-4-oxiranyl-quinoline (0.083 g, 0.4 mmol, prepared according to WO 00/78748), K$_2$CO$_3$ (0.08 g, 0.58 mmol) and LiClO$_4$ (0.048 g, 0.46 mmol) in DMF (4 ml) was heated at 90° C. overnight. The mixture was poured into water and diluted with EA. The yield after work up and chromatography (EA: MeOH 9:1 containing 1% NH$_4$OH) was 0.065 g (32% yield; beige foam).
$^1$H NMR (DMSO d6) δ: 8.73 (d, J=4.5 Hz, 1H); 7.94 (dd, J=1.65, 8.1 Hz, 1H); 7.59 (d, J=4.5 Hz, 1H); 7.45-7.35 (m, 2H); 7.11 (d, J=2.5 Hz, 1H); 7.00 (dd, J=2.6, 8.8 Hz, 1H); 6.85 (d, J=8.8 Hz, 1H); 5.49 (br, 2H); 4.30-4.15 (m, 4H); 3.92 (s, 3H); 3.78 (s, 2H); 2.80-2.60 (m, 6H); 1.95-1.80 (m, 4H).

Example 5

6-{8-[(2RS)-2-hydroxy-2-(6-methoxy-quinolin-4-yl)-ethyl]-2-oxo-1-oxa-3,8-diaza-spiro[4.5]dec-3-yl}-4H-benzo[1,4]thiazin-3-one

5.i. 4-hydroxy-4-[(3-oxo-3,4-dihydro-2H-benzo[1,4]thiazin-6-ylamino)-methyl]-piperidine-1-carboxylic acid benzyl ester The title compound was obtained as a yellowish foam starting from 1-oxa-6-aza-spiro[2.5]octane-6-carboxylic acid benzyl ester (prepared according to U.S. Pat. No. 4,353,901; 0.366 g; 1.4 mmol) and 6-amino-4H-benzo[1,4]thiazin-3-one (0.267 g, 1.4 mmol) following the procedure of Example 2, step 2.i. The yield after work up and chromatography (eluent: Hex:EA 1:1 then EA) was 0.57 g (90%).
MS (ESI, m/z): 427.9 [M+H$^+$].

5.ii. 2-oxo-3-(3-oxo-3,4-dihydro-2H-benzo[1,4]thiazin-6-yl)-1-oxa-3,8-diaza-spiro[4.5]decane-8-carboxylic acid benzyl ester The title compound (0.27 g, 67% yield) was prepared as a colourless solid, starting from intermediate 5.i (0.3 g, 0.75 mmol) and triphosgene and using the procedure of Example 2, step 2.ii.
MS (ESI, m/z): 453.9 [M+H$^+$].

5.iii. 6-(2-oxo-1-oxa-3,8-diaza-spiro[4.5]dec-3-yl)-4H-benzo[1,4]thiazin-3-one A solution of intermediate 5.ii (0.26 g, 0.58 mmol) in TFA (6 ml) was stirred at rt for 30 h. The mixture was concentrated in vacuo, partitioned between DCM and NH$_4$OH and worked up to give the title amine (0.19 g, 100% yield) as a yellowish solid.
MS (ESI, m/z): 319.9 [M+H$^+$].

5.iv. 6-{8-[(2RS)-2-hydroxy-2-(6-methoxy-quinolin-4-yl)-ethyl]-2-oxo-1-oxa-3,8-diaza-spiro[4.5]dec-3-yl}-4H-benzo[1,4]thiazin-3-one The title compound (0.027 g, 9% yield) was obtained as a beige solid, starting from the amine 5.iii (0.19 g, 0.59 mmol) and 6-methoxy-4-oxiranyl-quinoline (0.59 mmol) and following the procedure of Example 4, step 4.iv.
MS (ESI, m/z): 521.0 [M+H$^+$].

Example 6

(5RS, 6RS)-6-allyl-3-(2,3-dihydro-benzo[1,4]dioxin-6-yl)-8-[(2RS)-2-hydroxy-2-(6-methoxy-quinolin-4-yl)-ethyl]-1-oxa-3,8-diaza-spiro[4.5]decan-2-one

6.i. (3RS,4RS)-4-allyl-1-oxa-6-aza-spiro[2.5]octane-6-carboxylic acid tert-butyl ester A solution of (3RS)-3-allyl-4-oxo-piperidine-1-carboxylic acid tert-butyl ester (2 g, 8.3 mmol, prepared according to EP 438 233) in MeCN (30 ml) was treated with KOH (3.28 g, 58.5 mmol) and trimethylsulfonium iodide (1.78 g, 8.77 mmol). The mixture was stirred at 65° C. for 30 min. The mixture was cooled to rt, filtered over Celite and concentrated. The residue was purified by chromatography (Hex/EA 9:1) to give the title epoxide (1.2 g, 57% yield) as a colourless oil.
$^1$H NMR (CDCl$_3$) δ: 5.90-5.60 (m, 1H); 5.15-5.05 (m, 2H); 4.20-3.40 (m, 4H); 3.00-2.80 (m, 2H); 2.60-2.40 (m, 4H); 2.20-2.00 (m, 1H); 1.51 (s, 9H).

6.ii. (3RS, 4RS)-3-allyl-4-[(2,3-dihydro-benzo[1,4]dioxin-6-ylamino)-methyl]-4-hydroxy-piperidine-1-carboxylic acid tert-butyl ester The title compound was obtained as a yellowish oil, starting from intermediate 6.i (0.6 g, 2.4 mmol) and 2,3-dihydro-benzo[1,4]dioxin-6-ylamine (0.358 g, 2 mmol) and following the procedure of Example 2, step 2.i. The yield after work up and chromatography (eluent: Hex/EA 4:1 then 2:1) was 0.45 g (47%).
$^1$H NMR (CDCl$_3$) δ: 6.75-6.70 (m, 1H); 6.35-6.25 (m, 2H); 5.95-5.75 (m, 1H); 5.20-5.00 (m, 2H); 4.30-4.20 (m 4H); 3.90-3.70 (m, 1H); 3.40-3.00 (m, 4H), 2.40-2.30 (m, 1H), 2.00-1.60 (m, 6H), 1.47 (s, 9H).

6.iii. (5RS,6RS)-6-allyl-3-(2,3-dihydro-benzo[1,4]dioxin-6-yl)-2-oxo-1-oxa-3,8-diaza-spiro[4.5]decane-8-carboxylic acid tert-butyl ester The title compound (0.55 g, 100% yield) was prepared following the procedure of Example 2, step 2.ii, starting from intermediate 6.ii (0.45 g, 1.1 mmol) and triphosgene. It was recovered as a brownish oil and used crude without purification in the next step.

$^1$H NMR (CDCl$_3$) δ: 7.09 (d, J=2.6 Hz, 1H); 7.01 (dd, J=2.6, 8.8 Hz, 1H); 6.88 (d, J=8.8 Hz, 1H); 5.95-5.65 (m, 1H); 5.20-5.00 (m, 2H); 4.30-4.20 (m, 4H); 4.00-3.80 (m, 2H); 3.65-3.55 (m, 1H); 3.30-2.80 (m, 2H), 2.40-1.90 (m, 3H), 1.80-1.60 (m, 2H), 1.47 (s, 9H).

6.iv. (5RS, 6RS)-6-allyl-3-(2,3-dihydro-benzo[1,4]dioxin-6-yl)-1-oxa-3,8-diaza-spiro[4.5]decan-2-one A solution of intermediate 6.iii (0.48 g, 1.1 mmol) was dissolved in DCM (10 ml) and treated with TFA (2 ml). The mixture was stirred at rt for 2 h, concentrated in vacuo, partitioned between DCM and NH$_4$OH and worked up to give 0.37 g (100% yield) of an orange oil.

$^1$H NMR (CDCl$_3$) δ: 7.09 (d, J=2.6 Hz, 1H); 7.01 (dd, J=2.6, 8.8 Hz, 1H); 6.88 (d, J=8.8 Hz, 1H); 5.95-5.75 (m, 1H); 5.20-5.00 (m, 2H); 4.30-4.20 (m, 4H); 4.00-3.80 (m, 1H); 3.70-3.60 (m, 1H); 3.20-3.00 (m, 2H), 2.90-2.75 (m, 1H), 2.40-1.80 (m, 6H).

6.v. (5RS,6RS)-6-allyl-3-(2,3-dihydro-benzo[1,4]dioxin-6-yl)-8 [(2RS)2 hydroxy-2-(6-methoxy-quinolin-4-yl)-ethyl]-1-oxa-3,8-diaza-spiro[4.5]decan-2-one The title compound was obtained following the procedure of Example 4, step 4.iv, starting from amine 6.iv (0.37 g, 1.1 mmol) and 6-methoxy-4-oxiranyl-quinoline (1.1 mmol). The title compound (0.3 g, 51% yield) was obtained as a yellow oil after chromatography
(EA:MeOH 9:1 containing 1% NH$_4$OH).
MS (ESI, m/z): 531.7 [M+H$^+$].

Example 7

(5RS,6RS)-{3-(2,3-dihydro-benzo[1,4]dioxin-6-yl)-8-[(2RS)-2-hydroxy-2-(6-methoxy-quinolin-4-yl)-ethyl]-2-oxo-1-oxa-3,8-diaza-spiro[4.5]dec-6-yl}-acetic acid methyl ester (mixture of isomers)

7.i. (3RS)-3-tert-butoxycarbonylmethyl-4-oxo-piperidine-1-carboxylic acid tert-butyl ester To a solution of diisopropylamine (13.5 ml, 96 mmol) in THF (300 ml) at −78° C. was added dropwise n-BuLi (2.5M in Hex, 32 ml). The mixture was warmed to −10° C. and re-cooled to −78° C. A solution of 4-oxo-piperidine-1-carboxylic acid tert-butyl ester (10 g, 50 mmol) in THF (50 ml) was then added dropwise and the mixture stirred at −78° C. for another 15 min. A solution of tert-butyl bromoacetate (12.6 ml, 85 mmol) in THF (30 ml) and HMPT (5 ml) was then added dropwise and the mixture stirred at −78° C. for 4 h and then gradually warmed to rt. The mixture was taken up in sat. aq. NH$_4$Cl and extracted with EA. The yield after work up and chromatography (eluent Hex/EA 4:1) was 7.6 g (50.6%; yellowish oil).

$^1$H NMR (CDCl$_3$) δ: 4.40-4.20 (m, 2H); 3.25-3.15 (m, 1H); 3.00-2.80 (m, 2H); 2.70-2.40 (m, 3H); 2.30-2.10 (m, 1H); 1.51 (s, 9H), 1.46 (s, 9H).

7.ii. (3RS)-3-tert-butoxycarbonylmethyl-4-methylene-piperidine-1-carboxylic acid tert-butyl ester Methyltriphenylphosphonium bromide (8.5 g, 23.9 mmol) was suspended in THF (23 ml) and treated with KOtBu (2.7 g, 23.9 mmol). The resulting yellow suspension was stirred at rt for 1 h. A solution of the intermediate 7.i (3.0 g, 9.6 mmol) in THF was added dropwise and the mixture was stirred at rt for 2 h, taken up in water and diluted with ether. The yield after work up and chromatography (Hex:EA 9:1) was 1.8 g (60%; colourless oil).

$^1$H NMR (CDCl$_3$) δ: 4.80 (s, 1H); 4.75 (s, 1H); 4.60-4.20 (m, 4H); 2.80-2.60 (m, 1H); 2.50-2.25 (m, 3H); 2.25-2.10 (m, 1H); 1.48 (s, 9H); 1.46 (s, 9H).

7.iii. (3RS, 4RS)-4-tert-butoxycarbonylmethyl-1-oxa-6-aza-spiro[2.5]octane-6-carboxylic acid tert-butyl ester MCPBA (70%, 1.7 g, 6.9 mmol) was added to a solution of intermediate 7.ii (1.8 g, 5.8 mmol) in DCM (34 ml), water (40 ml) and 1M phosphate buffer (pH 8, 22.5 ml). The mixture was vigorously stirred at rt for 2 days. The yield after work up and chromatography (Hex/EA 4:1) was 1.65 g (87%; colourless oil).

$^1$H NMR (CDCl$_3$) δ: 4.00-3.00 (m, 4H); 2.77 (t, J=4.4 Hz, 1H); 2.65 (t, J=4.4 Hz, 1H); 2.30-1.6 (m, 5H); 1.48 (s, 9H); 1.46 (s, 9H).

7.iv. (3RS,4RS)-3-tert-butoxycarbonylmethyl-4-[(2,3-dihydro-benzo[1,4]dioxin-6-ylamino)-methyl]-4-hydroxy-piperidine-1-carboxylic acid tert-butyl ester The title compound was obtained as an orange oil from the epoxide 7.iii (1.65 g, 5.04 mmol) and 2,3-dihydro-benzo[1,4]dioxin-6-ylamine (0.762 g, 5.04 mmol), using the procedure of Example 2, step 2.i. The yield after work up and chromatography (eluent Hex/EA 2:1) was 1.9 g (79%).

$^1$H NMR (CDCl$_3$) δ: 6.70-6.60 (m, 1H); 6.30-6.10 (m, 2H); 4.25-4.10 (m, 4H); 3.70-3.60 (m, 1H); 3.40-2.90 (m, 3H); 2.60-2.50 (m, 1H); 2.40-2.20 (m, 1H); 1.80-1.60 (m, 3H); 1.48 (s, 9H); 1.46 (s, 9H).

7.v. (5RS,6RS)-6-tert-butoxycarbonylmethyl-3-(2,3-dihydro-benzo[1,4]dioxin-6-yl)-2-oxo-1-oxa-3,8-diaza-spiro[4.5]decane-8-carboxylic acid tert-butyl ester The title compound (1.2 g, 60% yield) was prepared starting from the intermediate 7.iv (1.9 g, 3.97 mmol) and triphosgene, using the procedure of Example 2, step 2.ii. It was recovered as a beige solid after chromatography (Hex:EA 2:1).

$^1$H NMR (CDCl$_3$) δ: 7.10-7.05 (m, 1H); 7.00-6.95 (m, 1H); 6.86 (d, J=8.8 Hz, 1H); 4.30-4.25 (m, 4H); 3.90-3.20 (m, 5H); 3.20-3.00 (m, 1H); 2.50-1.50 (m, 6H); 1.48 (s, 9H); 1.43 (s, 9H).

7.vi. (5RS, 6RS)-[3-(2,3-dihydro-benzo[1,4]dioxin-6-yl)-2-oxo-1-oxa-3,8-diaza-spiro[4.5]dec-6-yl]-acetic acid methyl ester A solution of intermediate 7.v (1.7 g, 3.36 mmol) in MeOH (15 ml) was treated with a sat. solution of HCl in MeOH (15 ml). The mixture was stirred at rt for 3 h and at 60° C. for 90 min. The mixture was concentrated in vacuo, partitioned between NH$_4$OH and DCM. The yield after work up and chromatography (EA:MeOH 9:1 containing 1% NH$_4$OH) was 1 g (83%; colourless foam).

$^1$H NMR (CDCl$_3$) δ: 7.09 (d, J=2.6 Hz, 1H); 7.01 (dd, J=2.6, 8.8 Hz, 1H); 6.87 (d, J=8.8 Hz, 1H); 4.30-4.20 (m, 4H);

4.00-3.80 (m, 1H); 3.70-3.60 (m, 1H); 3.20-2.80 (m, 3H); 2.60-2.20 (m, 3H), 2.10-1.70 (m, 2H).

7.vii. (5RS, 6RS)-{3-(2,3-dihydro-benzo[1,4]dioxin-6-yl)-8-[(2RS)-2-hydroxy-2-(6-methoxy-quinolin-4-yl)-ethyl]-2-oxo-1-oxa-3,8-diaza-spiro[4.5]dec-6-yl}-acetic acid methyl ester (mixture of isomers)

Starting from intermediate 7.vi (0.9 g, 2.5 mmol) and 6-methoxy-4-oxiranyl quinoline, and using the procedure of Example 4, step 4.iv, the title compound (1.1 g, 78% yield) was obtained after chromatography (eluent EA:MeOH 9:1 containing 1% NH$_4$OH) as a beige solid.
MS (ESI, m/z): 563.8 [M+H$^+$].

Example 8

(5RS, 6RS)-3-(2,3-dihydro-benzo[1,4]dioxin-6-yl)-6-(2-hydroxy-ethyl)-8-[(2RS)-2-hydroxy-2-(6-methoxy-quinolin-4-yl)-ethyl]-1-oxa-3,8-diaza-spiro[4.5]decan-2-one (mixture of isomers)

A solution of compound 7.vii (0.2 g, 0.35 mmol) in THF (5 ml) was treated with LiBH$_4$ (15 mg, 2 eq). The mixture was stirred at rt for 3 h and at 80° C. for 3 h. A tip of a spatula of LiAlH$_4$ was added and the mixture stirred at rt for 1 h, quenched with 2 drops of dilute HCl, filtered over Celite and concentrated. The yield after chromatography (eluent: EA:MeOH 9:1 containing 1% NH$_4$OH) was 0.1 g (colourless foam).
MS (ESI, m/z): 537 [M+H$^+$].

Example 9 cis/trans-3-(2,3-dihydro-benzo[1,4]dioxin-6-yl)-2-oxo-1-oxa-3-aza-spiro[4.5]decane-8-carboxylic acid (6-methoxy-[1,5]naphthyridin-4-yl)-amide A solution of 6-methoxy-[1,5]naphthyridin-4-ylamine (0.158 g, 0.9 mmol) and intermediate 2.vi (0.3 g, 0.9 mmol) in pyridine (5 ml) was cooled to −20° C. and POCl$_3$ (0.1 ml, 1.2 eq) was added dropwise. The mixture was stirred at this temperature for 1 h and then gradually warmed to rt. The resulting thick suspension was diluted with water and filtered. The crystals were washed with EtOH and ether and dried under HV to give the title compound (0.29 g, 66% yield) as a colourless solid.
$^1$H NMR (DMSO d6) δ: 9.83 (s, 1H); 8.69 (d, J=5.1 Hz, 1H); 8.43 (d, J=5.1 Hz, 1H); 8.28 (d, J=9.1 Hz, 1H); 7.32 (d, J=9.1 Hz, 1H); 7.12 (d, J=2.6 Hz, 1H); 6.98 (dd, J=2.6, 8.9 Hz, 1H); 8.87 (d, J=8.9 Hz, 1H); 4.30-4.20 (m, 4H); 4.16 (s, 3H); 3.78 (s, 2H); 3.90-3.80 (m, 1H); 2.10-1.60 (m, 8H).
MS (ESI, m/z): 490.6 [M+H$^+$].

Example 10 cis or trans-3-(2,3-dihydro-benzo[1,4]dioxin-6-yl)-8-hydroxy-8-[2-(6-methoxy-[1,5]naphthyridin-4-yl)-ethyl]-1-oxa-3-aza-spiro[4.5]decan-2-one (isomer 1)

10.i. cis/trans-6-[2-(6-Methoxy-[/, 5]naphthyridin-4-yl)-ethyl]-1-oxa-spiro[2.5]octan-6-ol The title compound (1.83 g; 87% yield) was obtained as a colourless solid starting from cis/trans-4-hydroxy-4-[2-(6-methoxy-[1,5]naphthyridin-4-yl)-ethyl]-cyclohexanone (2.0 g; 6.6 mmol; prepared according to WO 2004/035569) and trimethylsulfonium iodide (1.43 g, 1.05 eq) and using the procedure of Example 6, step 6.i.
$^1$H NMR (DMSO d6) δ: 8.66 (d, J=4.5 Hz, 1H); 8.24 (d, J=9.0 Hz, 1H); 7.54 (d, J=4.5 Hz, 1H); 7.24 (d, J=9.0 Hz, 1H); 4.34 and 4.31 (s, 1H); 4.03 (s, 3H); 3.30-3.10 (m, 2H); 2.59 and 2.54 (s, 2H); 2.20-2.00 (m, 2H); 1.90-1.50 (m, 6H); 1.20-1.00 (m, 2H).

10.ii. cis and trans-1-[(2,3-dihydro-benzo[1,4]dioxin-6-ylamino)-methyl]-4-[2-(6-methoxy-[1,5] naphthyridin-4-yl)-ethyl]-cyclohexane-1,4-diol Intermediate 10.i (0.9 g, 2.86 mmol) and 2,3-dihydro-benzo[1,4]dioxin-6-ylamine (0.432 g, 2.86 mmol) in EtOH/H$_2$O (9:1, 10 ml) were reacted following the procedure of Example 2, step 2.i. The mixture was concentrated in vacuo and purified by chromatography (EA/MeOH 9:1) to give 0.61 g of isomer 1 and 0.11 g of isomer 2, each as a colourless foam.
Isomer 1:
$^1$H NMR (DMSO d6) δ: 8.66 (d, J=4.5 Hz, 1H); 8.24 (d, J=9.0 Hz, 1H); 7.53 (d, J=4.5 Hz, 1H); 7.24 (d, J=9.0 Hz, 1H); 6.56 (dd, J=1.6, 7.4 Hz, 1H); 6.20-6.10 (m, 2H); 4.85 (t, J=5.9 Hz, 1H); 4.20-4.00 (m, 6H); 4.03 (s, 3H); 3.30-3.10 (m, 2H); 2.86 (d, J=5.9 Hz, 2H); 1.80-1.60 (m, 6H); 1.55-1.35 (m, 4H).
MS (ESI, m/z): 466.0 [M+H$^+$].
Isomer 2:
$^1$H NMR (DMSO d6) δ: 8.66 (d, J=4.5 Hz, 1H); 8.24 (d, J=9.0 Hz, 1H); 7.53 (d, J=4.5 Hz, 1H); 7.24 (d, J=9.0 Hz, 1H); 6.56 (dd, J=1.6, 7.4 Hz, 1H); 6.20-6.10 (m, 2H); 4.85 (t, J=5.9 Hz, 1H); 4.20-4.00 (m, 6H); 4.03 (s, 3H); 3.30-3.10 (m, 2H); 2.86 (d, J=5.9 Hz, 2H); 1.80-1.60 (m, 6H); 1.55-1.35 (m, 4H).
MS (ESI, m/z): 466.0 [M+H$^+$].

10.iii. cis or trans-3-(2,3-dihydro-benzo[1,4]dioxin-6-yl)-8-hydroxy-8 [2 (6 methoxy-[1,5]naphthyridin-4-yl)-ethyl]-1-oxa-3-aza-spiro[4.5]decan-2-one (isomer 1)

The title compound was obtained as a beige solid, starting from intermediate 10.ii (isomer 1, 0.60 g, 1.23 mmol) and triphosgene (0.153 g, 0.4 eq) and using the procedure of Example 2, step 2.ii. The yield after work up and stirring in ether was 0.63 g (99% yield).
$^1$H NMR (DMSO d6) δ: 8.69 (d, J=4.5 Hz, 1H); 8.24 (d, J=9.0 Hz, 1H); 7.59 (d, J=4.5 Hz, 1H); 7.27 (d, J=9.0 Hz, 1H); 7.12 (d, J=2.6 Hz, 1H); 6.98 (dd, J=2.6, 8.9 Hz, 1H); 6.86 (d, J=8.9 Hz, 1H); 4.30-4.20 (m, 4H); 4.05 (s, 3H); 3.76 (s, 2H); 3.30-3.10 (m, 2H); 2.05-1.60 (m, 10H).
MS (ESI, m/z): 492.0 [M+H$^+$].

Example 11 cis or trans-3-(2,3-dihydro-benzo[1,4]dioxin-6-yl)-8-hydroxy-8-[2-(6-methoxy-[1,5]naphthyridin-4-yl)-ethyl]-1-oxa-3-aza-spiro[4.5]decan-2-one (isomer 2)

This compound was obtained as a beige solid from intermediate 10.ii. (isomer 2, 0.1 g, 0.2 mmol) and triphosgene (0.025 g, 0.4 eq) following the procedure of Example 2, step 2.ii. The yield after work up and stirring of the crude material in ether was 0.09 g (85%).
$^1$H NMR (DMSO d6) δ: 8.69 (d, J=4.5 Hz, 1H); 8.25 (d, J=9.0 Hz, 1H); 7.58 (d, J=4.5 Hz, 1H); 7.27 (d, J=9.0 Hz, 1H); 7.12 (d, J=2.6 Hz, 1H); 7.02 (dd, J=2.6, 8.9 Hz, 1H); 6.86 (d, J=8.9 Hz, 1H); 4.30-4.20 (m, 4H); 4.05 (s, 3H); 3.81 (s, 2H); 3.30-3.10 (m, 2H); 2.10-2.00 (m, 2H); 1.90-1.60 (m, 8H).
MS (ESI, m/z): 492.0 [M+H$^+$].

Example 12 cis or trans-6-{8-hydroxy-8-[2-(6-methoxy-[1,5] naphthyridin-4-yl)-ethyl]-2-oxo-1-oxa-3-aza-spiro [4.5]dec-3-yl}-4H-benzo[1,4]thiazin-3-one (isomer 1)

12.i. cis and trans 6-({1,4-dihydroxy-4-[2-(6-methoxy-[1,5]naphthyridin-4-yl)-ethyl]-cyclohexylmethyl}-amino)-4H-benzo[1,4]thiazin-3-one The title compound was obtained as a beige solid, starting from intermediate 10.i (1.5 g, 4.8 mmol) and 6-amino-4H-benzo[1,4]thiazin-3-one (0.86 g, 4.8 mmol) and following the procedure of Example 2, step 2.i. The yield after work up and chromatography (eluent: EA/MeOH 9:1) was 0.90 g of isomer 1 and 0.24 g of isomer 2.
Isomer 1: MS (ESI, m/z): 494.8[M+H$^+$].
Isomer 2: MS (ESI, m/z): 494.8[M+H$^+$].

12.ii. cis or trans-6-{8-hydroxy-8-[2-(6-ethoxy-[1,5] naphthyridin-4-yl)-ethyl]-2-oxo-1-oxa-3-aza-spiro [4.5]dec-3-yl}-4H-benzo[1,4]thiazin-3-one (isomer 1)

The title compound (0.5 g, 53% yield) was obtained as a beige solid, starting from compound 12.i (isomer 1, 0.9 g, 1.8 mmol) and triphosgene and using the procedure of Example 2, step 2.i.
$^1$H NMR (DMSO d6) δ: 10.58 (s, 1H); 8.68 (d, J=4.5 Hz, 1H); 8.24 (d, J=9.0 Hz, 1H); 7.56 (d, J=4.5 Hz, 1H); 7.40 (d, J=2.3 Hz, 1H); 7.32 (d, J=8.5 Hz, 1H); 7.23 (d, J=9.0 Hz, 1H); 7.07 (dd, J=2.3, 8.5 Hz, 1H); 4.34 (s, 1H); 4.05 (s, 3H); 3.81 (s, 2H); 3.41 (s, 2H); 3.30-3.10 (m, 2H); 2.50-2.40 (br, 1H); 2.05-1.60 (m, 10H).
MS (ESI, m/z): 520.9 [M+H$^+$].

Example 13 cis or trans-6-{8-hydroxy-8-[2-(6-methoxy-[1,5] naphthyridin-4-yl)-ethyl]-2-oxo-1-oxa-3-aza-spiro [4.5]dec-3-yl}-4H-benzo[1,4]thiazin-3-one (isomer 2)

The title compound (0.066 g, 26% yield) was obtained as a beige solid using the procedure of Example 2, step 2.ii, starting from the isomer 2 obtained at step 12.i of Example 12 (0.24 g, 0.48 mmol) and triphosgene.
$^1$H NMR (DMSO d6) δ: 10.58 (s, 1H); 8.68 (d, J=4.5 Hz, 1H); 8.24 (d, J=9.0 Hz, 1H); 7.56 (d, J=4.5 Hz, 1H); 7.40 (d, J=2.3 Hz, 1H); 7.32 (d, J=8.5 Hz, 1H); 7.23 (d, J=9.0 Hz, 1H); 7.07 (dd, J=2.3, 8.5 Hz, 1H); 4.34 (s, 1H); 4.05 (s, 3H); 3.84 (s, 2H); 3.41 (s, 2H); 3.30-3.10 (m, 2H); 2.50-2.40 (br, 1H); 2.05-1.60 (m, 10H).
MS (ESI, m/z): 520.9 [M+H$^+$].

Example 14 cis or trans-6-{8-hydroxy-8-[2-(6-methoxy-[1,5] naphthyridin-4-yl)-ethyl]-2-oxo-1-oxa-3-aza-spiro [4.5]dec-3-yl}-4H-benzo[1,4]oxazin-3-one (isomer 1)

14.i. cis and trans 6-({1,4-dihydroxy-4-[2-(6-methoxy-[1,5]naphthyridin-4-yl)-ethyl]-cyclohexylmethyl}-amino)-4H-benzo[1,4]oxazin-3-one The title compounds were obtained as beige solids starting from intermediate 10.i (0.5 g, 1.6 mmol) and 6-amino-4H-benzo[1,4]oxazin-3-one (0.26 g, 1.6 mmol) following the procedure of Example 2, step 2.i. After work up and chromatography (eluent: EA/MeOH 9:1), 0.22 g of isomer 1 and 0.08 g of isomer 2 were obtained.
Isomer 1: MS (ESI, m/z): 487.8 [M+H$^+$].
Isomer 2: MS (ESI, m/z): 487.8 [M+H$^+$].

14.ii. cis or trans-6-{8-hydroxy-8-[2-(6-ethoxy-[1,5] naphthyridin-4-yl)-ethyl]-2-oxo-1-oxa-3-aza-spiro [4.5]dec-3-yl}-4H-benzo[1,4]oxazin-3-one (isomer 1)

The title compound (0.080 g, 76% yield) was obtained as a beige solid, starting from the isomer 1 obtained in Example 14, step 14.i (0.1 g, 0.21 mmol) and triphosgene and using the procedure of Example 2, step 2.ii.
MS (ESI, m/z): 505.0 [M+H$^+$].

Example 15 cis or trans-6-{8-hydroxy-8-[2-(6-methoxy-[1,5] naphthyridin-4-yl)-ethyl]-2-oxo-1-oxa-3-aza-spiro [4.5]dec-3-yl}-4H-benzo[1,4]oxazin-3-one (isomer 2)

The title compound (0.014 g, 17% yield) was prepared as a beige solid, starting from the isomer 2 obtained in Example 14, step 14.i (0.08 g, 0.17 mmol) and triphosgene and using the procedure of Example 2, step 2.ii.
MS (ESI, m/z): 504.9 [M+H$^+$].

Example 16 cis/trans-6-{8-[2-(6-methoxy-[1,5]naphthyridin-4-yl)-ethyl]-2-oxo-1-oxa-3-aza-spiro[4.5]dec-3-yl}-4H-benzo[1,4]oxazin-3-one

16.i. 5-(1,4-dioxa-spiro[4.5]dec-8-ylmethylsulfanyl)-1-phenyl-1H-tetrazole

A solution of 8-iodomethyl-1,4-dioxa-spiro[4.5]decane (prepared according to WO 2003/095438, 26 g, 92 mmol) was dissolved in EtOH (200 ml), 1-phenyl-1H-tetrazole-5-thiol (18.9 g, 106 mmol) and KOH (6.7 g, 120 mmol) was added and the mixture stirred at 80° C. for 2.5 h. A little water was added and the mixture concentrated in vacuo. The residue was taken up in water and EA. The yield after work up was 30.9 g (100%; yellowish oil).
$^1$H NMR (CDCl$_3$) δ: 7.80-7.60 (m, 5H); 3.95 (s, 4H); 3.37 (d, J=6.6 Hz, 2H); 2.00-1.75 (m, 5H); 1.60-1.30 (m, 4H).

16.ii. 5-(1,4-dioxa-spiro[4.5]dec-8-ylmethanesulfonyl)-1-phenyl-1H-tetrazole Intermediate 16.i (30 g, 90.2 mmol) was dissolved in EtOH (500 ml) and treated with aq. H$_2$O$_2$ (35%, 70 ml) and ammonium molybdate (22.3 g, 18 mmol). The mixture was stirred at 65° C. for 1.5 h. The mixture was taken up in water and EtOH was removed under reduced pressure. The aq. residue was extracted with EA. The yield after work up and chromatography (Hex:EA 2:1, 1:1) was 25 g (76%; colourless solid).
MS (ESI, m/z): 364.9 [M+H$^+$].

16.iii. 8-[(E)-2-(1,4-dioxa-spiro[4.5]dec-8-yl)-vinyl]-2-methoxy-[1,5]naphthyridine A suspension of 6-methoxy-[1,5]naphthyridine-4-carbaldehyde (2.0 g, 10.6 mmol, prepared according to WO 2006/

032466) and intermediate 16.ii (4.5 g, 12.3 mmol) in 1,2-DME (60 ml) was cooled to −60° C. KHMDS (0.5M in THF, 42 ml, 20.9 mmol) was added dropwise over 1 h. The resulting black solution was allowed to reach rt over 2 h. It was diluted with water (40 ml) and EA (200 ml). The yield after work up and chromatography (Hex/EA 1:1) was 2.47 g (71%; yellow oil).

$^1$H NMR (CDCl$_3$) δ: 8.52 (d, J=4.8 Hz, 1H); 8.08, (d, J=9.1 Hz, 1H); 7.47 (d, J=4.8 Hz, 1H); 7.35 (d, J=16.2 Hz, 1H); 6.90 (d, J=9.1 Hz, 1H); 6.59 (dd, J=7.2, 16.2 Hz, 1H); 3.96 (s, 3H); 3.82 (s, 4H); 2.30-2.15 (m, 1H); 1.80-1.40 (m, 8H).

16.iv. 4-[(E)-2-(6-methoxy-[1,5]naphthyridin-4-yl)-vinyl]-cyclohexanone

A solution of intermediate 16.iii (2.4 g, 7.4 mmol) in THF: H$_2$O:HOAc (2:2:3, 280 ml) was heated at reflux for 3 days. The mixture was concentrated and the residue taken up in EA and a NaHCO$_3$ solution. The yield after work up was 2.2 g (100%; colourless solid).

MS (ESI, m/z): 283.0 [M+H$^+$].

16.v. cis/trans-2-methoxy-8-[(E)-2-(1-oxa-spiro[2.5]oct-6-yl)-vinyl]-[1,5]naphthyridine The title compound was prepared starting from intermediate 16.iv (2.06 g, 7.3 mmol) and using the procedure of Example 6, step 6.i. It was isolated as a yellow oil (1.4 g, 64% yield) after chromatography (Hex:EA 1:1 then EA).

MS (ESI, m/z): 297.1 [M+H$^+$].

16.vi. cis/trans-6-(t{-hydroxy-4-[(E)-2-(6-methoxy-[1,5]naphthyridin-4-yl)-vinyl]-cyclohexylmethyl}-amino)-4H-benzo[1,4]oxazin-3-one The title compound was obtained as yellow oil starting from intermediate 16.v (0.43 g, 1.45 mmol) and 6-amino-4H-benzo[1,4]oxazin-3-one (0.24 g, 1.43 mmol) and following the procedure of Example 2, step 2.i. The yield after work up and chromatography (eluent EA/MeOH 9:1) was 0.45 g (67%).

MS (ESI, m/z): 460.7 [M+H$^+$].

16.vii. cis/trans-6-{8-[(E)-2-(6-methoxy-[/, 5]naphthyridin-4-yl)-vinyl]-2-oxo-1-oxa-3-aza-spiro[4.5]dec-3-yl}-4H-benzo[/,4]oxazin-3-one The title compound (0.082 g, 17% yield) was obtained as a beige foam starting from the mixture of isomers 16.vi (0.45 g, 0.98 mmol) and triphosgene and using the procedure of Example 2, step 2.i.

MS (ESI, m/z): 487.1 [M+H$^+$].

16.viii. cis/trans-6-{8-[2-(6-methoxy-[1,5]naphthyridin-4-yl)-ethyl]-2-oxo-1-oxa-3-aza-spiro[4.5]dec-3-yl}-4H-benzo[1,4]oxazin-3-one A solution of the above intermediate 16.vii (0.082 g, 0.17 mmol) in MeOH:THF (1:1, 3 ml) was hydrogenated over Pd/C for 6 h. The catalyst was removed by filtration and the filtrate concentrated in vacuo. The yield after chromatography (EA:MeOH 9:1) was 0.015 g (18% yield; beige solid).

MS (ESI, m/z): 489.1 [M+H$^+$].

Example 17 cis/trans-3-(2,3-dihydro-benzo[1,4]dioxin-6-yl)-8-[(E)-2-(6-methoxy-quinolin-4-yl)-vinyl]-1-oxa-3-aza-spiro[4.5]decan-2-one (mixture of isomers)

17.i. cis/trans-6-methoxy-4-[2-(1-oxa-spiro[2.5]oct-6-yl)-vinyl]-quinoline

The title epoxide was prepared starting from 6-methoxy-quinoline-4-carbaldehyde (3.0 g, 15.9 mmol) and following the procedures of steps 16.iii to 16.v of Example 167. The epoxide was isolated after chromatography (EA) as yellowish oil (0.9 g).

MS (ESI, m/z): 296.1 [M+H$^+$].

17.ii. cis/trans-1-[(2,3-dihydro-benzo[1,4]dioxin-6-ylamino)-methyl]-4-[(E)-2-(6-methoxy-quinolin-4-yl)-vinyl]-cyclohexanol The title compound was obtained as a yellowish oil, starting from intermediate 178.i (0.37 g, 0.85 mmol) and 6-amino-4H-benzo[1,4]oxazin-3-one (0.19 g, 1.25 mmol) and following the procedure of Example 2, step 2.i. The yield after work up and chromatography (eluent EA:MeOH 9:1) was 0.38 g.

MS (ESI, m/z): 446.9 [M+H$^+$].

17.iii. cis/trans-3-(2,3-dihydro-benzo[1,4]dioxin-6-yl)-8-[(E)-2-(6-methoxy-quinolin-4-yl)-vinyl]-1-oxa-3-aza-spiro[4.5]decan-2-one (mixture of isomers)

This compound (0.17 g, 41% yield) was obtained as an orange foam, starting from the mixture of isomers 17.iii (0.38 g, 0.85 mmol) and using the procedure of Example 2, step 2.ii.

MS (ESI, m/z): 472.9 [M+H$^+$].

Example 18 cis/trans-6-{8-[(E)-2-(6-methoxy-quinolin-4-yl)-vinyl]-2-oxo-1-oxa-3-aza-spiro[4.5]dec-3-yl}-4H-benzo[1,4]thiazin-3-one (mixture of isomers)

18.i. cis/trans-6-({1-hydroxy-4-[(E)-2-(6-methoxy-quinolin-4-yl)-vinyl]-cyclohexylmethyl}-amino)-4H-benzo[1,4]thiazin-3-one The title compound was obtained as yellowish oil, starting from intermediate 17.i (0.90 g, 3.05 mmol) and 6-amino-4H-benzo[1,4]thiazin-3-one (0.55 g, 3.05 mmol) and following the procedure of Example 2, step 2.i. The yield after work up and chromatography (eluent EA/MeOH 9:1) was 0.56 g (as a mixture of isomers).

MS (ESI, m/z): 475.9 [M+H$^+$].

18.ii. cis/trans-6-{8-[(E)-2-(6-methoxy-quinolin-4-yl)-vinyl]-2-oxo-1-oxa-3-aza-spiro[4.5]dec-3-yl}-4H-benzo[1,4]thiazin-3-one (mixture of isomers)

This compound (0.1 g, 17% yield) was obtained as a beige solid, starting from the mixture of isomers 17.ii (0.56 g, 1.17 mmol) and triphosgene and using the procedure of Example 2, step 2.ii.

MS (ESI, m/z): 502.0 [M+H$^+$].

Example 19 cis-3-(2,3-dihydro-benzo[1,4]dioxin-6-yl)-8-(6-methoxy-quinazolin-4-yloxymethyl)-1-oxa-3-aza-spiro[4.5]decan-2-one To a solution of intermediate 2.iv (0.25 g, 0.78 mmol) in DMF at 0° C. was added 4-chloro-6-methoxy-quinazoline (0.152 g, 1 eq) and a NaH dispersion (60% in paraffin oil, 0.034 g, 1.1 eq). The mixture was stirred at rt overnight, partitioned between water and EA. After workup, the product was crystallised from ether to yield 0.09 g of a colourless solid (24% yield).

$^1$H NMR (DMSO d6) δ: 8.68 (s, 1H); 7.86 (d, J=9.1 Hz, 1H); 7.60 (dd, J=9.1, 2.9 Hz 1H); 7.42 (d, J=2.9 Hz, 1H); 7.10 (d, J=2.4 Hz, 1H); 6.97 (dd, J=2.4, 9.3 Hz, 1H); 6.85 (d, J=9.3 Hz, 1H); 4.46 (d, J=6.0 Hz, 2H); 4.30-4.15 (m, 4H); 3.93 (s, 3H); 3.76 (s, 2H); 2.10-1.95 (m, 3H); 1.95-1.80 (m, 2H); 1.80-1.50 (m, 4H).

Pharmacological Properties of the Invention Compounds
In Vitro Assays
Experimental Methods:

These assays have been performed following the description given in "Methods for dilution Antimicrobial Susceptibility Tests for Bacteria that Grow Aerobically, 4th ed.; Approved standard: NCCLS Document M7-A4; National Committee for Clinical Laboratory Standards Villanova, Pa., USA, 1997". Minimal inhibitory concentrations (MICs; mg/l) were determined in cation-adjusted Mueller-Hinton Broth (BBL) by a microdilution method following NCCLS guidelines (National Committee for Clinical Laboratory Standards. Methods for Dilution Antimicrobial Susceptibility). The pH of the test medium was 7.2-7.3.

Results:

All Example compounds were tested against several Gram positive and Gram negative bacteria. Typical antibacterial test results are given in the table hereafter (MIC in mg/l).

| Example No. | S. aureus A798 | S. pneumoniae 49619 | M. catarrhalis A894 |
|---|---|---|---|
| 18 | ≤0.031 | 0.125 | ≤0.031 |
| 19 | 0.125 | 0.25 | 0.5 |

Besides, the following results have been obtained on S. aureus A798 (MIC in mg/l):

| Example No. | S. aureus A798 |
|---|---|
| 1 | 0.5 |
| 2 | 0.25 |
| 3 | 2 |
| 4 | ≤0.031 |
| 5 | ≤0.031 |
| 6 | 1 |
| 7 | 2 |
| 8 | 1 |
| 9 | ≤0.031 |
| 10 | 0.125 |
| 11 | 0.25 |
| 12 | ≤0.031 |
| 13 | ≤0.031 |
| 14 | ≤0.031 |
| 15 | ≤0.031 |
| 16 | ≤0.031 |
| 17 | 2 |
| 18 | ≤0.031 |
| 19 | 0.125 |

The invention claimed is:
1. A compound of formula (I)

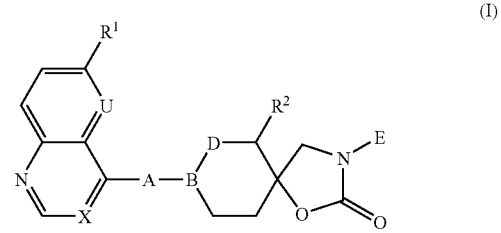

wherein
R$^1$ represents alkoxy;
one of U and X represents CH or N and the other represents CH, or, in the case of U, may also represent CR$^a$ and, in the case of X, may also represent CR$^b$;
R$^a$ represents halogen;
R$^b$ represents halogen or alkoxy;
B represents N, D represents CH$_2$ and A represents CH(OH)CH$_2$ or CH$_2$CH$_2$, or
B represents CH, D represents CH$_2$ or O and A represents OCH$_2$, CH$_2$CH(OH), CH(OH)CH$_2$, CH(OH)CH(OH), CH=CH, CH$_2$CH$_2$ or NHCO, or also
B represents C(OH), D represents CH$_2$ and A represents OCH$_2$, CH$_2$CH(OH), CH(OH)CH$_2$, CH(OH)CH(OH), CH=CH, CH$_2$CH$_2$ or NHCO;
R$^2$ represents H, alkenyl, hydroxyalkyl or alkoxycarbonylalkyl; and
E represents a binuclear heterocyclic group of the formula:

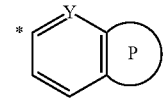

wherein Y is CH or N and the ring P is selected from the following

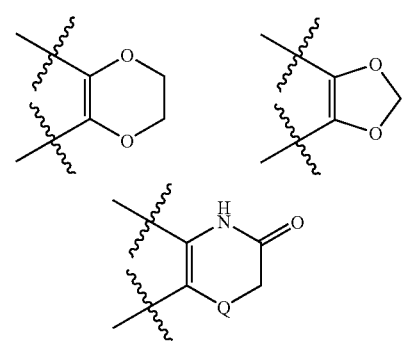

in which Q is O or S;
or a salt of said compound.

2. The compound of formula (I) according to claim 1, wherein R¹ represents (C₁-C₃)alkoxy; or a salt of said compound.

3. The compound of formula (I) according to claim 1, wherein R¹ represents methoxy; or a salt of said compound.

4. The compound of formula (I) according to claim 1, wherein both U and X represent CH or U represents N and X represents CH; or a salt of said compound.

5. The compound of formula (I) according to claim 1, wherein Y is CH;
or a salt of said compound.

6. The compound of formula (I) according to claim 1, wherein R² represents H or alkenyl; or a salt of said compound.

7. The compound of formula I according to claim 1, wherein the compound is
(5R,6R,8S)-3-(2,3-dihydro-benzo[1,4]dioxin-6-yl)-8-[(2R)-2-hydroxy-2-(6-methoxy-[1,5]naphthyridin-4-yl)-ethyl]-6-hydroxymethyl-1,7-dioxa-3-aza-spiro[4.5]decan-2-one;
(5R,6R,8S)-3-(2,3-dihydro-benzo[1,4]dioxin-6-yl)-8-[(2S)-2-hydroxy-2-(6-methoxy-[1,5]naphthyridin-4-yl)-ethyl]-6-hydroxymethyl-1,7-dioxa-3-aza-spiro[4.5]decan-2-one;
cis-3-(2,3-dihydro-benzo[1,4]dioxin-6-yl)-8-(6-methoxy-quinolin-4-yloxymethyl)-1-oxa-3-aza-spiro[4.5]decan-2-one;
cis-3-(2,3-dihydro-benzo[1,4]dioxin-6-yl)-8-(6-methoxy-[1,5]naphthyridin-4-yloxymethyl)-1-oxa-3-aza-spiro[4.5]decan-2-one;
3-(2,3-dihydro-benzo[1,4]dioxin-6-yl)-8-[(2R)-2-hydroxy-2-(6-methoxy-quinolin-4-yl)-ethyl]-1-oxa-3,8-diaza-spiro[4.5]decan-2-one;
3-(2,3-dihydro-benzo[1,4]dioxin-6-yl)-8-[(2S)-2-hydroxy-2-(6-methoxy-quinolin-4-yl)-ethyl]-1-oxa-3,8-diaza-spiro[4.5]decan-2-one;
6-{8-[(2R)-2-hydroxy-2-(6-methoxy-quinolin-4-yl)-ethyl]-2-oxo-1-oxa-3,8-diaza-spiro[4.5]dec-3-yl}-4H-benzo[1,4]thiazin-3-one;
6-{8-[(2S)-2-hydroxy-2-(6-methoxy-quinolin-4-yl)-ethyl]-2-oxo-1-oxa-3,8-diaza-spiro[4.5]dec-3-yl}-4H-benzo[1,4]thiazin-3-one;
(5R,6R)-6-allyl-3-(2,3-dihydro-benzo[1,4]dioxin-6-yl)-8-[(2R)-2-hydroxy-2-(6-methoxy-quinolin-4-yl)-ethyl]-1-oxa-3,8-diaza-spiro[4.5]decan-2-one;
(5R,6R)-6-allyl-3-(2,3-dihydro-benzo[1,4]dioxin-6-yl)-8-[(2S)-2-hydroxy-2-(6-methoxy-quinolin-4-yl)-ethyl]-1-oxa-3,8-diaza-spiro[4.5]decan-2-one;
(5R,6S)-6-allyl-3-(2,3-dihydro-benzo[1,4]dioxin-6-yl)-8-[(2R)-2-hydroxy-2-(6-methoxy-quinolin-4-yl)-ethyl]-1-oxa-3,8-diaza-spiro[4.5]decan-2-one;
(5R,6S)-6-allyl-3-(2,3-dihydro-benzo[1,4]dioxin-6-yl)-8-[(2S)-2-hydroxy-2-(6-methoxy-quinolin-4-yl)-ethyl]-1-oxa-3,8-diaza-spiro[4.5]decan-2-one;
(5S,6R)-6-allyl-3-(2,3-dihydro-benzo[1,4]dioxin-6-yl)-8-[(2R)-2-hydroxy-2-(6-methoxy-quinolin-4-yl)-ethyl]-1-oxa-3,8-diaza-spiro[4.5]decan-2-one;
(5S,6R)-6-allyl-3-(2,3-dihydro-benzo[1,4]dioxin-6-yl)-8-[(2S)-2-hydroxy-2-(6-methoxy-quinolin-4-yl)-ethyl]-1-oxa-3,8-diaza-spiro[4.5]decan-2-one;
(5S,6S)-6-allyl-3-(2,3-dihydro-benzo[1,4]dioxin-6-yl)-8-[(2R)-2-hydroxy-2-(6-methoxy-quinolin-4-yl)-ethyl]-1-oxa-3,8-diaza-spiro[4.5]decan-2-one;
(5S,6S)-6-allyl-3-(2,3-dihydro-benzo[1,4]dioxin-6-yl)-8-[(2S)-2-hydroxy-2-(6-methoxy-quinolin-4-yl)-ethyl]-1-oxa-3,8-diaza-spiro[4.5]decan-2-one;
(5R,6R)-{3-(2,3-dihydro-benzo[1,4]dioxin-6-yl)-8-[(2R)-2-hydroxy-2-(6-methoxy-quinolin-4-yl)-ethyl]-2-oxo-1-oxa-3,8-diaza-spiro[4.5]dec-6-yl}-acetic acid methyl ester;
(5R,6R)-{3-(2,3-dihydro-benzo[1,4]dioxin-6-yl)-8-[(2S)-2-hydroxy-2-(6-methoxy-quinolin-4-yl)-ethyl]-2-oxo-1-oxa-3,8-diaza-spiro[4.5]dec-6-yl}-acetic acid methyl ester;
(5R,6S)-{3-(2,3-dihydro-benzo[1,4]dioxin-6-yl)-8-[(2R)-2-hydroxy-2-(6-methoxy-quinolin-4-yl)-ethyl]-2-oxo-1-oxa-3,8-diaza-spiro[4.5]dec-6-yl}-acetic acid methyl ester;
(5R,6S)-{3-(2,3-dihydro-benzo[1,4]dioxin-6-yl)-8-[(2S)-2-hydroxy-2-(6-methoxy-quinolin-4-yl)-ethyl]-2-oxo-1-oxa-3,8-diaza-spiro[4.5]dec-6-yl}-acetic acid methyl ester;
(5S,6R)-{3-(2,3-dihydro-benzo[1,4]dioxin-6-yl)-8-[(2R)-2-hydroxy-2-(6-methoxy-quinolin-4-yl)-ethyl]-2-oxo-1-oxa-3,8-diaza-spiro[4.5]dec-6-yl}-acetic acid methyl ester;
(5S,6R)-{3-(2,3-dihydro-benzo[1,4]dioxin-6-yl)-8-[(2S)-2-hydroxy-2-(6-methoxy-quinolin-4-yl)-ethyl]-2-oxo-1-oxa-3,8-diaza-spiro[4.5]dec-6-yl}-acetic acid methyl ester;
(5S,6S)-{3-(2,3-dihydro-benzo[1,4]dioxin-6-yl)-8-[(2R)-2-hydroxy-2-(6-methoxy-quinolin-4-yl)-ethyl]-2-oxo-1-oxa-3,8-diaza-spiro[4.5]dec-6-yl}-acetic acid methyl ester;
(5S,6S)-{3-(2,3-dihydro-benzo[1,4]dioxin-6-yl)-8-[(2S)-2-hydroxy-2-(6-methoxy-quinolin-4-yl)-ethyl]-2-oxo-1-oxa-3,8-diaza-spiro[4.5]dec-6-yl}-acetic acid methyl ester;
(5R,6R)-3-(2,3-dihydro-benzo[1,4]dioxin-6-yl)-6-(2-hydroxy-ethyl)-8-[(2R)-2-hydroxy-2-(6-methoxy-quinolin-4-yl)-ethyl]-1-oxa-3,8-diaza-spiro[4.5]decan-2-one;
(5R,6R)-3-(2,3-dihydro-benzo[1,4]dioxin-6-yl)-6-(2-hydroxy-ethyl)-8-[(2S)-2-hydroxy-2-(6-methoxy-quinolin-4-yl)-ethyl]-1-oxa-3,8-diaza-spiro[4.5]decan-2-one;
(5R,6S)-3-(2,3-dihydro-benzo[1,4]dioxin-6-yl)-6-(2-hydroxy-ethyl)-8-[(2R)-2-hydroxy-2-(6-methoxy-quinolin-4-yl)-ethyl]-1-oxa-3,8-diaza-spiro[4.5]decan-2-one;
(5R,6S)-3-(2,3-dihydro-benzo[1,4]dioxin-6-yl)-6-(2-hydroxy-ethyl)-8-[(2S)-2-hydroxy-2-(6-methoxy-quinolin-4-yl)-ethyl]-1-oxa-3,8-diaza-spiro[4.5]decan-2-one;
(5S,6R)-3-(2,3-dihydro-benzo[1,4]dioxin-6-yl)-6-(2-hydroxy-ethyl)-8-[(2R)-2-hydroxy-2-(6-methoxy-quinolin-4-yl)-ethyl]-1-oxa-3,8-diaza-spiro[4.5]decan-2-one;
(5S,6R)-3-(2,3-dihydro-benzo[1,4]dioxin-6-yl)-6-(2-hydroxy-ethyl)-8-[(2S)-2-hydroxy-2-(6-methoxy-quinolin-4-yl)-ethyl]-1-oxa-3,8-diaza-spiro[4.5]decan-2-one;
(5S,6S)-3-(2,3-dihydro-benzo[1,4]dioxin-6-yl)-6-(2-hydroxy-ethyl)-8-[(2R)-2-hydroxy-2-(6-methoxy-quinolin-4-yl)-ethyl]-1-oxa-3,8-diaza-spiro[4.5]decan-2-one;
(5S,6S)-3-(2,3-dihydro-benzo[1,4]dioxin-6-yl)-6-(2-hydroxy-ethyl)-8-[(2S)-2-hydroxy-2-(6-methoxy-quinolin-4-yl)-ethyl]-1-oxa-3,8-diaza-spiro[4.5]decan-2-one;
cis-3-(2,3-dihydro-benzo[1,4]dioxin-6-yl)-2-oxo-1-oxa-3-aza-spiro[4.5]decane-8-carboxylic acid (6-methoxy-[1,5]naphthyridin-4-yl)-amide;

trans-3-(2,3-dihydro-benzo[1,4]dioxin-6-yl)-2-oxo-1-oxa-3-aza-spiro[4.5]decane-8-carboxylic acid (6-methoxy-[1,5]naphthyridin-4-yl)-amide;

cis-3-(2,3-dihydro-benzo[1,4]dioxin-6-yl)-8-hydroxy-8-[2-(6-methoxy-[1,5]naphthyridin-4-yl)-ethyl]-1-oxa-3-aza-spiro[4.5]decan-2-one;

trans-3-(2,3-dihydro-benzo[1,4]dioxin-6-yl)-8-hydroxy-8-[2-(6-methoxy-[1,5]naphthyridin-4-yl)-ethyl]-1-oxa-3-aza-spiro[4.5]decan-2-one;

cis-6-8-hydroxy-8-{2-(6-methoxy-[1,5]naphthyridin-4-yl)-ethyl]-2-oxo-1-oxa-3-aza-spiro[4.5]dec-3-yl}-4H-benzo[1,4]thiazin-3-one;

trans-6-{8-hydroxy-8-[2-(6-methoxy-[1,5]naphthyridin-4-yl)-ethyl]-2-oxo-1-oxa-3-aza-spiro[4.5]dec-3-yl}-4H-benzo[1,4]thiazin-3-one;

cis-6-{8-hydroxy-8-[2-(6-methoxy-[1,5]naphthyridin-4-yl)-ethyl]-2-oxo-1-oxa-3-aza-spiro[4.5]dec-3-yl}-4H-benzo[1,4]oxazin-3-one;

trans-6-{8-hydroxy-8-[2-(6-methoxy-[1,5]naphthyridin-4-yl)-ethyl]-2-oxo-1-oxa-3-aza-spiro[4.5]dec-3-yl}-4H-benzo[1,4]dioxazin-3-one;

cis-3-[2-(6-methoxy-[1,5]naphthyridin-4-yl)-ethyl]-2-oxo-1-oxa-3-aza-spiro[4.5]dec-3-yl}-4H-benzo[1,4]oxazin-3-one;

trans-6-{8-[2-(6-methoxy-[1,5]naphthyridin-4-yl)-ethyl]-2-oxo-1-oxa-3-aza-spiro[4.5]dec-3-yl}-4H-benzo[1,4]oxazin-3-one;

cis-3-(2,3-dihydro-benzo[1,4]dioxin-6-yl)-8-[(E)-2-(6-methoxy-quinolin-4-yl)-vinyl]-1-oxa-3-aza-spiro[4,5]decan-2-one;

trans-3-(2,3-dihydro-benzo[1,4]dioxin-6-yl)-8-[(E)-2-(6-methoxy-quinolin-4-yl)-vinyl]-1-oxa-3-aza-spiro[4.5]decan-2-one;

cis-6-[8-[(E)-2-(6-methoxy-quinolin-4-yl)-vinyl]-2-oxo-1-oxa-3-aza-spiro[4.5]dec-3-yl]-4H-benzo[1,4]thiazin-3-one;

trans-6-{8-[(E)-2-(6-methoxy-quinolin-4-yl)-vinyl]-2-oxo-1-oxa-3-aza-spiro[4.5]dec-3-yl}-4H-benzo[1,4]thiazin-3-one;

cis-3-(2,3-dihydro-benzo[1,4]dioxin-6-yl)-8-(6-methoxy-quinazolin-4-yloxymethyl)-1-oxa-3-aza-spiro[4.5]decan-2-one;

or a salt of said compound.

8. A medicament comprising the compound of formula (I) as defined in claim 1 or a pharmaceutically acceptable salt thereof.

9. A pharmaceutical composition comprising a therapeutically effective amount of the compound of formula (I) as defined in claim 1 or a pharmaceutically acceptable salt of said compound, and at least one therapeutically inert excipient.

10. A compound of formula (I$_{CE}$)

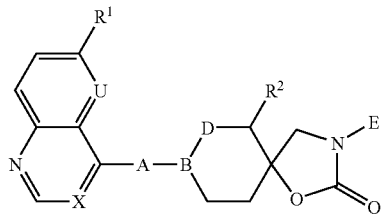

(I$_{CE}$)

wherein

R$^1$ represents alkoxy;

U represents N and X represents CH, or each of U and X represents CH, or also each of U represents CH and X represents N;

B represents N, D represents CH$_2$ and A represents CH(OH)CH$_2$, or

B represents CH, D represents CH$_2$ and A represents OCH$_2$, CH(OH)CH(OH), CH=CH or NHCO, or B represents CH, D represents O and A represents CH(OH)CH$_2$, or also B represents C(OH), D represents CH$_2$ and A represents CH$_2$CH$_2$;

R$^2$ represents H, alkenyl, hydroxyalkyl or alkoxycarbonylalkyl; and

E represents a binuclear heterocyclic group of the formula

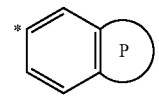

wherein the ring P is selected from the following

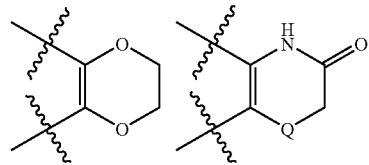

in which Q is O or S;

or a salt of said compound.

11. The compound of formula (I$_{CE}$) according to claim 10, wherein R$^1$ represents methoxy;

or a salt of said compound.

12. The compound of formula (I$_{CE}$) according to claim 10, wherein R$^2$ represents H;

or a salt of said compound.

* * * * *